US012653903B2

(12) United States Patent
Lo

(10) Patent No.: US 12,653,903 B2
(45) Date of Patent: Jun. 16, 2026

(54) NANOPARTICLE AND USE THEREOF FOR THE COMBINATORIAL THERAPY OF ENDOPLASMIC RETICULUM STRESS INDUCER AND IMMUNOTHERAPEUTIC TO TUMORS AND IMMUNE CELLS

(71) Applicant: National Yang Ming Chiao Tung University, Taipei (TW)

(72) Inventor: Yu-Li Lo, Taipei City (TW)

(73) Assignee: NATIONAL YANG MING CHIAO TUNG UNIVERSITY, Taipei (TW)

( * ) Notice: Subject to any disclaimer, the term of this patent is extended or adjusted under 35 U.S.C. 154(b) by 401 days.

(21) Appl. No.: 18/353,723

(22) Filed: Jul. 17, 2023

(65) Prior Publication Data

US 2024/0245803 A1     Jul. 25, 2024

(30) Foreign Application Priority Data

Jan. 19, 2023    (TW) ................................. 112102775

(51) Int. Cl.
    *A61K 47/69*        (2017.01)
    *A61K 45/06*        (2006.01)
                (Continued)
(52) U.S. Cl.
    CPC .......... *A61K 47/6935* (2017.08); *A61K 45/06* (2013.01); *A61K 47/543* (2017.08);
                (Continued)
(58) Field of Classification Search
    CPC ....... B82Y 5/00; A61P 35/00; A61K 47/6935; A61K 47/543; A61K 47/554; A61K 47/66; A61K 45/06
    See application file for complete search history.

(56) References Cited

U.S. PATENT DOCUMENTS 8,314,223 B2 * 11/2012 Purschke ................ A61P 35/04
                                                    536/23.1
11,141,491 B2 * 10/2021 Lo .......................... C12N 15/88
                (Continued)

OTHER PUBLICATIONS

Yu-Li Lo et al., "Exploring in vivo combinatorial chemo-immunotheraphy: Addressing p97 suppression and immune reinvigoration in pancreatic cancer with tumor microenvironment-responseive nanoformulation", Biomedicine & Pharmacotherapy 175 (Apr. 24, 2024) 116660, 19 pages.

(Continued)

*Primary Examiner* — Sean M Basquill
(74) *Attorney, Agent, or Firm* — MUNCY, GEISSLER, OLDS & LOWE, P.C.

(57)                     ABSTRACT

Multifunctional nanoparticles incorporate an ERS inducer (p97 inhibitors) and immunotherapeutics (immune-modulating miR or aptamer plus immunoadjuvants) to address the poor aqueous solubility and toxicity associated with p97 inhibitors and immunotherapeutics while also enhancing the immune activation of these therapeutics. The nanoformulation offers several advantages, such as pH-sensitivity, self-detachable coating, active targeting, and intracellular localization in tumors, and has the potential to overcome the limitations of systemic administration, such as the degradation of nucleic acid therapeutics and toxicities associated with ERS inducer.

21 Claims, 61 Drawing Sheets

Specification includes a Sequence Listing.

(51) Int. Cl.

| | |
|---|---|
| *A61K 47/54* | (2017.01) |
| *A61K 47/66* | (2017.01) |
| *A61P 35/00* | (2006.01) |
| *B82Y 5/00* | (2011.01) |

(52) U.S. Cl.
CPC ............ *A61K 47/554* (2017.08); *A61K 47/66* (2017.08); *A61P 35/00* (2018.01); *B82Y 5/00* (2013.01)

(56) References Cited

U.S. PATENT DOCUMENTS

| | | | | |
|---|---|---|---|---|
| 11,261,428 | B2 * | 3/2022 | Benson | A61P 35/00 |
| 11,690,803 | B2 * | 7/2023 | Lo | A61K 31/555 |
| | | | | 424/400 |
| 2016/0091489 | A1 * | 3/2016 | Fan | G01N 33/56966 |
| | | | | 435/7.2 |
| 2022/0119451 | A1 * | 4/2022 | Cheng | A61K 38/08 |

OTHER PUBLICATIONS

Ching-Yao Li et al., "An innovative nanoforumulation utilizing tumor microenvironment-responsive PEG-polyglutamic coating and dynamic charge adjustment for specific targeting of ER stress inducer, microRNA, and immunoadjuvant in pancreatic cancer: In vitro investigations", International Journal of Biological Macromolecules 254, (Nov. 6, 2023) 127905, 23 pages.

Yu-Li Lo et al., "Functional pH-Responsive Nanoparticles for Immune REporgramming in MSS Colorectal Cancer via ER Stress-Induced Proteostasis Disruption, PD-L1-Targeting miRNA, and TLR7 Actrivation", Pharmaceutics MDPI Article, 42 pages, Published Nov. 20, 2025, https://doi.org/10.3390/pharmaceutics17111503.

Yu-Li Lo et al., "TME-responsive nanoparticles co-targeting VCP, NET's, and dual immune checkpoints for immune revitalization in EGFR/PD-LI/CTLA-4-driven colorectal cancer", Biomedicine & Pharmacotherapy 192 (Sep. 18, 2025) 118565, journal home page: www.elsevier.com/locate/biopha, 30 pages.

* cited by examiner

1

NANOPARTICLE AND USE THEREOF FOR THE COMBINATORIAL THERAPY OF ENDOPLASMIC RETICULUM STRESS INDUCER AND IMMUNOTHERAPEUTIC TO TUMORS AND IMMUNE CELLS

REFERENCE TO AN ELECTRONIC SEQUENCE LISTING

The contents of the electronic sequence listing (YC22PA168-US.xml; Size: 12 KB; and Date of Creation: 2023-05-23) is herein incorporated by reference in its entirety.

CROSS-REFERENCE TO RELATED APPLICATIONS

This application claims priority in Taiwan Patent Application No. 112102775, filed on Jan. 19, 2023, which is incorporated by reference in its entirety herein.

FIELD OF THE INVENTION

The present invention relates to a novel endoplasmic reticulum and immune cell target nanoparticle which contain endoplasmic reticulum stress (ERS) inducer or immunotherapeutic (immunoadjuvant plus aptamer or microRNA) and its use thereof.

BACKGROUND OF THE INVENTION

The present invention relates to a novel technology platform for delivering ERS inducer or immunotherapeutic (aptamer or microRNA plus immunoadjuvant) to tumor and immune cells and its use thereof.

Cancer is one of the leading causes of death worldwide. The compounds involved in induction of ERS including CB-5083 (hereinafter referred to as CB). NMS-873 (hereinafter referred to as NM). DBeQ. CB-5339, and others. They can be used to treat hematological and solid tumors, such as colorectal cancer, multiple myeloma, and lung cancer. This type of treatment has a novel antitumor mechanism, but these ERS inducers cause side effects due to off-target effects in normal tissues or organs, resulting in toxicity to normal cells and leading to drug resistance, which hinders the anticancer effects of ERS inducing agents at the target tumor site.

Immunotherapy has been continuously developed as one of the most promising cancer treatments. Nucleic acid immunomodulators trigger the high immunity in macrophages to cause macrophage induction and immune activation. Upregulation of miR such as miR-142 can enhance classically activated macrophages (M1) to improve antitumor effect, but miR-142 will also reduce the immune escape of tumor cells. Activation of miR-142 expression may cause tumor-associated macrophages (TAM) repolarization from alternatively activated macrophages (M2) to classically activated macrophages (M1), thus inhibiting primary tumor growth and metastasis or invasion of tumors. Aptamers may have tumor and immune cell specificities and can improve antitumor immune response. Aptamers are oligonucleotide derivatives that target specific proteins. Because of their small size, long shelf lives, and ease of synthesis and modification, aptamers gained increasing recognition. Therefore, aptamers can increase the targeting to tumors (such as pancreatic cancer, colorectal cancer, and head and neck cancer) and immune cells to exert antitumor and immunoregulatory effects by screening aptamers or peptides that can bind to receptors or targets such as VEGFR, EGFR, CXCR4, CD44, CTLA-4, PD-1, PD-L1 or neutrophil.

However, nucleic acid immunomodulators are very unstable in biological systems due to poor cell permeability and rapid degradation by nuclease. Moreover, nucleic acid immunoadjuvants may have drawbacks, such as triggering the innate immune system and potential off-target effects. Furthermore, as a monotherapy: their efficacy as immunotherapeutic agents is relatively weak.

Therefore, additional antitumor immunoadjuvants need to be added as an effective antitumor enhancer. Common immunoadjuvants include: resiquimod (R848, R), which is a toll-like receptor (TLR 7/8 agonist) that can strengthen and enhance the immune effect of nucleic acid immunomodulators. R promotes the maturation of dendritic cells and natural killer (NK) cells while inhibiting the interaction of programmed cell death protein 1 (PD-1) and programmed death-ligand 1 (PD-L1), thereby reactivating the T cells and increasing the antitumor immune response. Imiquimod (R837), a toll-like receptor 7 (TLR7) agonist, can regulate immune response. Vadimezan (dimethylxanthone acetic acid; DMXAA, ASA404) is a small molecular inhibitor of vascular endothelial growth factor (VEGF) and its receptor (VEGFR1, VEGFR2). Indoximod (1-methyl-D-tryptophan. NLG-8189) is a small molecular inhibitor of indoleamine 2,3-dioxygenase (IDO) pathway. AZD5069, a small molecular inhibitor of the CXCR2 receptor of interleukin-8 (IL-8), restricts the response of neutrophils and delays tumor progression. DNase (DN) is a negative regulator of neutrophil extracellular traps (NETs) and can be used to improve antitumor immune responses and reduce chemoresistance. Lorlatinib can control tumor-associated neutrophils (TANs) to enhance the effect of anti-PD1 therapy. Galunisertib (LY-2157299, hereinafter referred to as G) and SB-431542, two important TGF-β inhibitors, can improve the polarization of TANs into NI types, thereby enhancing long-term antitumor immune memory. Lanraplenib and Reparixin (DF 1681Y), prospective inhibitors of interleukin-8 (IL-8) and its CXCR2 receptor, can inhibit TANs and tumor-associated macrophages (TAMs) to improve immune checkpoint blockade and enhance antitumor immune responses. T peptide can affect IL-23 signaling and regulate transcriptional activator STAT3, thus inhibiting the role of TANs and TAMs to promote the antitumor immune response. However, direct use of immunoadjuvants may cause systemic inflammation and serious immune-related adverse events, such as anemia, flu-like symptoms, and lymphopenia.

In addition, the major challenges for the use of ERS inducers (including CB and NM), and most of antitumor immunoadjuvants in the present invention (such as R848), are their poor water solubility, high drug toxicity, and non-selective uptake by normal cells, which may cause systemic immune activation. Simultaneously, due to the poor water solubility of most ERS inducers and antitumor immunoadjuvants, they cannot be efficiently dissolved in aqueous media for further fabrication into nanoparticles. In general, medical field. ERS inducers are injected or administered to human body by dissolving or dispersing the drugs in vehicles, tablets or capsules, etc. These formulations cannot effectively target specific tumor cells and may affect normal cells, causing adverse effects. Therefore, nanoparticles are modified with aptamers or peptides that can bind to VEGFR, EGFR, CXCR4, CD44, CTLA-4, PD-1, PD-L1 or neutrophil. These aptamers or peptides increase targeting to tumors (such as pancreatic cancer, colorectal cancer, and head and neck cancer) and immune cells, exerting antitumor and immunoregulatory effects, and avoiding side effects.

SUMMARY OF THE INVENTION

In view of the aforementioned problem, the present invention provides a three-in-one nanoparticle formulation for delivering ERS inducer or immunotherapeutic (nucleic acid immunomodulator combined with immunoadjuvant (e.g., R848). Nucleic acid immunomodulator include aptamer (e.g., PIC4) or microRNA (e.g., miR-142)). Three-in-one nanoparticle can specifically deliver drugs into cancer cells. TAMs. or TANs to enhances ERS and immunogenic cell death (ICD) without triggering normal cell toxicity: The targeted nanoparticle in the present invention comprising ERS-inducing agent, nucleic acid immunomodulator, and immunoadjuvant can inhibit pathways involved in cancer proliferation, metastasis, or drug resistance in cancer cells, including proto-oncogenes, cell cycle regulators, and immunosuppressive cytokines, and enhance immune-promoting cytokines.

The nanoparticle is modified with EGFR-targeted C peptide, endoplasmic reticulum-localized S peptide, and PD-L1-targeted W peptide to deliver ERS inducer (such as CB), immune regulator (such as miR-142 or aptamers P1 and PIC4) and immunoadjuvant (such as R) to form CB+miR+R/SLN-CSW.

Moreover, the present invention shows the design of tumor pH-responsive coating as a detachable outer shell of nanoparticle to form CB+miR+R/PGA-SLN-CSW, which can specifically deliver immune-gene-chemotherapy to tumors, endoplasmic reticulum, and immune cells in treatment of colorectal, head and neck, and pancreatic cancer, as well as other tumors.

In addition, solid lipid nanoparticle (SLN) is modified with CD44 receptor-targeting Ac aptamer. CXCR4 receptor-targeting Ax aptamer, endoplasmic reticulum-directing O peptide, and PD-L1-targeting V peptide to deliver ERS inducer (such as NM), immune regulator (such as PIC4), and immunoadjuvant (such as Lanraplenib), thus forming NM+PIC4+L/SLN-AcAxOV.

The peptide- or aptamer-modified SLN is further coated with the tumor pH-sensitive polyethylene glycol (PEG)-polyglutamic acid (PGA) or PEG 5000 polymer. O'-methyl polyethylene glycol (omPEG) shell to form CB+miR+R/PGA-SLN-CSW or NM+PIC4+L/SLN-omAcAxOV. At physiological pH, the negative charges in the PGA shell can form space and charge barrier to protect the cationic C. S and W peptide on the surface of SLN nanoparticle through electrostatic interaction. This prevents the peptide from being degraded by decomposing enzymes during systemic circulation. At the same physiological pH, the long-chain omPEG shell can form a space barrier to protect the anionic aptamer on the surface of SLN nanoparticles and prevent the aptamer from being degraded by decomposing enzymes during systemic circulation. The nanoparticle can initially accumulate passively at the tumor site via enhanced permeability and retention (EPR) effects. Subsequently, the PEG-PGA or omPEG shell can be detached at the acidic pH of the tumor microenvironment.

Imine-O'-methyl polyethylene glycol (hereinafter referred to as omPEG) is a pH-sensitive linkage. Our findings further elucidate that the nanoparticle, which encapsulates the combinational therapy, can be modulated in the tumor microenvironment. They demonstrate superior tumor accumulation, mainly attributed to their pH-responsiveness and tumor targeting design.

The invention presents a nanoparticle that can deliver formulations of ERS inducer and immunotherapeutic to tumors, endoplasmic reticulum, and immune cells, and the uses thereof.

The major purpose of present invention is a target nanoparticle, comprising a nanoparticle core, wherein the surface of the nanoparticle core is modified with a target molecule: a therapeutic agent inside the nanoparticle core: and an outer shell layer surrounding the outside surface of the nanoparticle core, the outer shell layer is coated with a tumor microenvironment acid-detachable polymer. Wherein the target molecule of the surface of the nanoparticle core and the tumor microenvironment acid-detachable polymer of the outer layer form a space and charge barrier via the electrostatic interaction: wherein the target molecule comprises a cation target peptide and/or an anion target aptamer: wherein the cation target peptide comprises a tumor target peptide, an immune cell target peptide, an endoplasmic reticulum target peptide or a combination thereof: wherein the anion target aptamer comprises a tumor target aptamer, an immune cell target aptamer or a combination thereof: wherein the therapeutic agent comprises a ERS inducer and a nucleic acid immunomodulator.

In one embodiment, the tumor microenvironment acid-detachable polymer is PGA-PEG or omPEG.

In one embodiment, the nanoparticle core is solid lipid nanoparticle (SLN), the nanoparticle core comprises L-$\alpha$-phosphatidylcholine, glycerol monostearate, glycerol monopalmitate, glycerol monooleate, DSPE, DPPE, DOPE, DOTAP, DOTMA, SAINT 2, MC3 or KC2.

In one perfect embodiment, the therapeutic agent further comprises an immunoadjuvant.

In one embodiment, the nucleic acid immunomodulator is a nuclear aptamer or a miRNA.

In one embodiment, the nuclear aptamer is selected from the group consisting of Apt for anti-programmed cell death ligand-1; anti-PD-L1 (P1), Apt for anti-programmed cell death protein-1; anti-PD-1($A_p$), anti-PD-L1/anti-cytotoxic T lymphocyte associated antigen-4; anti-CTLA-4(Apt(PIC4)), anti-lymphocyte activation gene 3; (LAG-3)Apt($A_{lag}$), and anti-T cell immunoglobulin and mucin domain-3 (TIM-3) Apt ($A_t$).

In one embodiment, the miRNA is a has-miR-21 inhibitor or a miRNA mimic, wherein the miRNA mimic is selected from the group consisting of has-miR-122-5p, has-miR-125b-5p, has-miR-136-5p, has-miR-139-5p, has-miR-142-5p, has-miR-200c-3p, and has-miR-320.

In one embodiment, the ERS inducer comprises CB-5083, NMS-873, DBeQ, CB-5339 or Gemcitabine.

In one embodiment, the immunoadjuvant comprises resiquimod (R848, R), Imiquimod (R837), Vadimezan (dimethylxanthone acetic acid: DMXAA, ASA404), Indoximod (1-methyl-D-tryptophan, NLG-8189), DNase (DN), Lorlatinib, Galunisertib (LY-2157299, G), SB-431542, Lanraplenib, Reparixin (DF 1681Y) or T peptide (SEQ ID NO. 1: TEEEQQLY).

In one embodiment, the tumor microenvironment acid-detachable polymer can respond to an acidic pH to become protonated and detached from the target nanoparticle in a pH 5-6.5 environment or tumor microenvironment.

In one embodiment, the nanoparticle core is a solid lipid nanoparticle (SLN).

In one embodiment, the target molecule comprises a cation target peptide and/or an anion target aptamer.

In one embodiment, the cation target peptide or the anion target aptamer can bind with receptor of over performance of EGFR, VEGFR, CXCR4, and CD44 on tumor.

In one embodiment, the cation target peptide or the anion target aptamer can bind with PD-1, PD-L1, neutrophil or other targets on immune cells such as macrophages, T cells or neutrophils.

In one embodiment, the cation target peptide comprises a tumor target peptide, an immune cell target peptide, and an endoplasmic reticulum target peptide.

In one embodiment, the anion target aptamer comprises a tumor target aptamer and an immune cell target aptamer.

In one embodiment, the tumor target peptide is C peptide (SEQ ID NO. 2: KLARLLTC).

In one embodiment, the C peptide is a cycle structure consisting of KLARLLTC.

In one embodiment, the target nanoparticle is constructed by a conjugate of DSPE-PEG-C and the tumor target peptide.

In one embodiment, the tumor target aptamer comprises Ac aptamer (SEQ ID NO. 3: 5'CCAAGGCCTGCAAGG-GAACCAAGGACACAGTTTTTTTTTT3'), Eg aptamer (SEQ ID NO. 4: 5'TGCCGCTATAATGCACGGATT-TAATCGCCGTAGAAAAGCATGTCAAAGCCG3') or Ep aptamer (SEQ ID NO. 5: 5'CACTA-CAGAGGTTGCGTCTGTCCCACGTTGT-CATGGGGGGTTGGCCTG3').

In one embodiment, the target nanoparticle is constructed by a conjugate of DSPE-omPEG-Ac, DSPE-omPEG-Eg, or DSPE-omPEG-Ep and the tumor target aptamer.

In one embodiment, the immune cell target peptide comprises W peptide (SEQ ID NO. 6: WHRSYYTWNLNT), V peptide (SEQ ID NO. 7: VRARTR), A peptide (SEQ ID NO. 12: CAEYLR) or B peptide (SEQ ID NO. 13: N-acetyl PGP).

In one embodiment, the A peptide can target to EGFR.

In one embodiment, the B peptide can target to neutrophil.

In one embodiment, the target nanoparticle is constructed by a conjugate of DSPE-PEG-W, DSPE-PEG-V, DSPE-PEG-A or DSPE-PEG-B and the immune cell target peptide.

In one embodiment, the immune cell target aptamer comprises Al aptamer (SEQ ID NO. 8: 5'ACGGGCCACAT-CAACTCATTGATAGACAATGCGTC-CACTGCCCGTTTTTTTTTT3') or Ax aptamer (SEQ ID NO 9: 5'-GCGUGGUGUGAUCUAGAU-GUAUUGGCUGAUCCUAGUCAGGUACGC3').

In one embodiment, the target nanoparticle is constructed by a conjugate of DSPE-omPEG-Al, or DSPE-omPEG-Ax and the immune cell target aptamer.

In one embodiment, the endoplasmic reticulum target peptide comprises S peptide (SEQ ID NO. 10: SLLMWITQ) or O peptide (SEQ ID NO. 11: SIINFEKL).

In one embodiment, the target nanoparticle is constructed by a conjugate of DSPE-PEG-S or DSPE-PEG-O and the endoplasmic reticulum target peptide.

In one embodiment, the target nanoparticle size is about 150 nm with narrow size distribution.

The present invention further presents a method for treating a cancer in a subject, comprising administering an effective amount of target nanoparticle as mentioned before, comprising: a therapeutic agent, the therapeutic agent comprises ERS inducer and a nucleic acid immunomodulator.

In one embodiment, the cancer comprises pancreas, colon, or head and neck cancer.

In one perfect embodiment, the therapeutic agent further comprises an immunoadjuvant.

In one embodiment, the ERS inducer comprises CB-5083, NMS-873, DBeQ, CB-5339 or Gemcitabine.

In one embodiment, wherein the nuclear aptamer is selected from the group consisting of Apt for anti-programmed cell death ligand-1; anti-PD-L1 (P1), Apt for anti-programmed cell death protein-1; anti-PD-1($A_p$), anti-PD-L1/anti-cytotoxic T lymphocyte associated antigen-4; anti-CTLA-4(Apt(PIC4)), anti-lymphocyte activation gene 3; (LAG-3)Apt($A_{lag}$), and anti-T cell immunoglobulin and mucin domain-3 (TIM-3) Apt ($A_t$).

In one embodiment, the miRNA is a has-miR-21 inhibitor or a miRNA mimic, wherein the miRNA mimic is selected from the group consisting of has-miR-122-5p, has-miR-125b-5p, has-miR-136-5p, has-miR-139-5p, has-miR-142-5p, has-miR-200c-3p, and has-miR-320.

In one embodiment, the immunoadjuvant comprises resiquimod (R848, R), Imiquimod (R837), Vadimezan (dim-ethylxanthone acetic acid; DMXAA, ASA404), Indoximod (1-methyl-D-tryptophan, NLG-8189), DNase (DN), Lorla-tinib, Galunisertib (LY-2157299, G), SB-431542, Lan-raplenib, Reparixin (DF 1681Y) or T peptide (SEQ ID NO. 1: TEEEQQLY).

In one embodiment, the outer shell layer of the target nanoparticle is coating a tumor microenvironment acid-detachable polymer, the tumor microenvironment acid-de-tachable polymer is PEG-PGA or omPEG, it can enhance passive targeting of tumor sites by prolonging the systemic circulation time of nanoparticles in the blood and enhancing the penetration and retention effect (EPR).

In one embodiment, the target nanoparticle is de-coated of tumor microenvironment acid-detachable polymer (PGA-PEG or omPEG) on the outer shell layer at pH 6.0 environ-ment. This allows the cationic target peptide or the anionic target aptamer to be exposed and bind to receptor or other targets of EGFR, VEGFR, CXCR4, CD44, PD-1, PD-L1 or neutrophil on tumors, macrophages, T cells or immune cells such as neutrophils. The goal is to increase the uptake of the nanoparticle by cancer cells and enable it to reach the endoplasmic reticulum or cytoplasm.

BRIEF DESCRIPTION OF THE DRAWINGS

FIGS. 2-9 show the chemical characteristics of CB, miR or R loaded on nanoparticles of endoplasmic reticulum and immune cell targets of the present invention.

FIG. 2 shows the NMR spectrum of PGA-PEG, and the structure was verified by NMR.

FIGS. 3-5 show the MALDI-TOF mass spectrum of DSPE-PEG-C. DSPE-PEG-S. and DSPE-PEG-W. The DSPE-PEG-C. DSPE-PEG-S. and DSPE-PEG-W were suc-cessfully synthesized and the structure was verified by MALDI-TOF mass spectrum.

FIG. 6 shows the TEM images of CB/SLN-CSW, CB+miR/SLN-CSW, CB+miR+R/SLN-CSW and the nan-oparticles size and zeta potential.

FIG. 7 shows the TEM images of CB/SLN-CSW, CB+miR/SLN-CSW, CB+miR+R/SLN-CSW and the nan-oparticle size and zeta potential in different pH environment.

FIG. 9A shows detection of intracellular accumulation of DiI-CB, miR-, and/or R-loaded formulations in Panc-02 cells for 24 h by flow cytometry. FIG. 9B shows evaluation of fluorescence intensity of CB, FAM-miR-, and/or R-loaded formulations in Panc-02 cells for 24 h by flow cytometry.

In FIG. 16, panel B shows the result of HMGB1 secretion by ELISA kits.

In FIG. 16, panel C shows the result of extracellular ATP release by ATP Detection Assay Kit.

In FIG. 24, panel B shows optical images of Panc-02-bearing mice after completing 14-day therapy.

In FIG. 24, panel C shows TUNEL images (up panels) of Panc-02-bearing mice. In vivo apoptotic cells in tumor tissues were stained green and the nuclei were stained blue by Hoechst (middle panels). Scale bar, 200 μm. Histological photomicrographs (down panels) of the tumor sections stained by hematoxylin and eosin (H&E). Scale Bar: 200 μm.

DETAILED DESCRIPTION OF THE INVENTION

In order to solve the above-mentioned problems, the present invention provides a novel tumor pH-shiftable nanoparticles and use thereof.

Definition

Imine-O'-methyl polyethylene glycol, hereinafter referred to as omPEG.

The ERS inducer in present invention means a drug that can induce ERS, including but not limited to CB-5083 (hereinafter referred to as: CB), NMS-873 (hereinafter referred to as: NM), DBeQ, CB-5339 or gemcitabine (hereinafter referred to as: Gem).

In one embodiment, the present invention involves mixing ERS inducer which is not soluble in water, with immunoadjuvant and a surfactant. This allows the ERS inducer and immunoadjuvant to dissolve in a vehicle that contains a surfactant, which is then combined with the nanoparticle. This resolves the issue of the ERS inducers' insolubility in water and enables them to be effectively combined with and encapsulated in the nanoparticles. Additionally, the pH dissociation shell of the nanoparticle along with the tumor-targeted peptide or tumor-targeted aptamer targets the tumor environment. The endoplasmic reticulum target peptide is then used to ensure the accurate delivery of the ERS inducer to the endoplasmic reticulum, preventing the drug from being lost or affecting normal cells or organelles prematurely.

Example 1. Synthesis of pH-Sensitive Polymer (PGA-PEG)

As shown in FIGS. 2-5, first of all. 1 ml of sodium tetraborate was mixed with PGA, methoxy PEG amine (mPEG-NH2), and N-hydroxy succinimide (NHS). The mixture was then incubated at room temperature for an overnight reaction with 1-Ethyl-3-[3-dimethylaminopropyl]-carbodiimide hydrochloride (EDC). Then, the mixture was lyophilized after being dialyzed with a 5 kDa cut-off membrane against PBS. Finally, the conjugation of PGA-PEG was ascertained by 1H NMR.

Example 2. Synthesis of Lipid-Conjugated Peptides

C peptide. S peptide or W peptide and Lipid mixture were mixed. The solution was then combined with triethylamine (TEA), and the mixture underwent an overnight reaction at room temperature and avoided from light. After dialyzed with a 5 KDa cut-off membrane against PBS, the mixture was lyophilized. The conjugation of lipid and peptide was verified using MALDI-TOF Mass Spectrometer.

Example 3. Preparation of Peptide-Conjugated Solid Lipid Nanoparticles (CB+miR+R/SLN-CSW) and pH-Sensitive Peptide-Conjugated Solid Lipid Nanoparticles (CB+miR+R/PGA-SLN-CSW)

Monostearin, cholesterol. DOTAP. Lipid-peptide, and CB and R were first stirred at 50° C. in ethanol. After mixed well, the surfactant was then added drop by drop into the mixture solution and stirred. Then, miR was added to the solution by pipetting at room temperature. Finally, the formulation of CB+miR+R/SLN-CSW was successfully synthesized. To synthesized CB+miR+R/PGA-SLN-CSW, 0.1% PGA-PEG was added into CB+miR+R/SLN-CSW at room temperature.

Example 4. Characterizations of SLN Formulations

Figure 1:
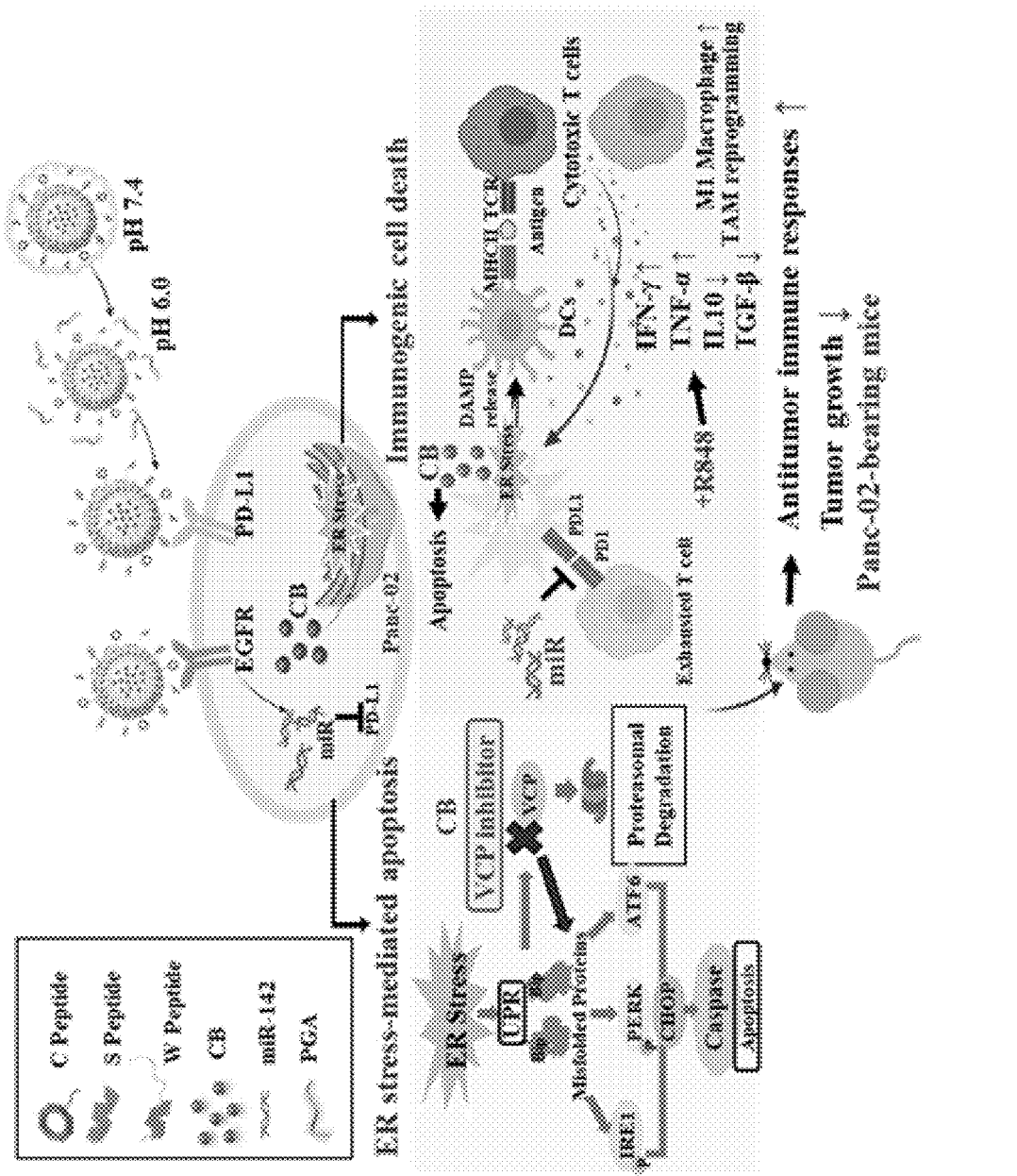
FIG. 1 shows the target nanoparticle possesses character-istics of targeting to EGFR. PD-L1, and endoplasmic reticu-lum (ER), and combinatorial therapy of ERS inducer, miRNA, and immunoadjuvant to provide simultaneous inhi-bition of progression and immune escape of tumors and tumor-associated macrophages (TAMs) for ameliorating immune activation and memory, antitumor efficacy, and safety in PDAC treatment.
Figure 2:
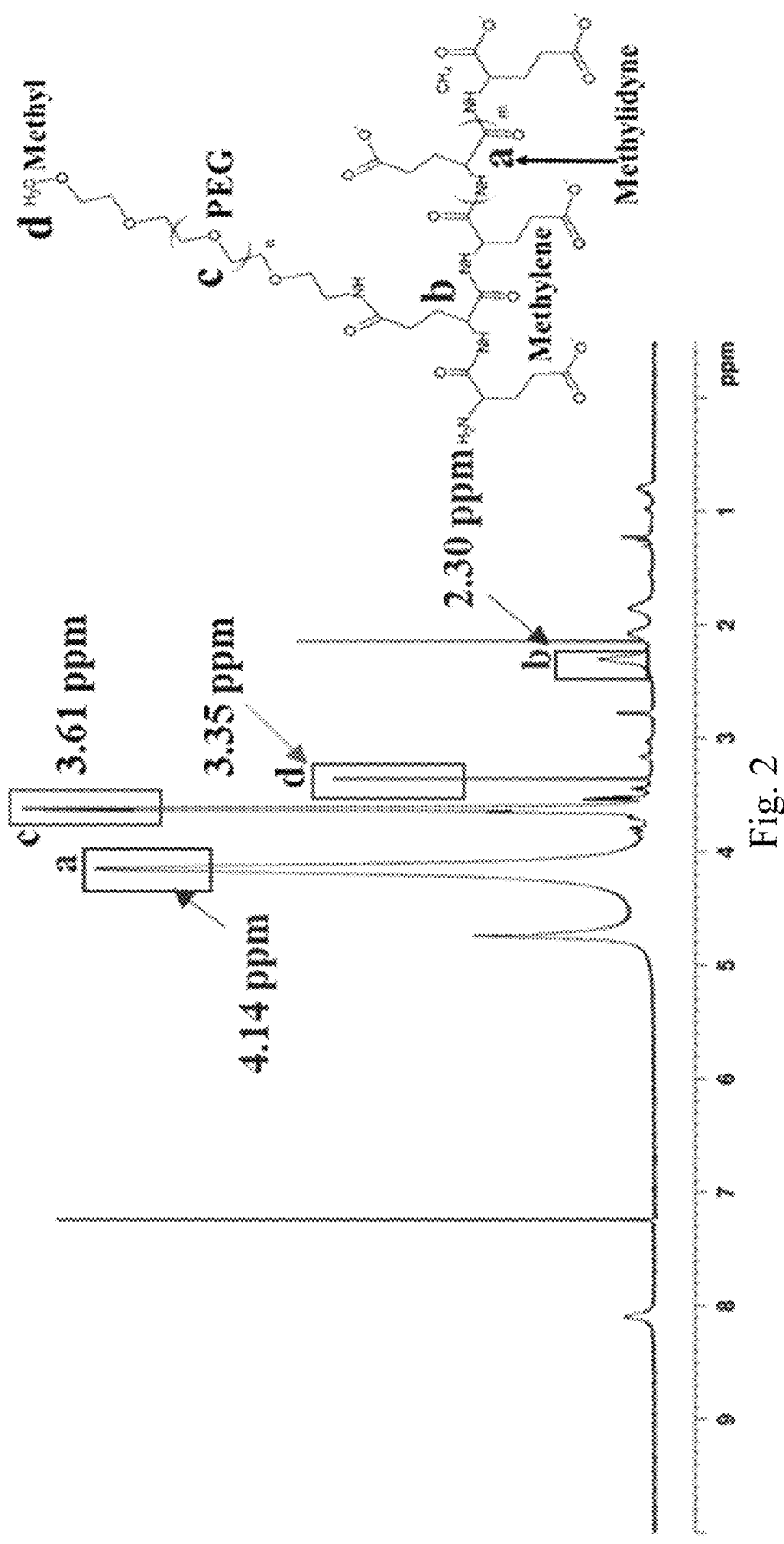
Figure 3:
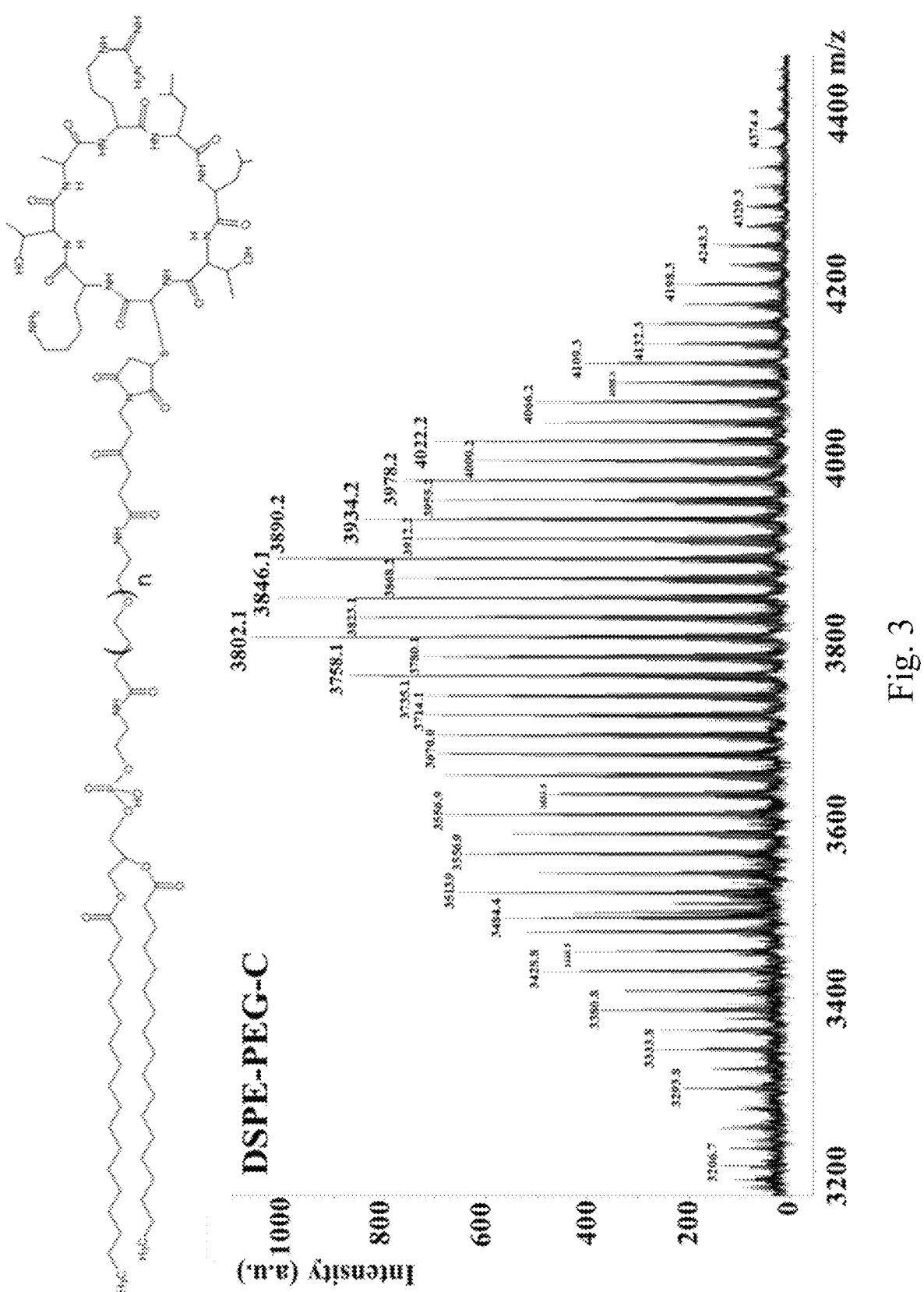
Figure 4:
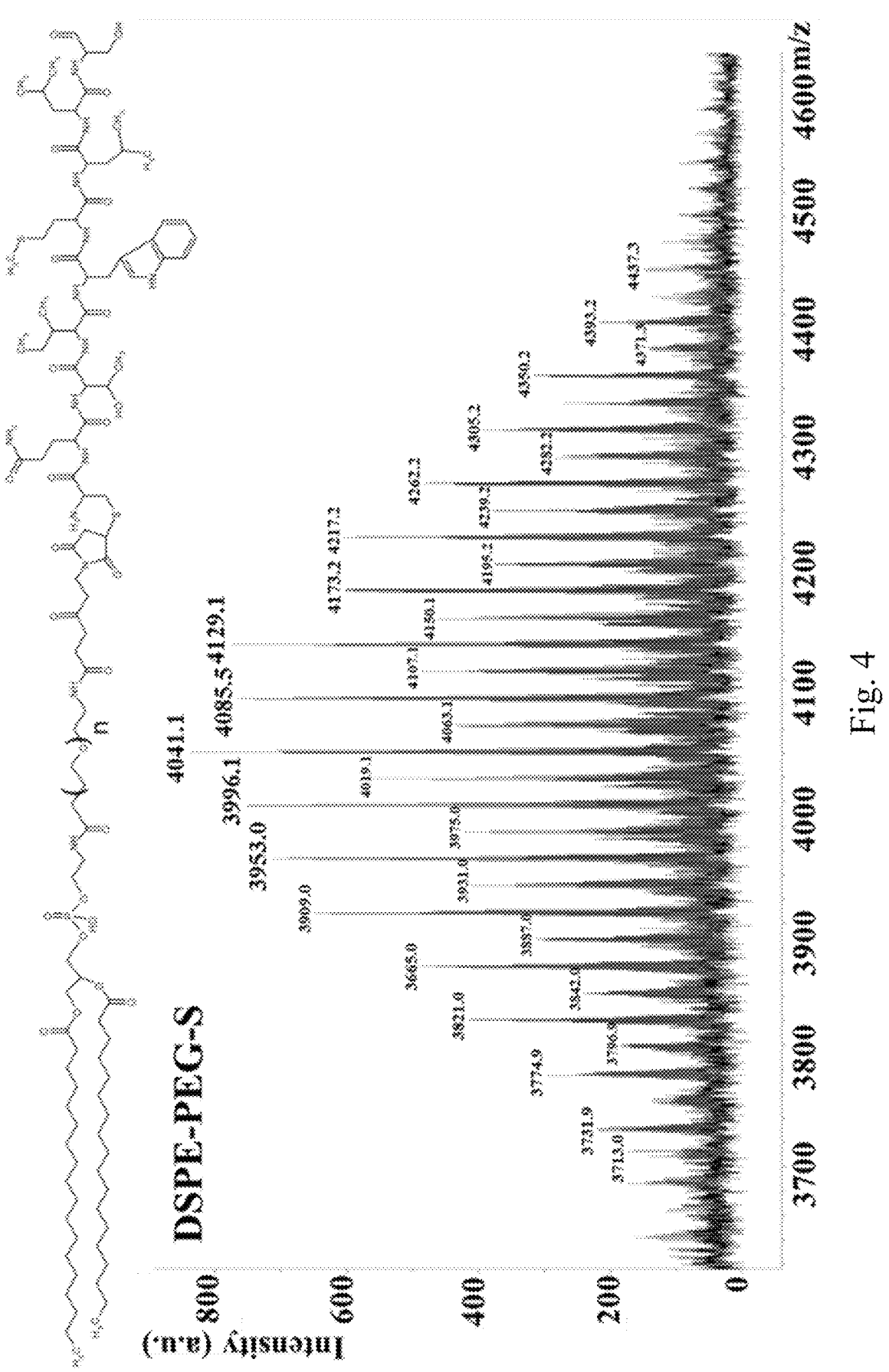
Figure 5:
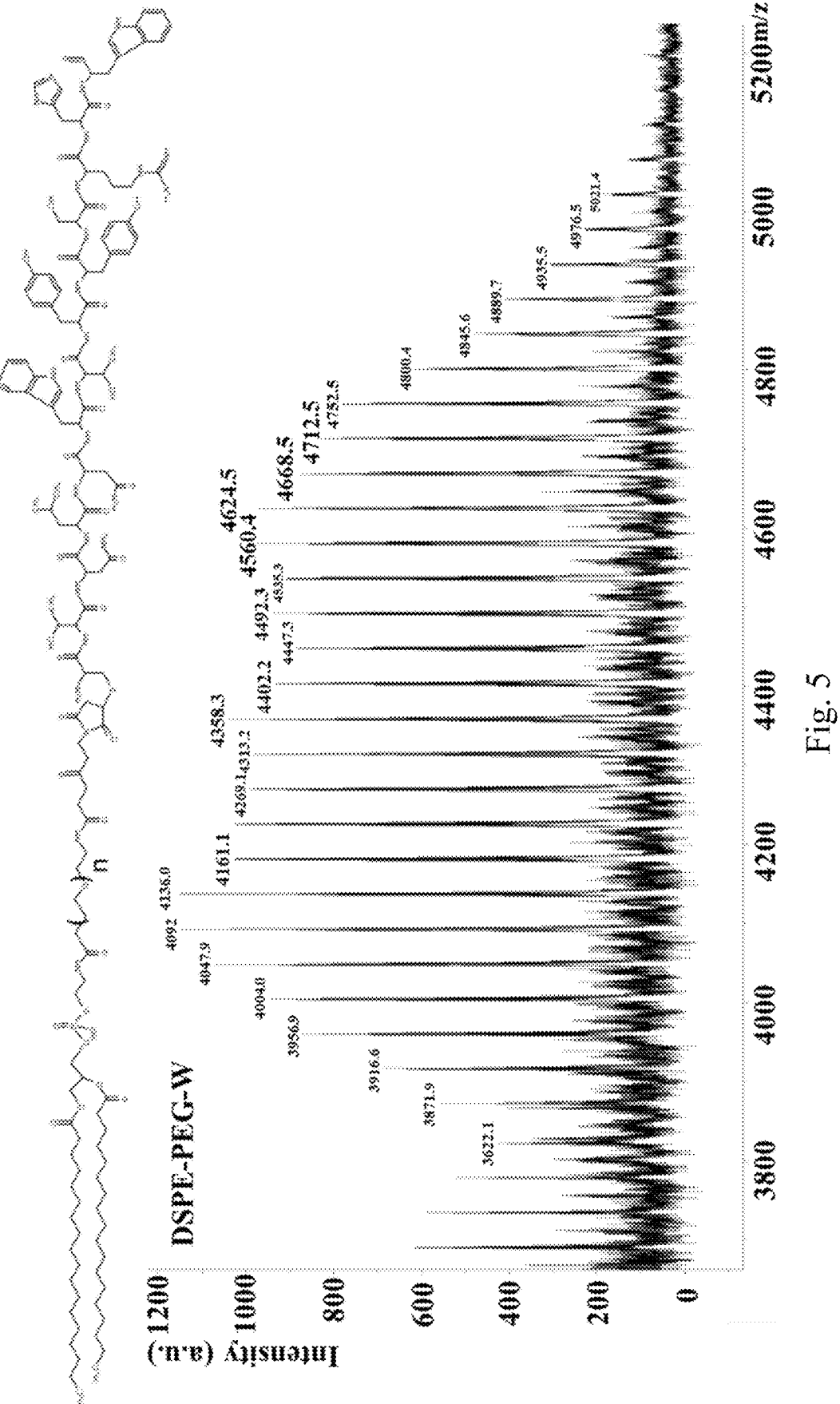
Figure 6:
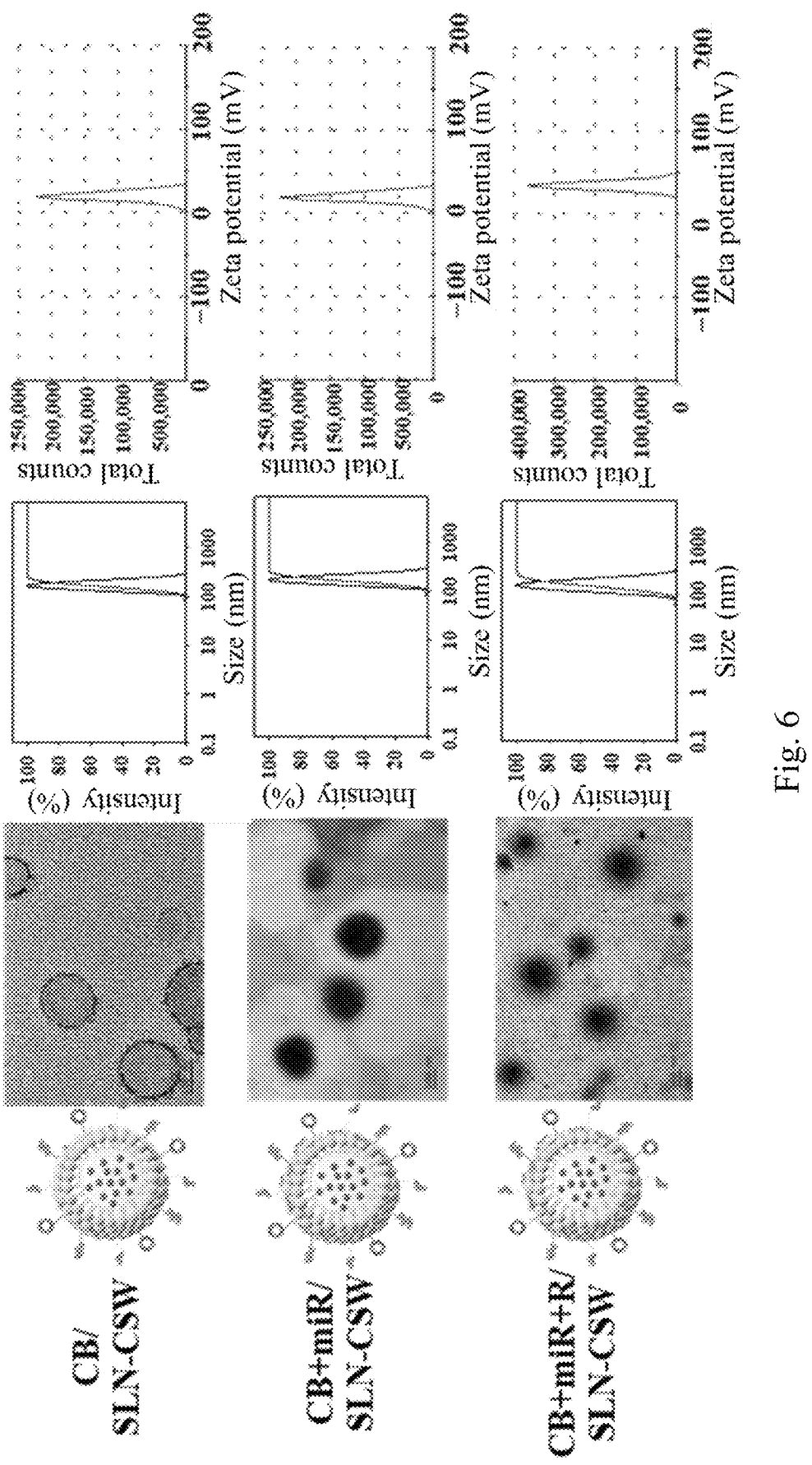
Figure 7:
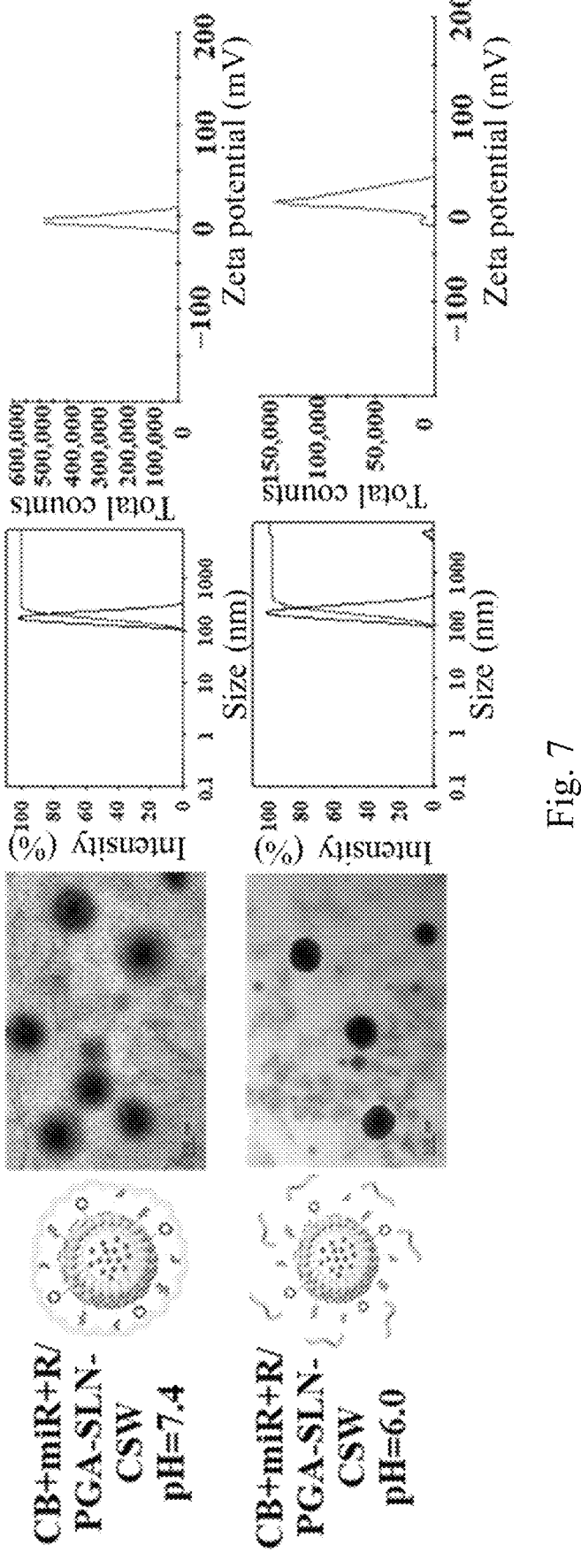
Figure 8A:
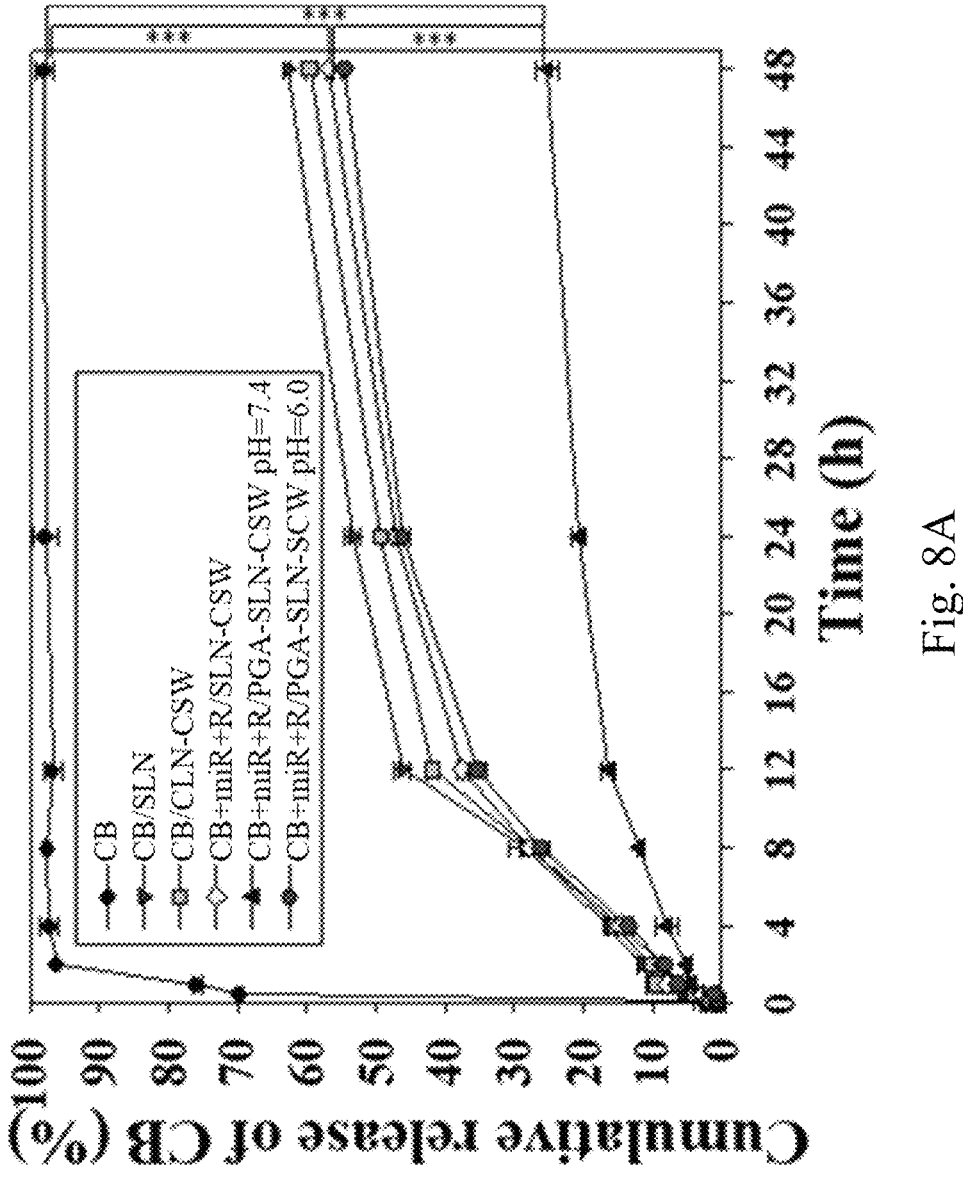
FIGS. 8A-8B shows in vitro release profiles of CB and miR from SLN-CSW in different pH conditions of different formulations.
Figure 8B:
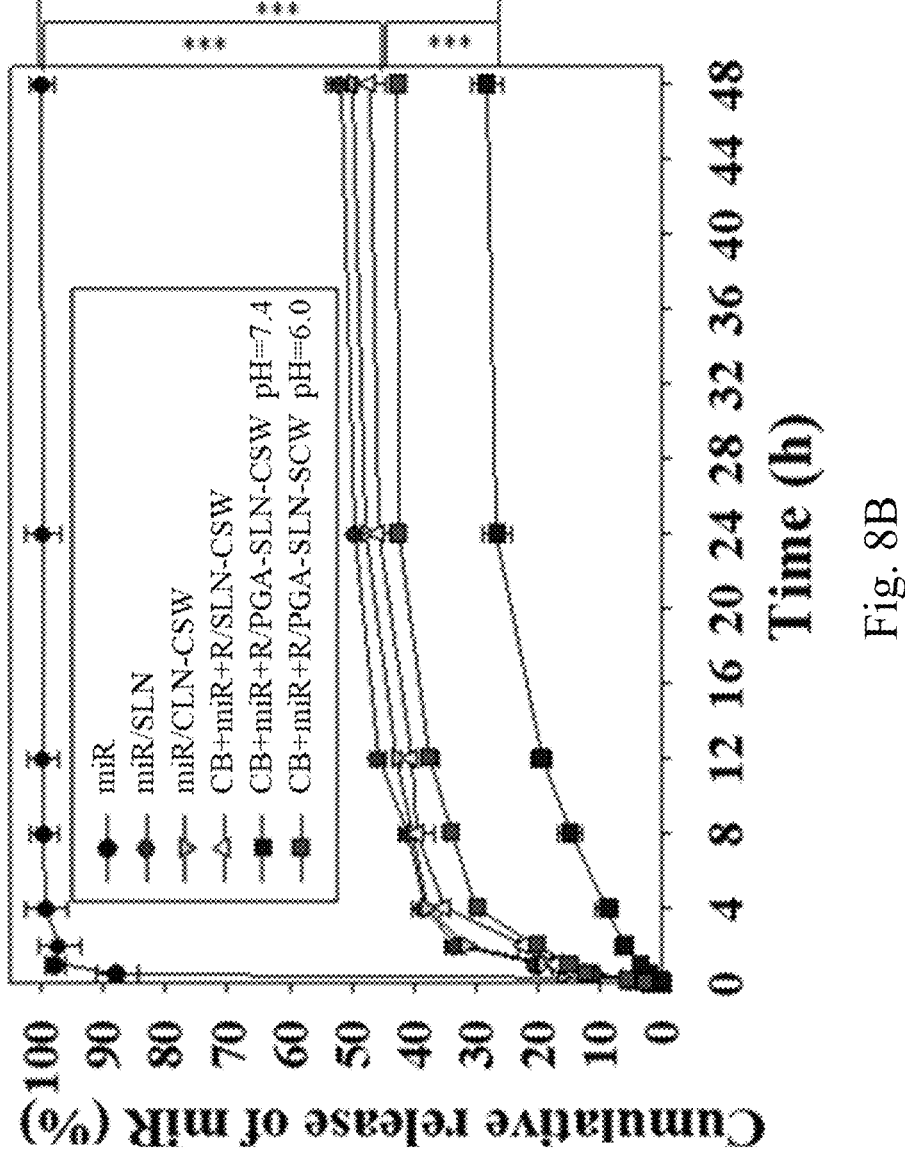

The size distribution, polydispersity index (PDI) and zeta potential of different SLN formulations were measured via a Zetasizer Nano-ZS particle size analyzer. The result is shown in FIG. 6.

The Morphology of different SLN formulations were observed by Transmission Electron Microscope.

Example 5. Encapsulation Efficiency (EE %) and Drug Loading Capacity (DL %)

The ultracentrifuge filter was used to centrifuge a dispersion of CB-, miR-, and/or R-containing nanoparticles. The obtained nanoparticles were then broken down with 0.5% Triton X 100 and centrifuged. The filtrate and the extracted CB- or miR were collected and examined using a UV/VIS Spectrophotometer and a NanoDrop, respectively.

Each sample was detected in triplicate. EE % or DL % of CB or miR in SLN-CSW were calculated by the following formula.

$$EE\% = \left[ (W_e - W_f)/W_e \right] \times 100\% \tag{1}$$

$$DL\% = \left[ (We - Wf)/Wt \right] \times 100\% \tag{2}$$

Wherein, We is the weight of added CB or miR, Wf is the weight of CB or miR in the filtrate, and Wt is the total nanoparticle weight.

Example 6. The pH-Sensitive Properties Test

To examine the pH-responsive changes of size and zeta potential on CB+miR+R/PGA-SLN-CSW, CB+miR+R/PGA-SLN-CSW were mixed with D.D. water, and the pH value was adjusted to 7.4 or 6.0. Then, the size and zeta potential of nanoparticles were measured by Dynamic Light Scattering (DLS) analyzer.

Furthermore, the pH-sensitive drug release property was measured. The nanoparticles were incubated with PBS buffer with 2% Tween 80 at pH7.4 and pH6.0. The concentration of released CB or miR from different SLN formulations was analyzed by UV/VIS Spectrophotometer and NanoDrop at different time points, respectively.

Example 7. Cell Lines

Mouse pancreatic ductal adenocarcinoma cells, Panc-02 cells, were cultured in RPMI/1640 medium supplemented with 10% FBS and 1% penicillin/streptomycin/glutamine (PSG). Mouse macrophage cells, Raw 264.7, were cultured in DMEM medium supplemented with 10% FBS, 100 IU/mL penicillin, 0.1 mg/mL streptomycin, 0.25 lg/mL amphotericin B (P.S.A), and 1% L-glutamine.

Mouse pancreatic beta-cell line, NIT-1 cells, were cultured in Ham's F12K medium with 2 mM L-glutamine adjusted to contain 1.5 g/L sodium bicarbonate and 10% heat-inactivated dialyzed fetal bovine serum.

Example 8. Cellular Uptake

Figure 9A:
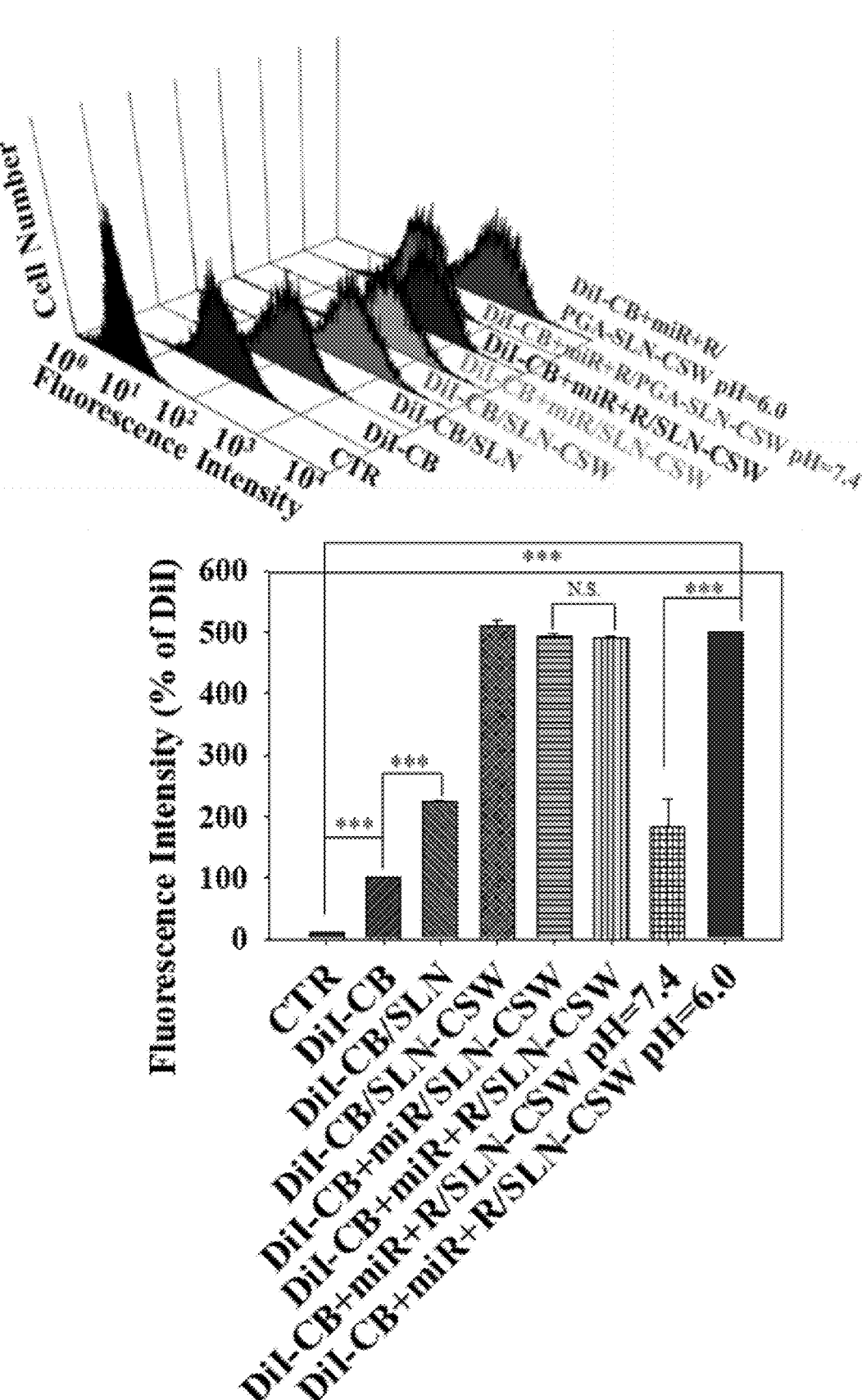
FIGS. 9A-9B shows cellular uptake, intracellular distri-bution, and cytotoxicity of different formulations at the equivalent concentrations of CB (IC30: 210 nM), miR (100 nM), and R848 (1.5 M).
Figure 9B:
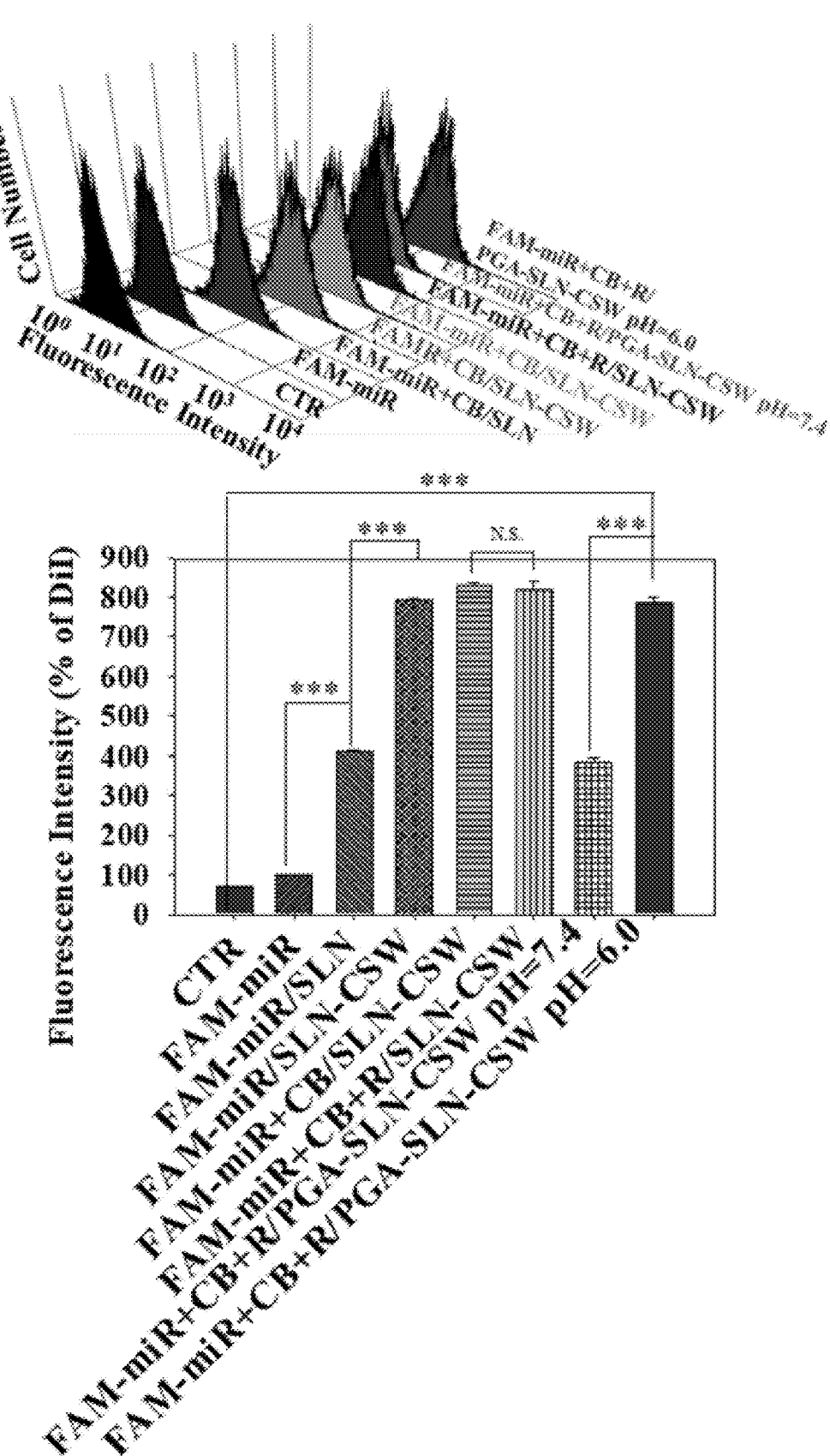

Panc-02 were seeded in 12-well plates. DiI-CB and several DiI-loaded SLNs formulations were used to treat the cells. After incubating 24 h. cells were trypsinized, collected, washed and suspended in 1 mL PBS in dark. Flow cytometer was used to quantify the fluorescence intensity of DiI-CB taken up by cells. The result is shown in FIGS. 9A-9B.

Example 9. Transfection Efficacy

Panc-02 were seeded in 12-well plates. FAM-miR and several FAM-miR-loaded SLNs formulations were used to treat the cells. After incubating 24 h. cells were trypsinized, collected, washed and suspended in 1 mL PBS in dark. Flow cytometer was used to quantify the fluorescence intensity of FAM-miR taken up by cells. The result is shown in FIGS. 9A-9B.

Example 10. Intracellular Localization Studies

Figure 10A:
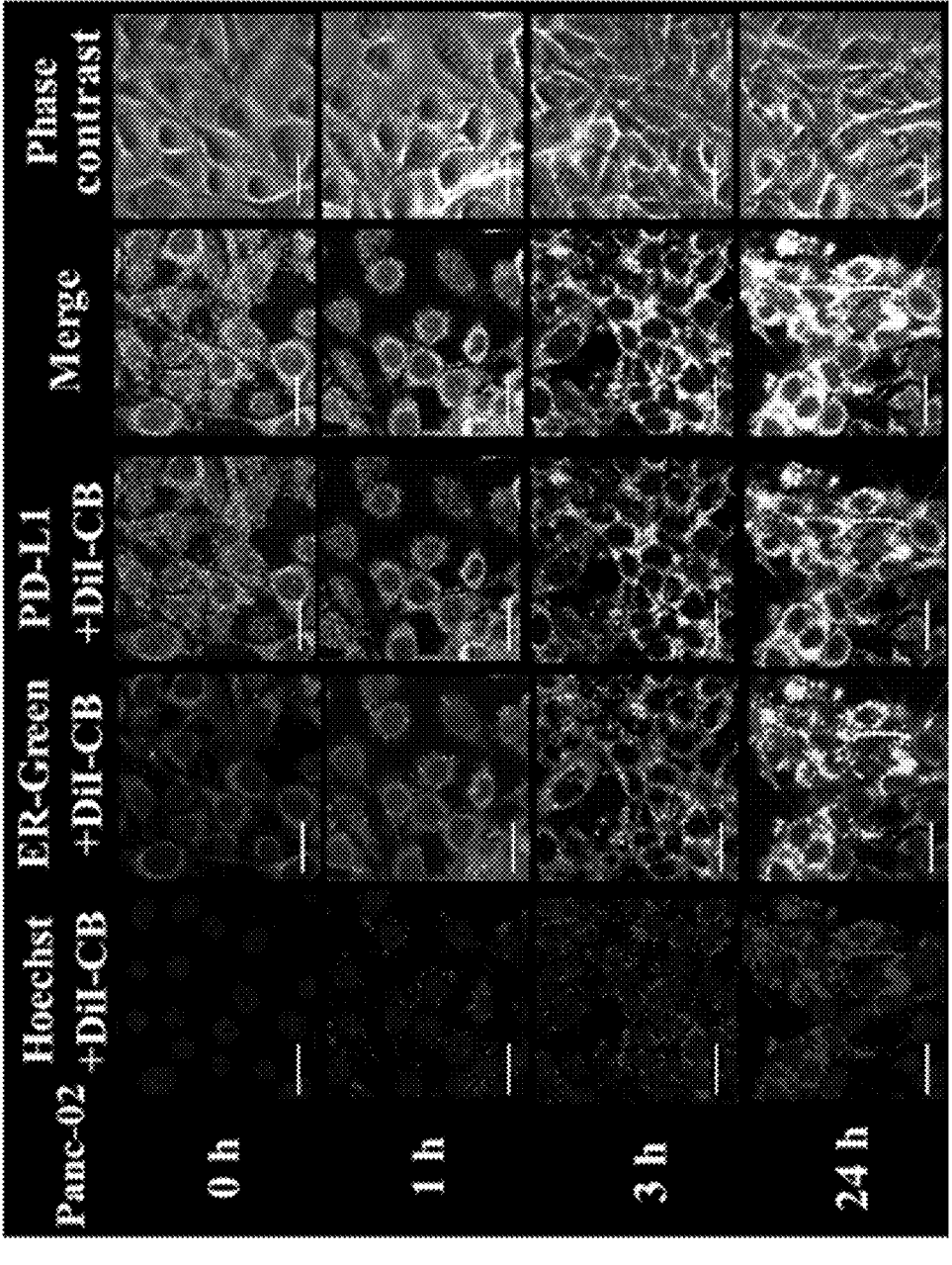
FIG. 10A shows PD-L1 targeting and subcellular localization of DiI-CB+miR+R/SLN-CSW in Panc-02 cells for 1, 3, and 24 h as overserved by CLSM.
Figure 10B:
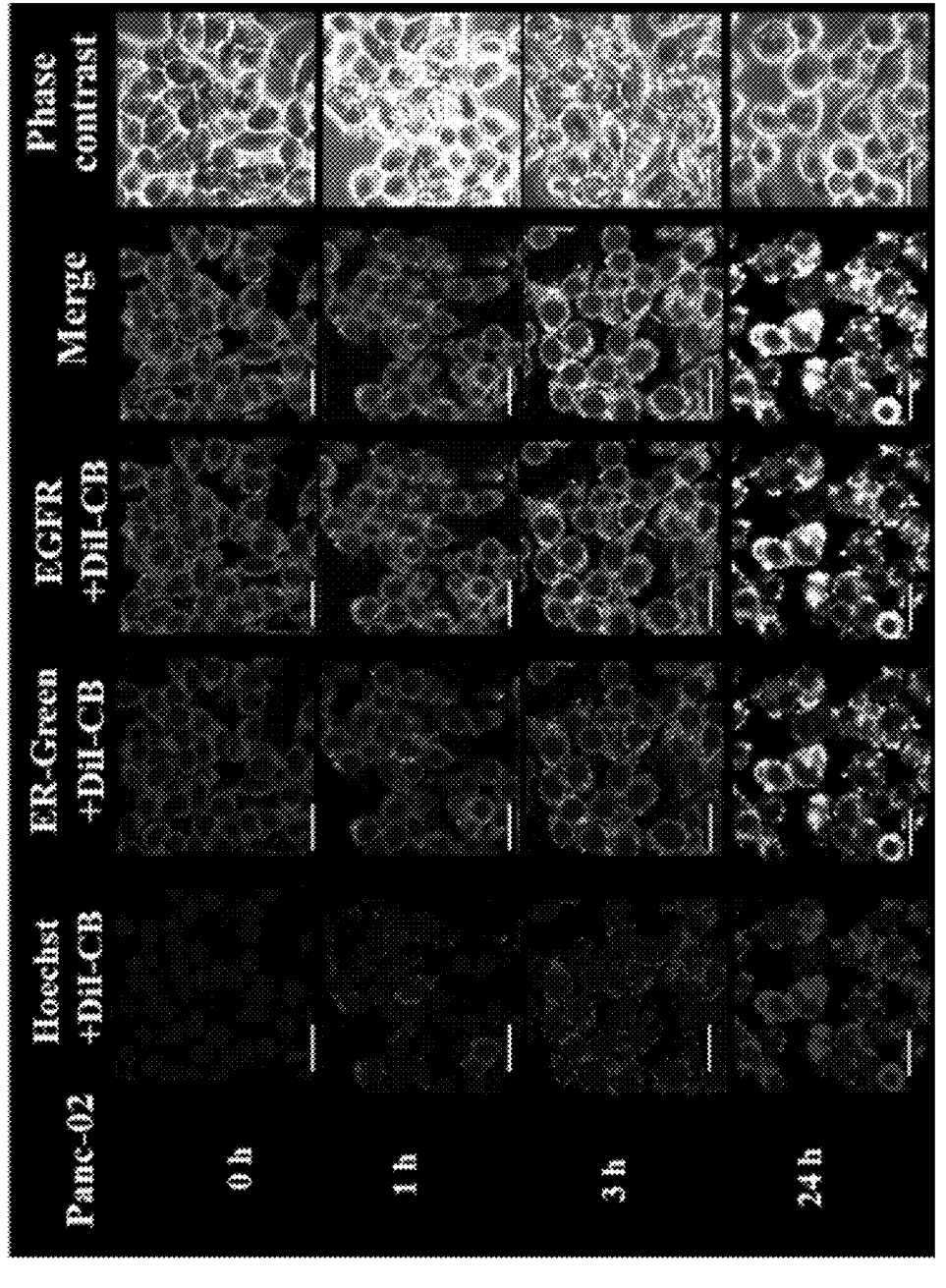
FIG. 10B shows EGFR-targeting and intracellular distribution of DiI-CB+miR+R/SLN-CSW in Panc-02 cells for 1, 3, and 24 h as imaged by CLSM.

Panc-02 cells were seeded in 6-well plates. DiI-CB and several DiI-loaded SLNs formulations were used to treat the cells at different time points. After treatment, the nucleus and endoplasmic reticulum was stained by ER staining kit. Then, the cells were fixed in 4% paraformaldehyde. After blocking with fetal bovine serum. EGFR or PD-L1 were tagged with primary antibody. Finally, the primary antibody was labeled with the Cy5 secondary antibody. Images were taken by a confocal laser scanning microscope. The result is shown in FIGS. 10A-10B.

Example 11. Hemolysis Analysis

Rat whole blood was collected and centrifuged. After centrifuged, the supernatant was removed, and the pallet was rinsed by PBS until the supernatant was clear. The tubes containing 1 mL of red blood cells were treated with various formulations and 0.5% Triton X-100 (positive control). The mixture was incubated at 37° C. for 24 h. The hemoglobin containing in RBCs was then reacted at room temperature with Drabkin's reagent. The concentration of the final mixture was determined using an ELISA reader.

Example 12. Cell Viability Assay: SRB Assay and Synergism Test

Figure 11A:
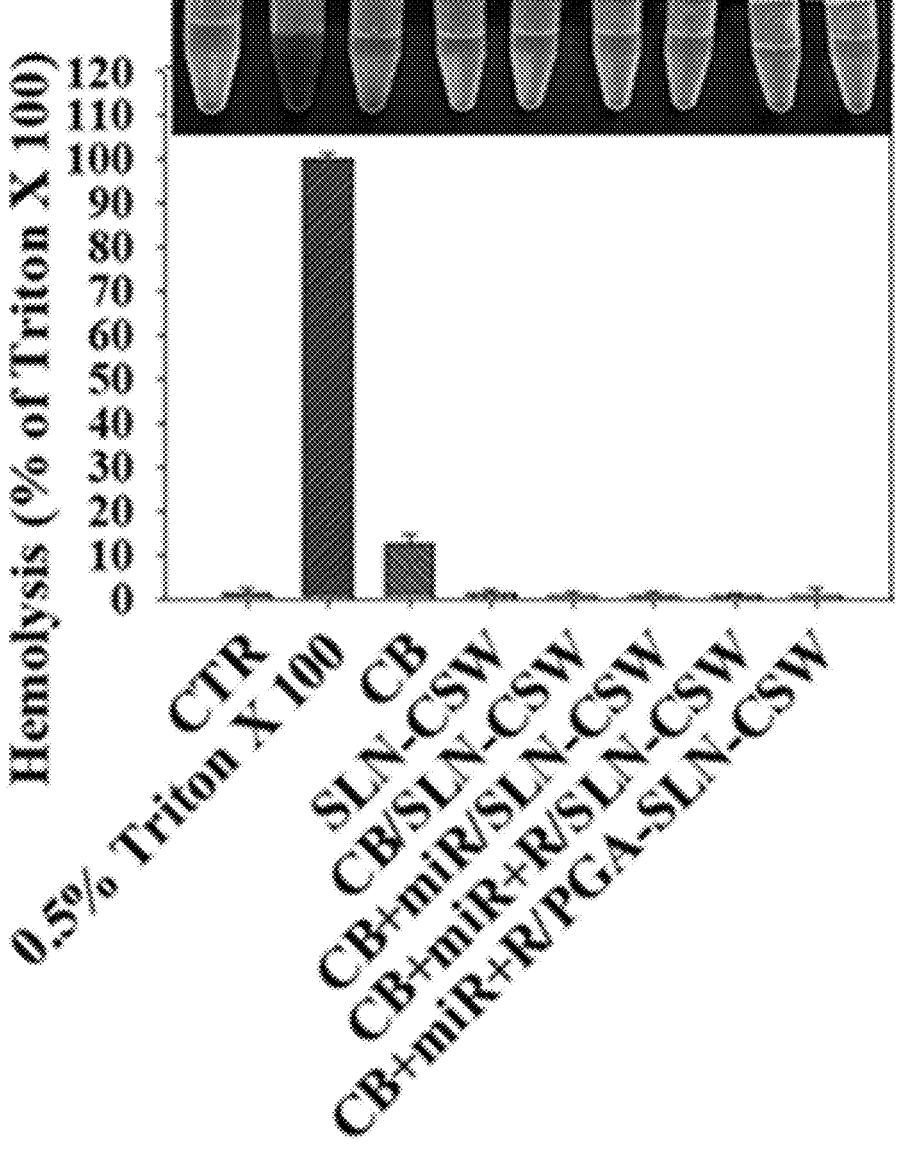
FIG. 11A shows Hemolysis effect (up panel) of various formulations on rat red blood cells (RBCs). Relative hemoglobin release % from rat RBCs were calculated (down panel).
Figure 11B:
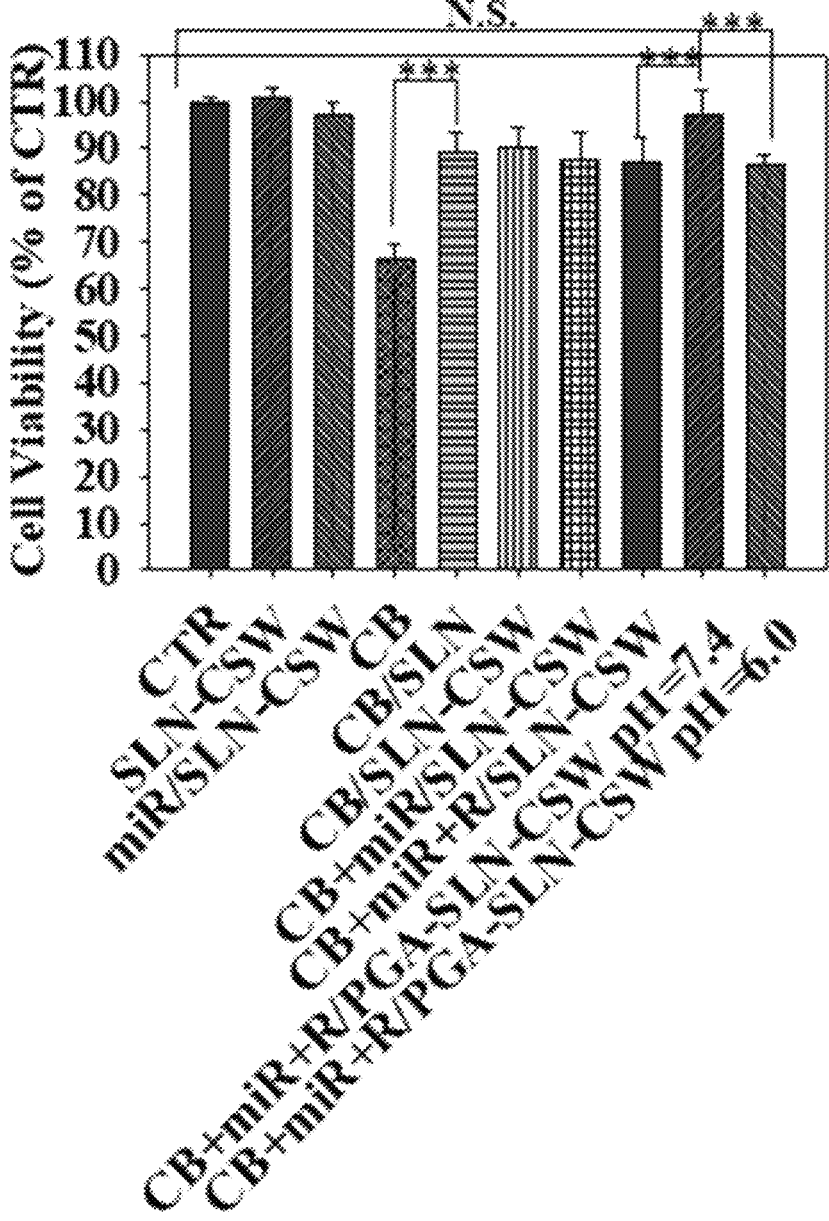
FIG. 11B shows the Cytotoxicity of different formulations on NIT-1 cells for 24 h, and the cell viability as determined by sulforhodamine B assay (statistical significance at $p < 0.05$; $p < 0.01$; *$p < 0.001$).
Figure 11C:
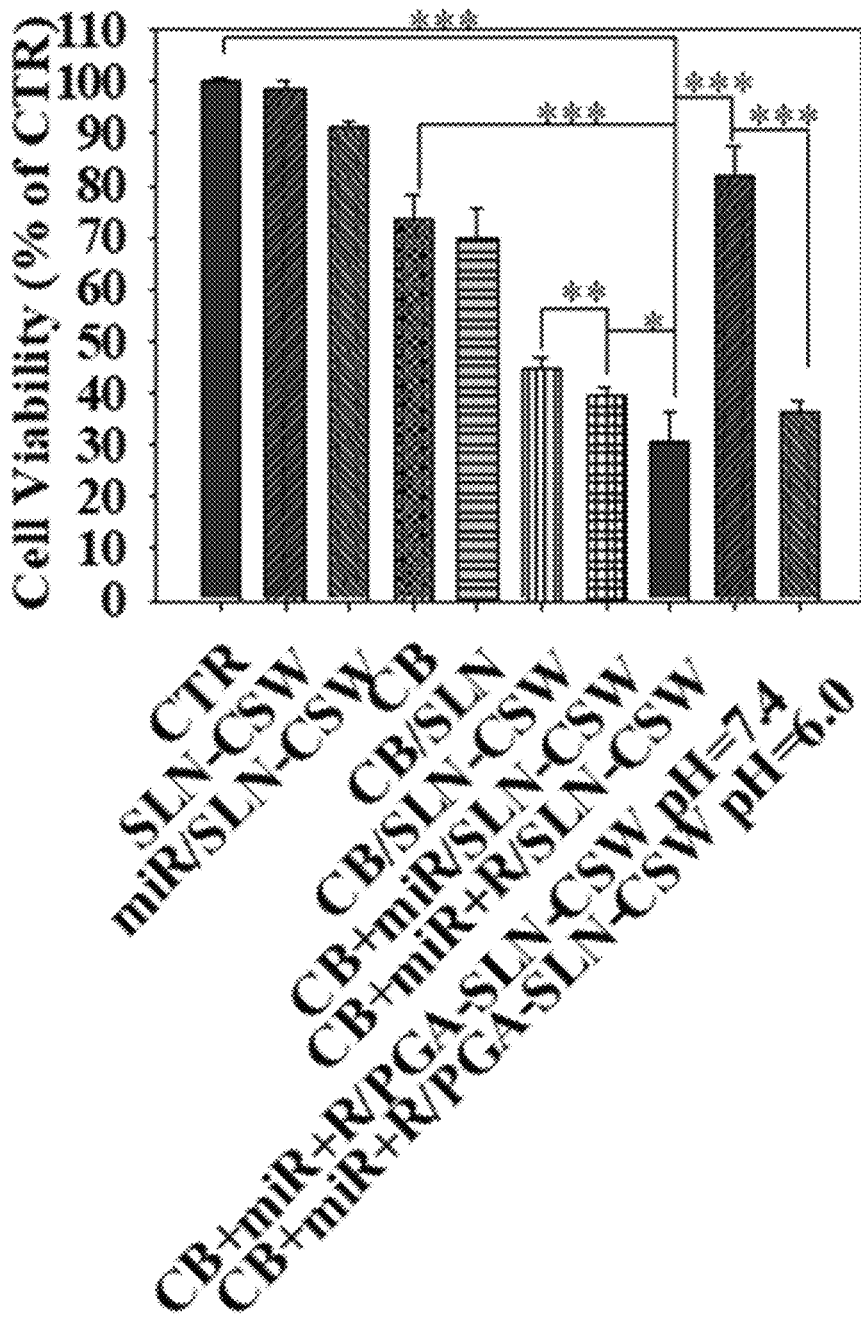
FIG. 11C shows the Cytotoxicity of different formulations on Panc-02 cells for 24 h, and the cell viability as determined by sulforhodamine B assay (statistical significance at $p < 0.05$; $p < 0.01$; *$p < 0.001$).
Figure 12A:
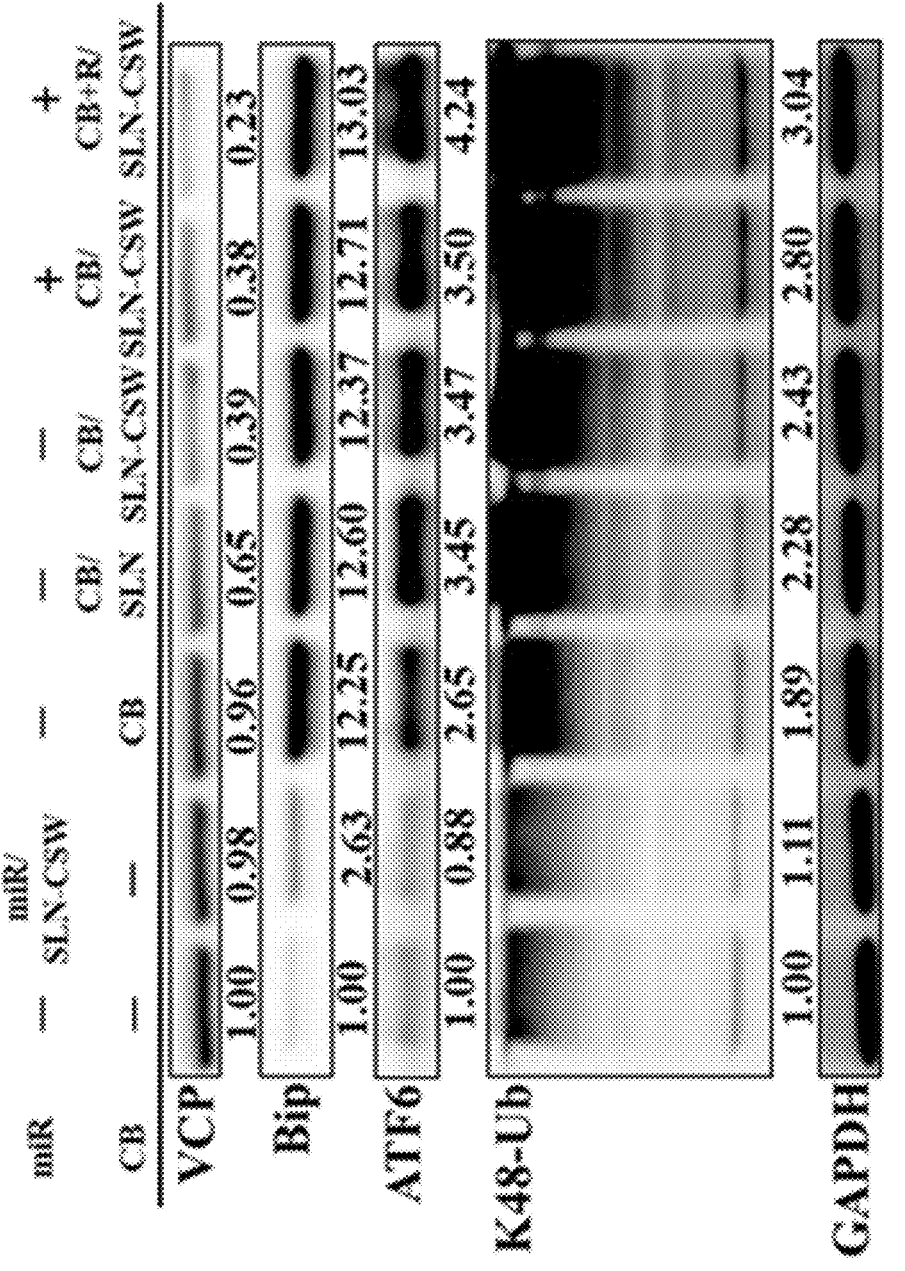
FIG. 12A shows effects of various formulations composed of CB (210 nM), miR (100 nM), and/or R848 (1.5 μM) on VCP/ATF6 pathways of ER-stress related pathways after treatment for 24 h on Panc-02 cells.
Figure 12B:
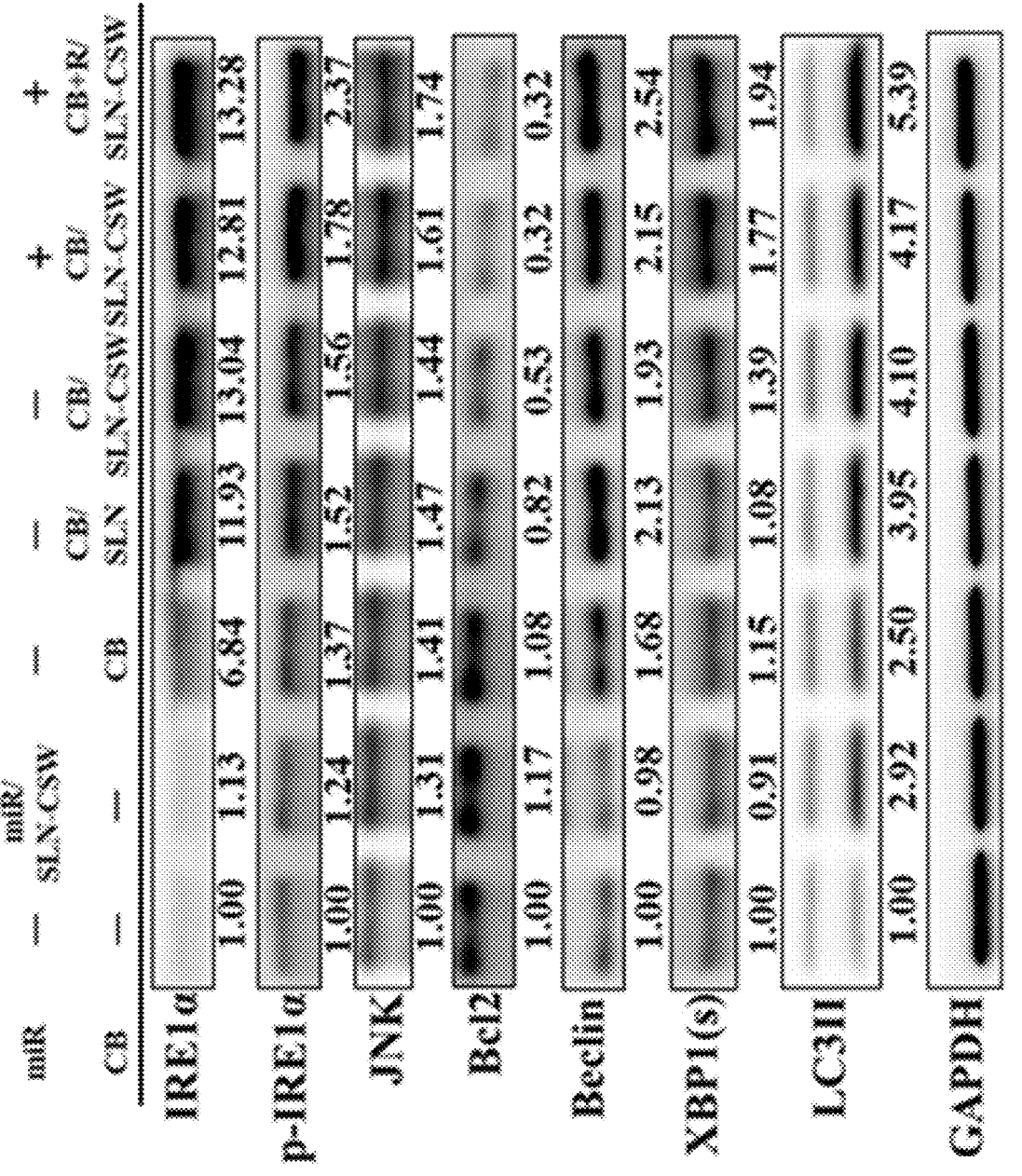
FIG. 12B shows effects of various formulations composed of CB (210 nM), miR (100 nM), and/or R848 (1.5 μM) on IRE1α/Beclin/XBP1/LC3 pathway of ER-stress related pathways after treatment for 24 h on Panc-02 cells.

Panc-02 cells or NIT-cells were seeded in 96-well plates. Cells were treated with various miR or CB-loaded SLNs formulations. TCA was used to fix the cells after treatment. The wells were then stained with sulforhodamine B (SRB) and rapidly rinsed with acetic acid. Following air drying. Tris base was added to each well, and the plates were examined using an ELISA reader. The result is shown in FIGS. 11A-11C.

Cell viability (%)=(The absorbance value of treated cells)(The absorbance value of untreated cells)× 100

Furthermore, cells were treated with miR or CB/SLN-CSW or CB+miR/SLN-CSW at different concentrations to examine the synergistic impact of combine therapy, and the combination index was calculated using CompuSyn software with results of cell viability.

Example 13. Western Blot

Panc-02 cells were seeded in 6-cm dishes. Different miR or CB-loaded SLNs formulations and the combined treatment were used to treat the cells. After treatment, protein from the cells was extracted using RIPA and detected using the BCA protein assay. SDS-PAGE was used to separate protein samples, which were then transferred to PVDF membranes. Non-specific binding sites were blocked with 5% milk, the membranes were then incubated with the primary antibody overnight. The membranes were detected using electrochemiluminescence detection reagent (ECL) after conjugation with horseradish peroxidase (HRP)-conjugated immunoglobulin G (Ig G), and the images were taken by Luminescence Imaging System.

The protein expression levels of different pathways (VCP/ ATF6, IRE1α/Beclin/XBP1/LC, PERK/eIF2α/ATF4/ CHOP/Casp) affected by treating cells with nanoparticles of different formulations were evaluated using Western blotting. The protein expression levels in each cell were assessed, and the results are shown in FIGS. 12A-13A.

Example 14. Measurement of Apoptosis

Figure 13A:
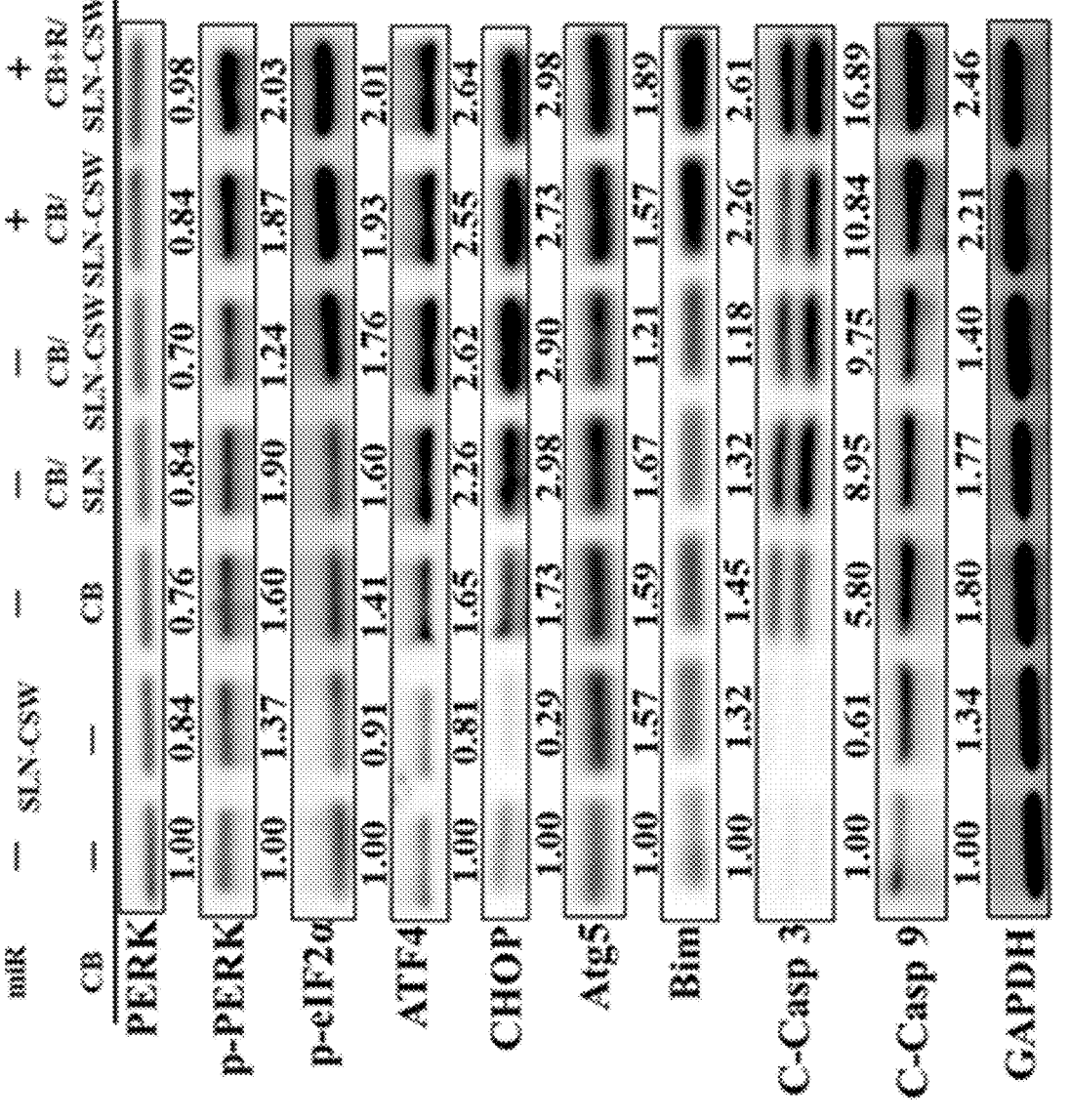
FIG. 13A shows effects of various formulations composed of CB (210 nM), miR (100 nM), and/or R848 (1.5 μM) on PERK/eIF2α/ATF4/CHOP/Caspase (Casp) pathway of ER-stress related pathways after treatment for 24 h on Panc-02 cells.
Figure 13B:
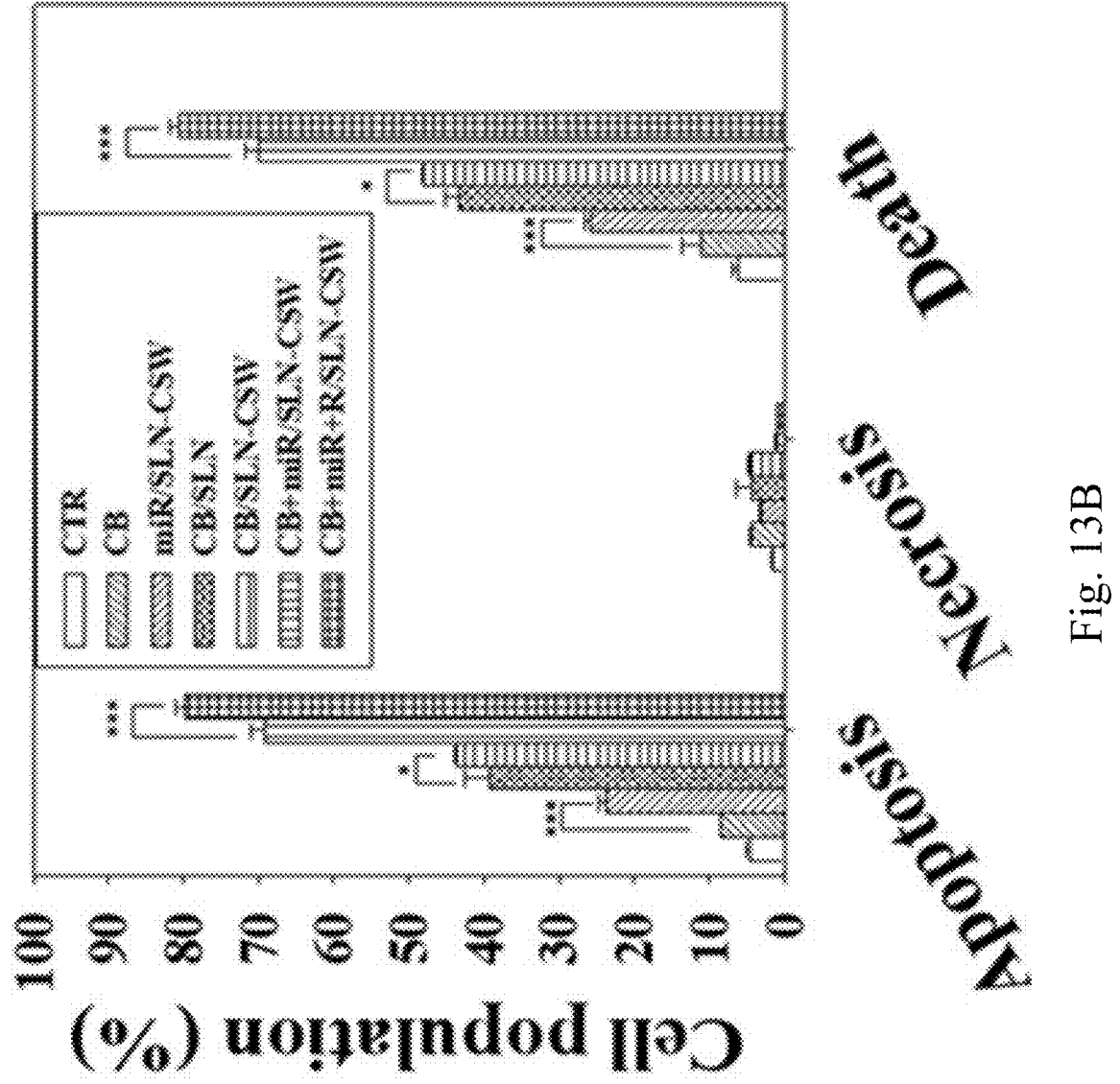
FIG. 13B shows the result of relative death percentages by Annexin V/P1 assay using a flow cytometer.
Figure 14A:
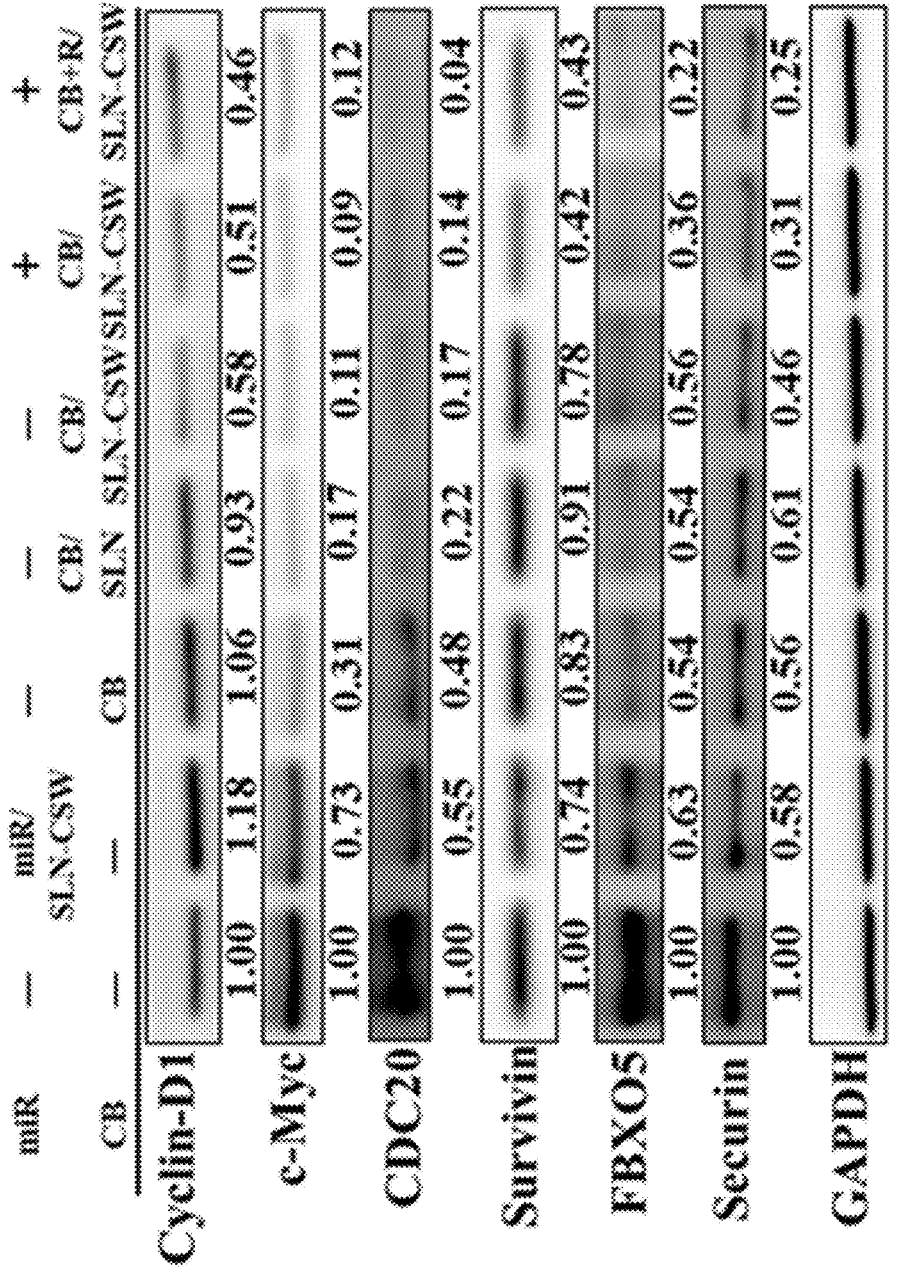
FIG. 14A shows effects of various formulations on cell cycle oncoproteins.
Figure 14B:
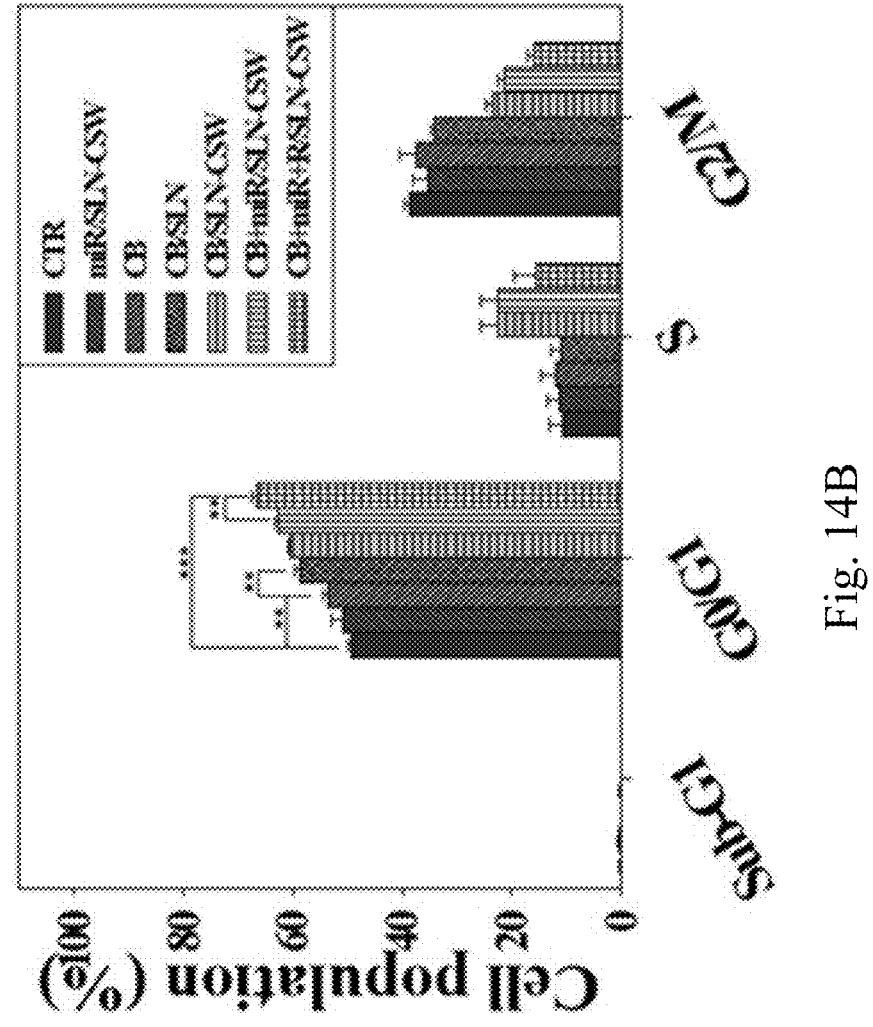
FIG. 14B shows relative % of cell cycle phase distribution in Panc-02 cell after various treatments.

Panc-02 cells were seeded in 12-well plates. Different miR or CB-loaded SLNs formulations and the combined treatment were used to treat the cells. After 24 h treatment, cells were trypsinized, collected and stained with Annexin V FITC Apoptosis detection kit in the dark. The total percentage of surviving, apoptotic, and necrotic cells was detected through Flow cytometer. The results are shown in FIG. 13B

Example 15. Migration Assay

Figure 15A:
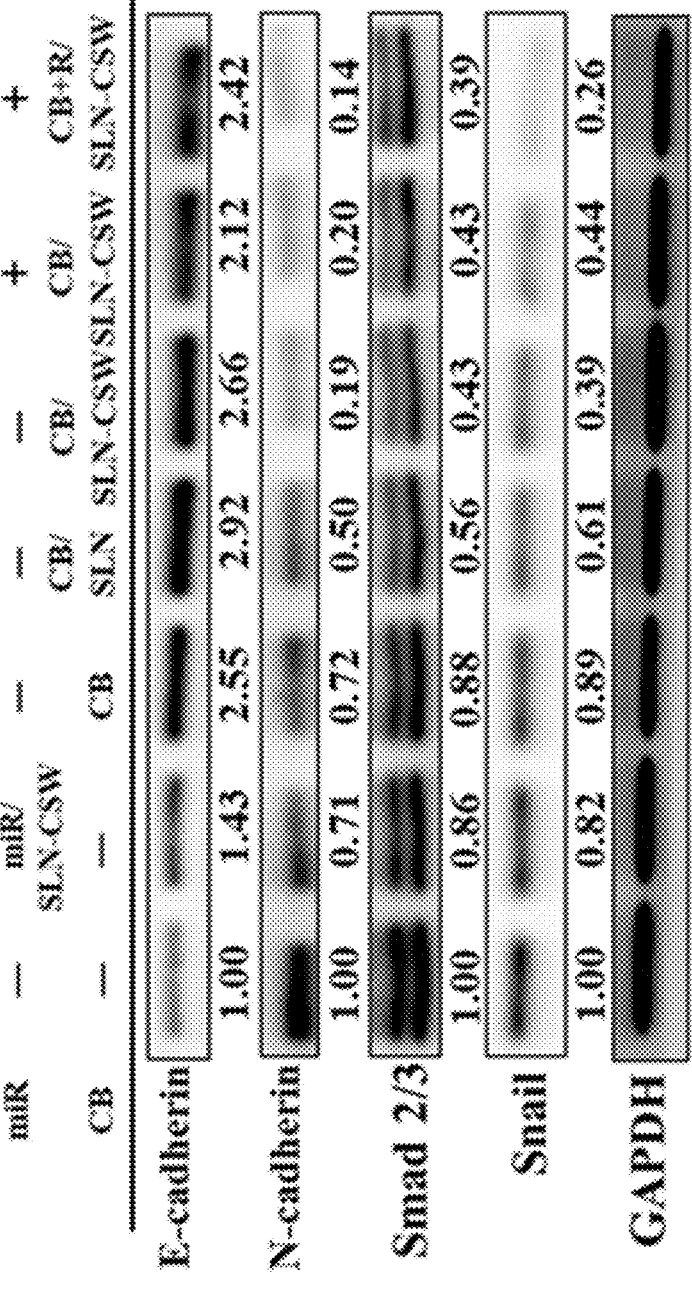
FIG. 15A shows effects of various formulations on EMT pathway.
Figure 15B:
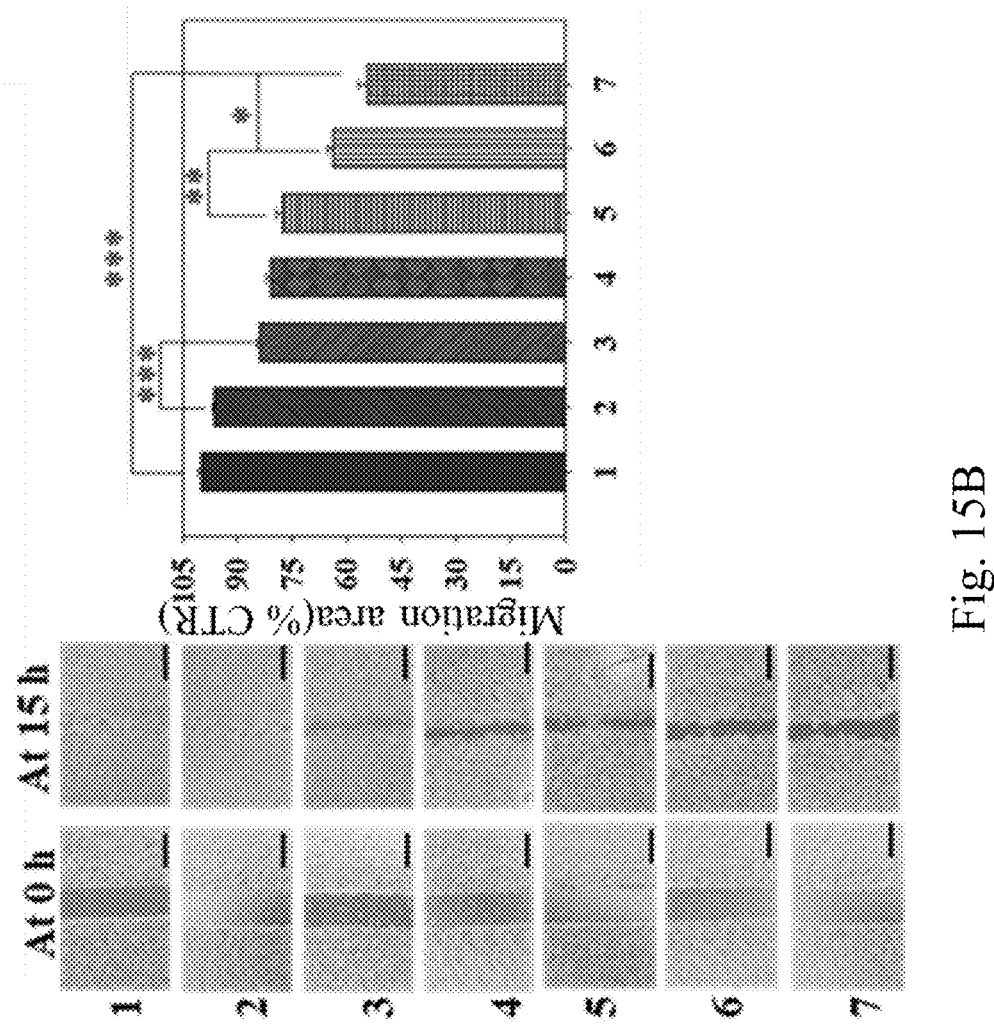
FIG. 15B shows migration assay after treatment of Panc-02 cells with various formulations for 15 h (Left). Quantification of the relative percentages of cell-migration area (Right).

Panc-02 cells were seeded in Ibidi culture insert. Cells were treated with different formulations for 15 h after removed the inserts. Before (0 h) and after (15 h) the treatments, the images were taken by microscopy. Migration area was measured and quantified by ImageJ. The result is shown in FIGS. 15A-15B.

Migration area (% of area at 0 h)=100%−[Blank area (15 h)/Blank area (0 h)×100%]

Example 16. Observation of CRT Translocation

Figure 16:
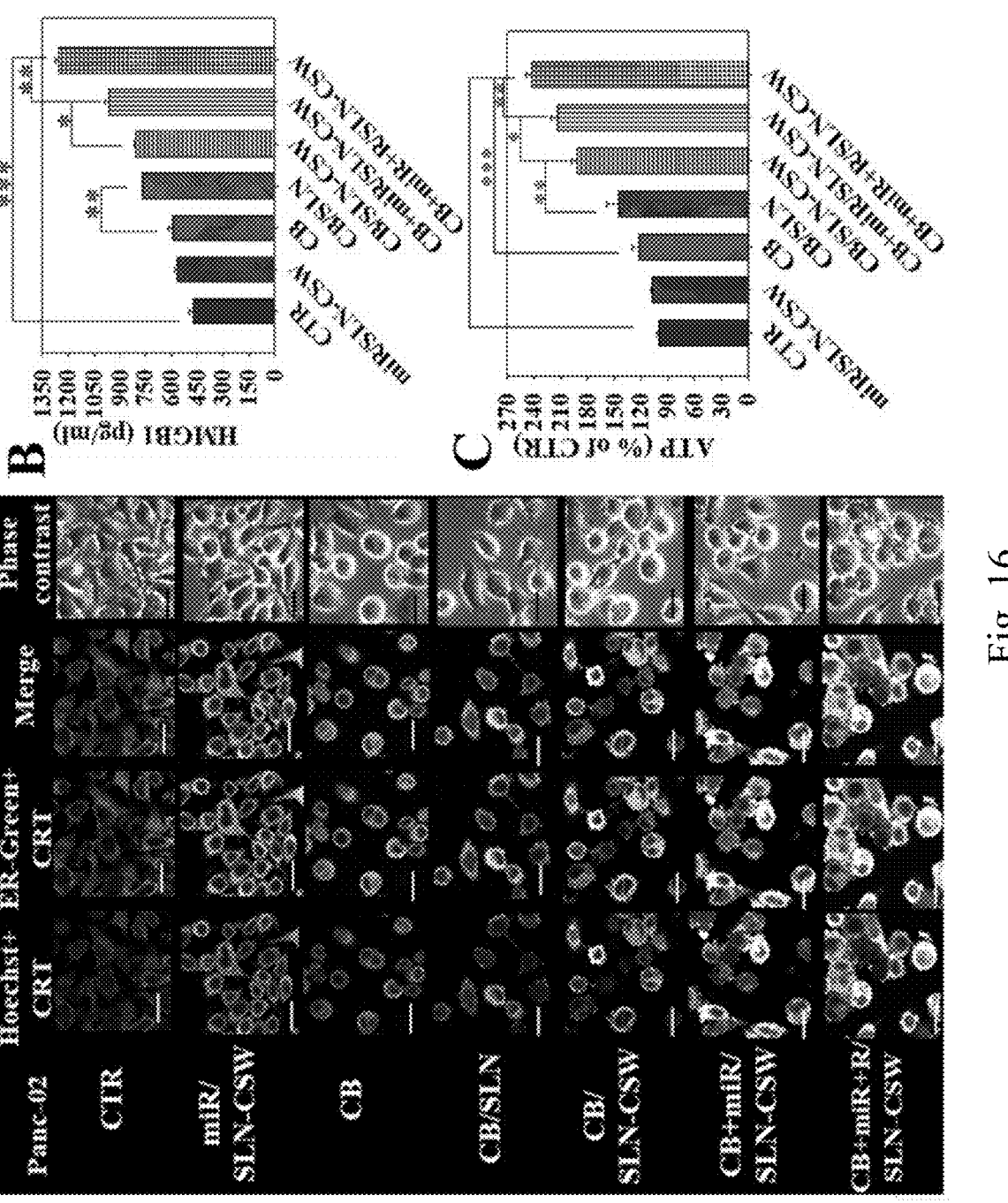
In FIG. 16, panel A shows the result of CRT exposure onto cell membranes as observed by CLSM.
Figure 17A:
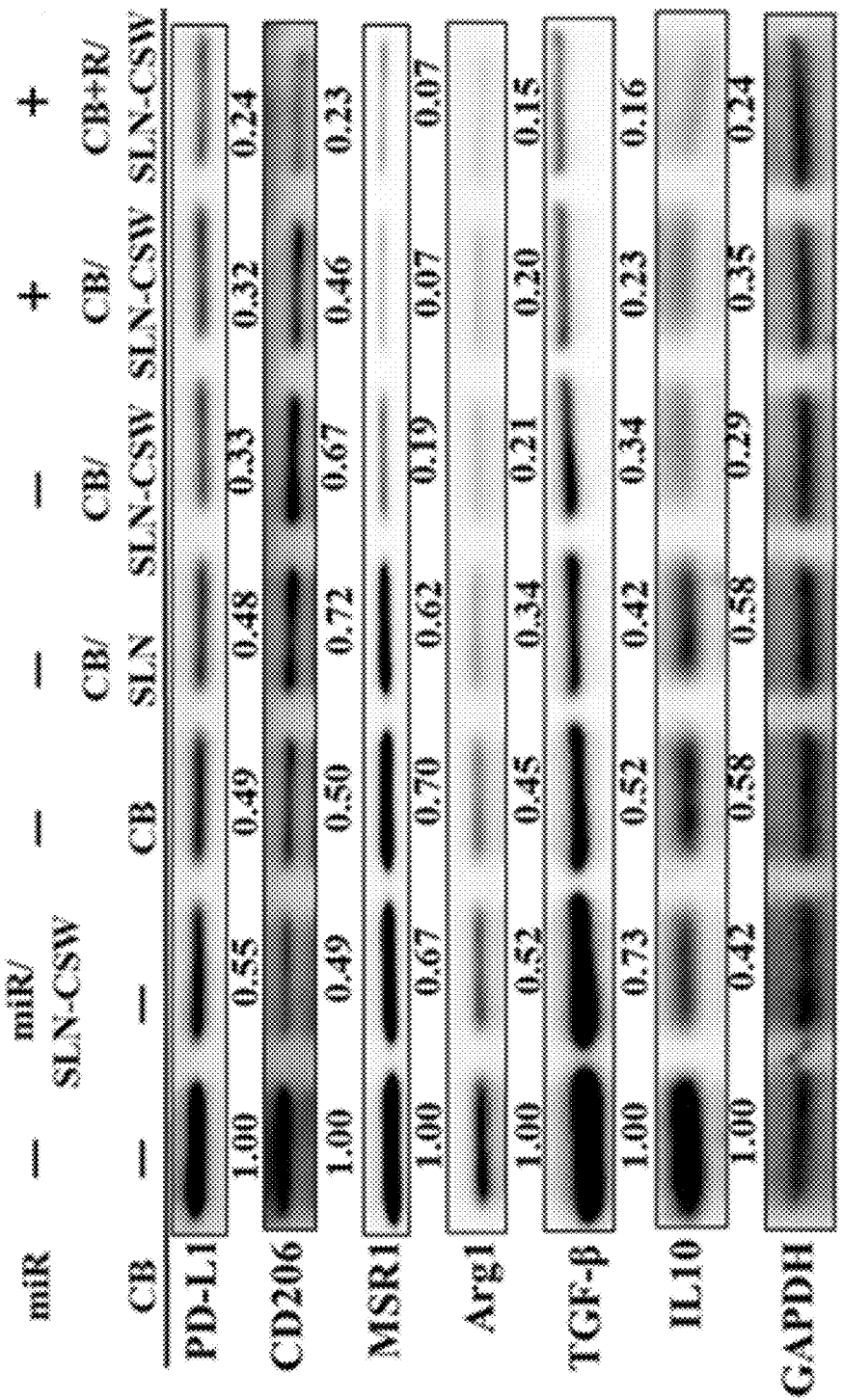
FIG. 17A shows assessment of the markers of M2 macrophages by western blot.
Figure 17B:
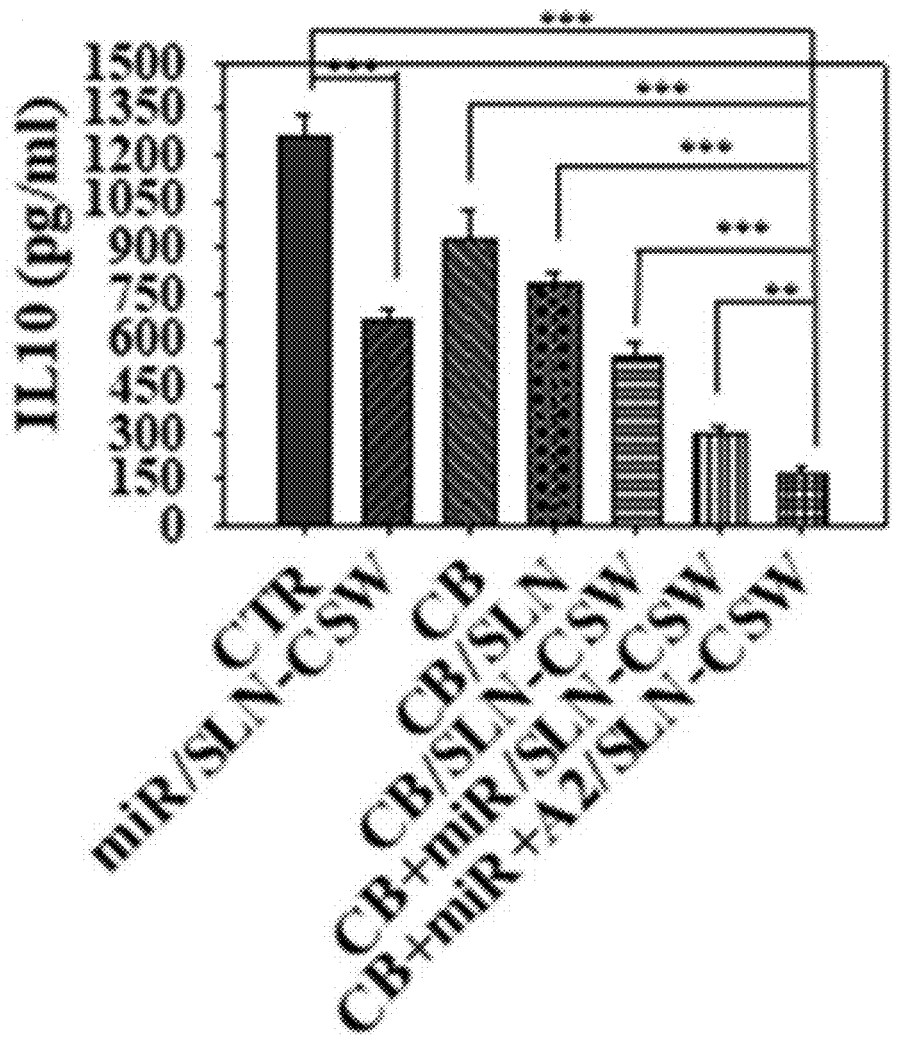
FIG. 17B shows the result of the detection of the IL-10 cytokines of M2 macrophages by ELISA kits.
Figure 17C:
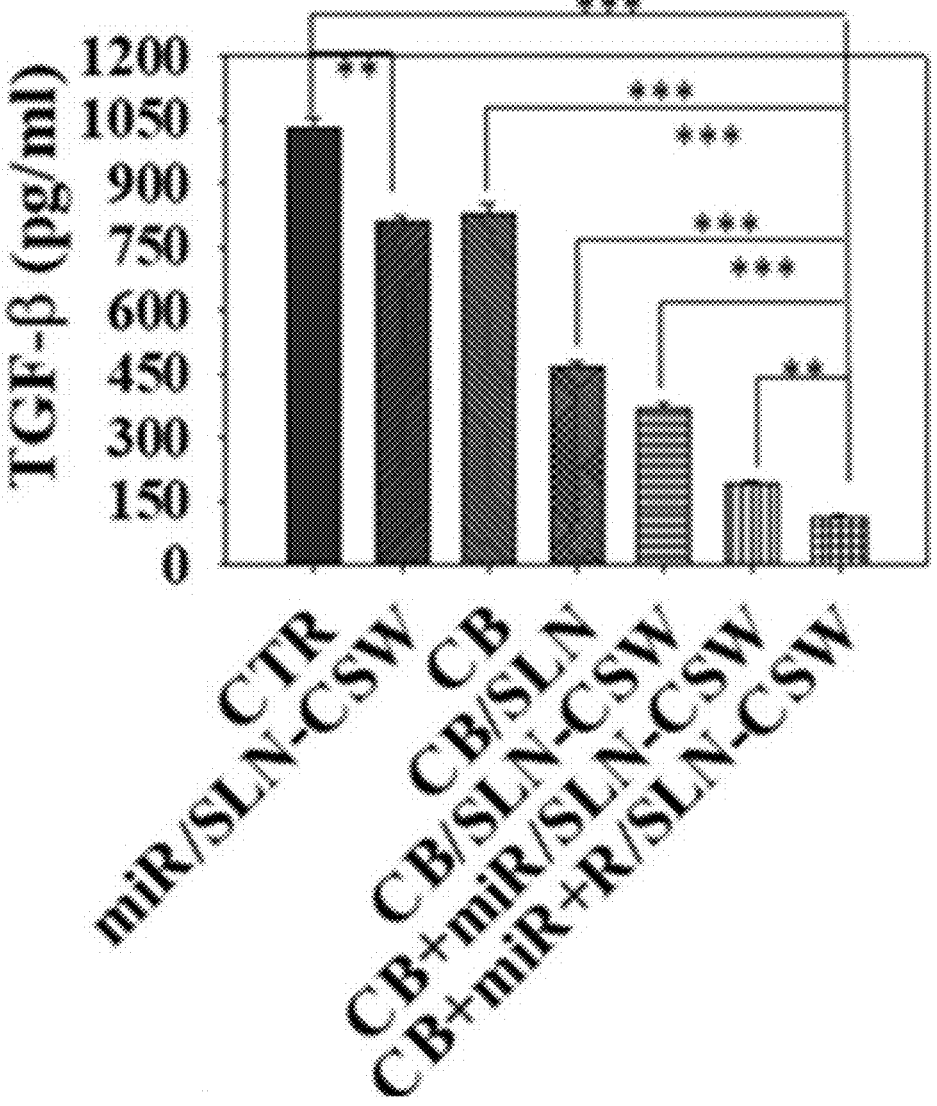
FIG. 17C shows the result of the detection of the TGF-β cytokines of M2 macrophages by ELISA kits.
Figure 17D:
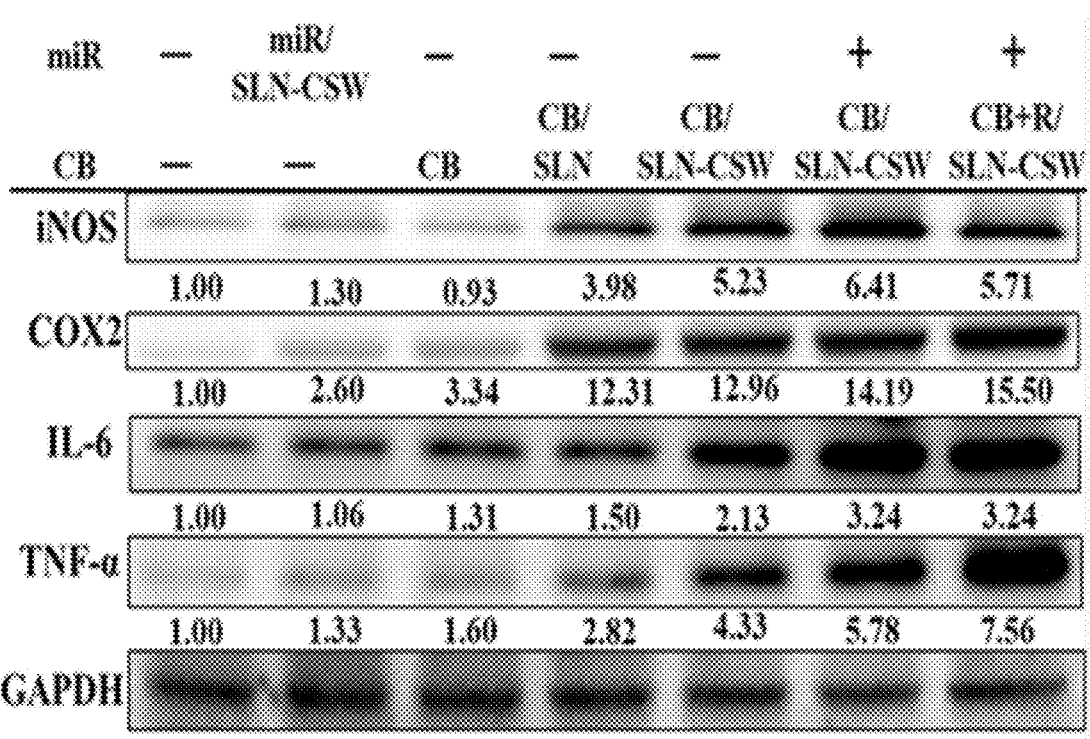
FIG. 17D shows evaluation of the markers of M1 macrophages by western blot.
Figure 17E:
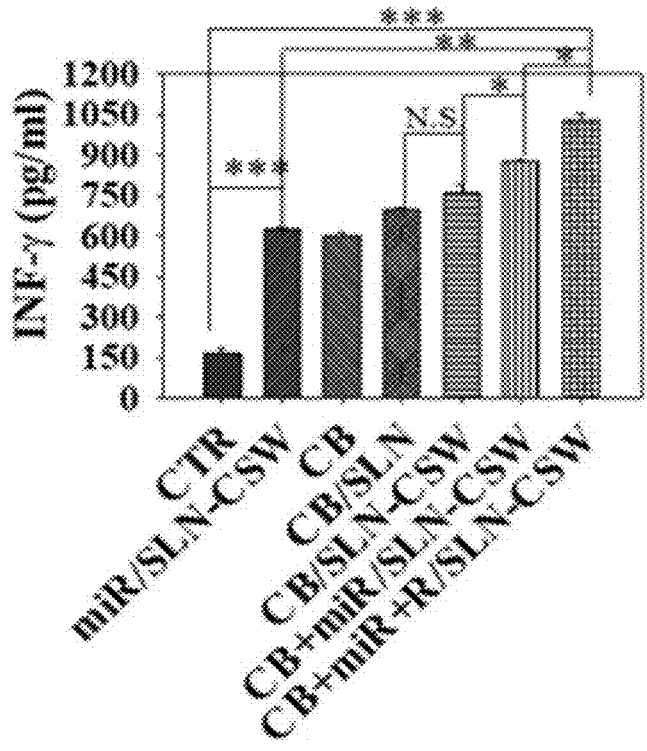
FIG. 17E shows the result of the detection of the INF-γ cytokines of M1 macrophages by ELISA kits.
Figure 17F:
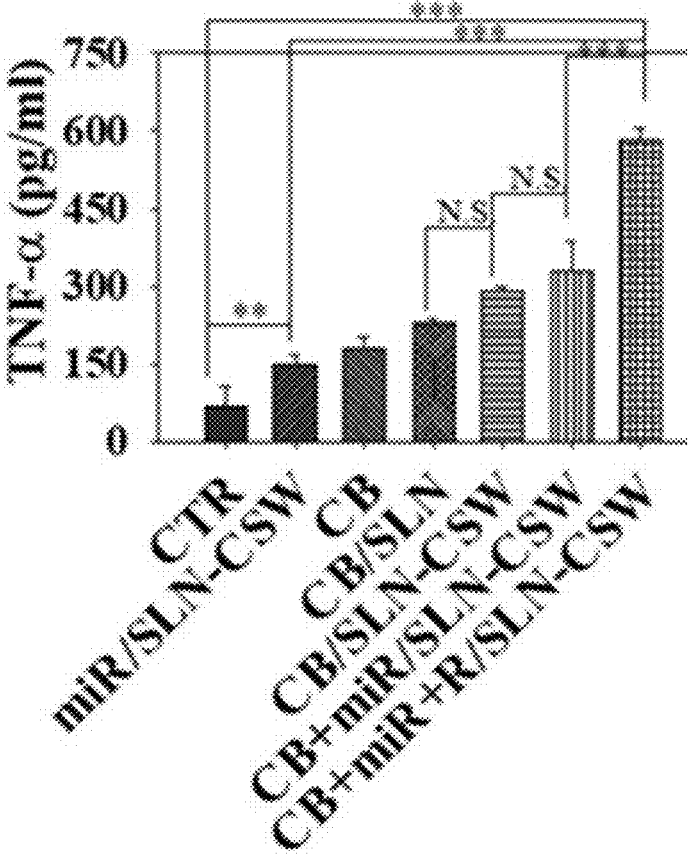
FIG. 17F shows the result of the detection of the TNF-α cytokines of M1 macrophages by ELISA kits.
Figure 18A:
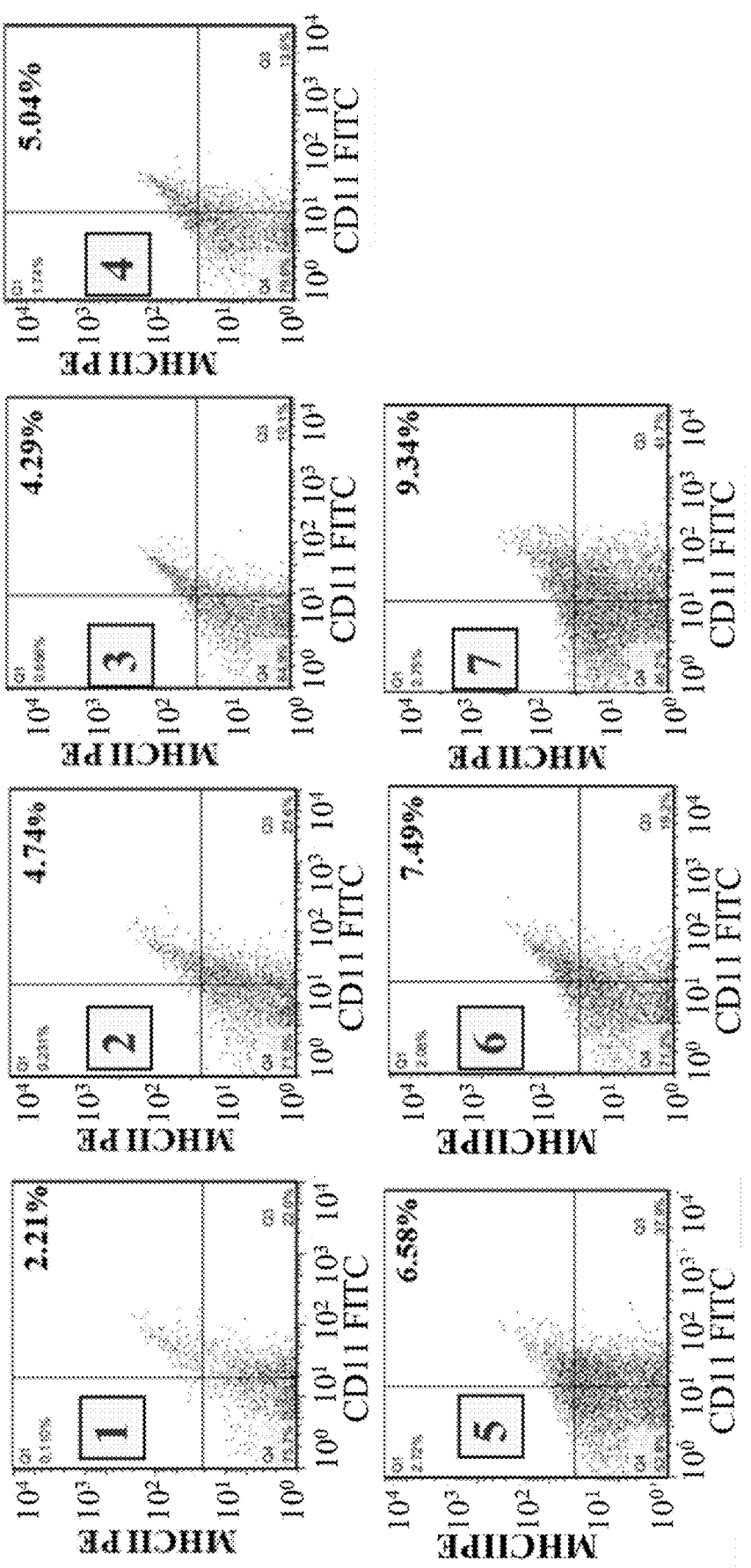
FIGS. 18A-18B show the result of the detection of the cell population distribution and relative percentages of MHCII DC cells in tumor by flow cytometry. (Left) Representative images of immune cell population distribution from five repeated experiments and (right) quantification of the relative percentages of the indicated immune cells (n=5; statistical significance at *$p < 0.05$; $p < 0.01$; *$p < 0.001$; N.S.: $p > 0.05$)
Figure 18B:
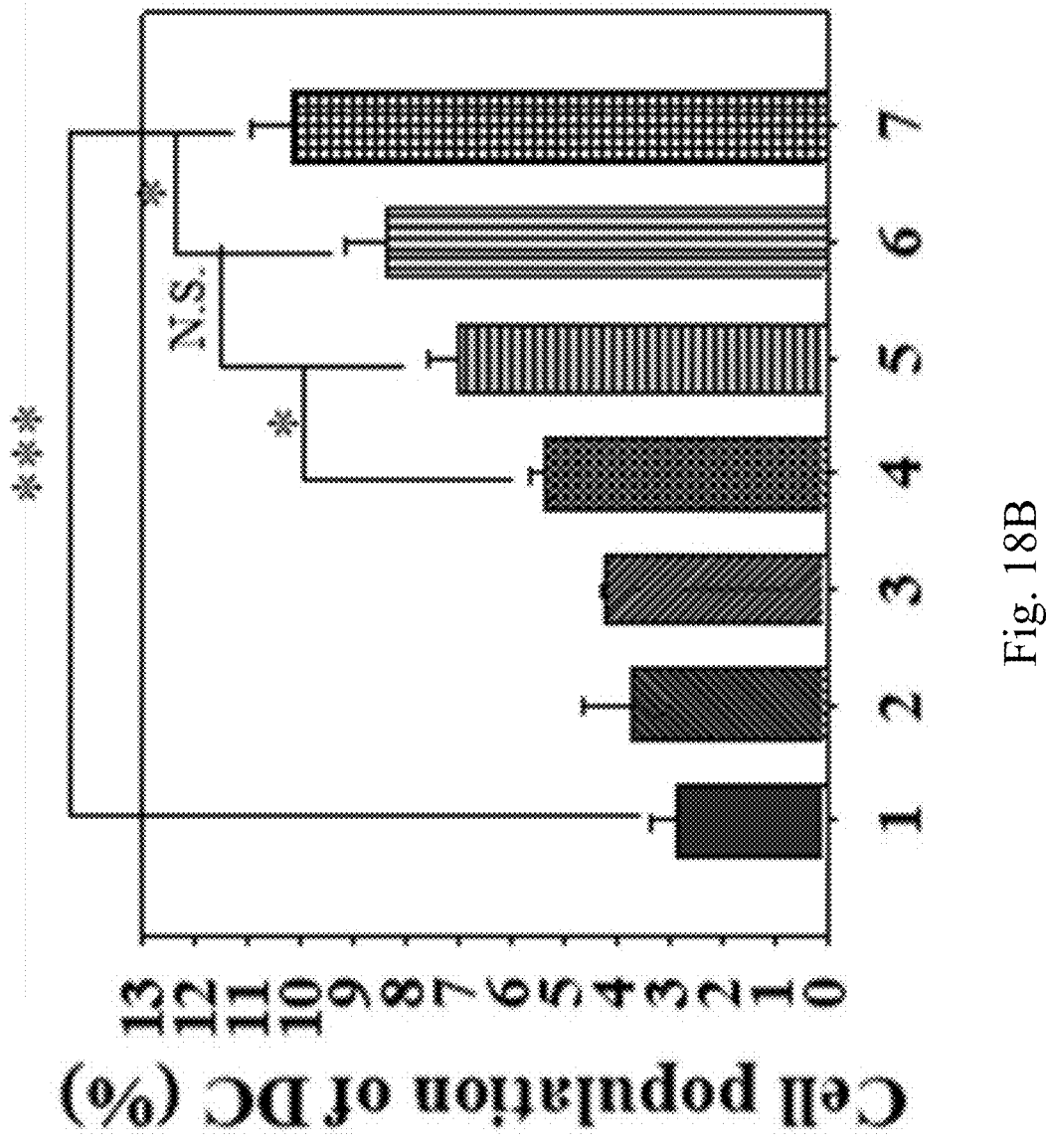
Figure 18C:
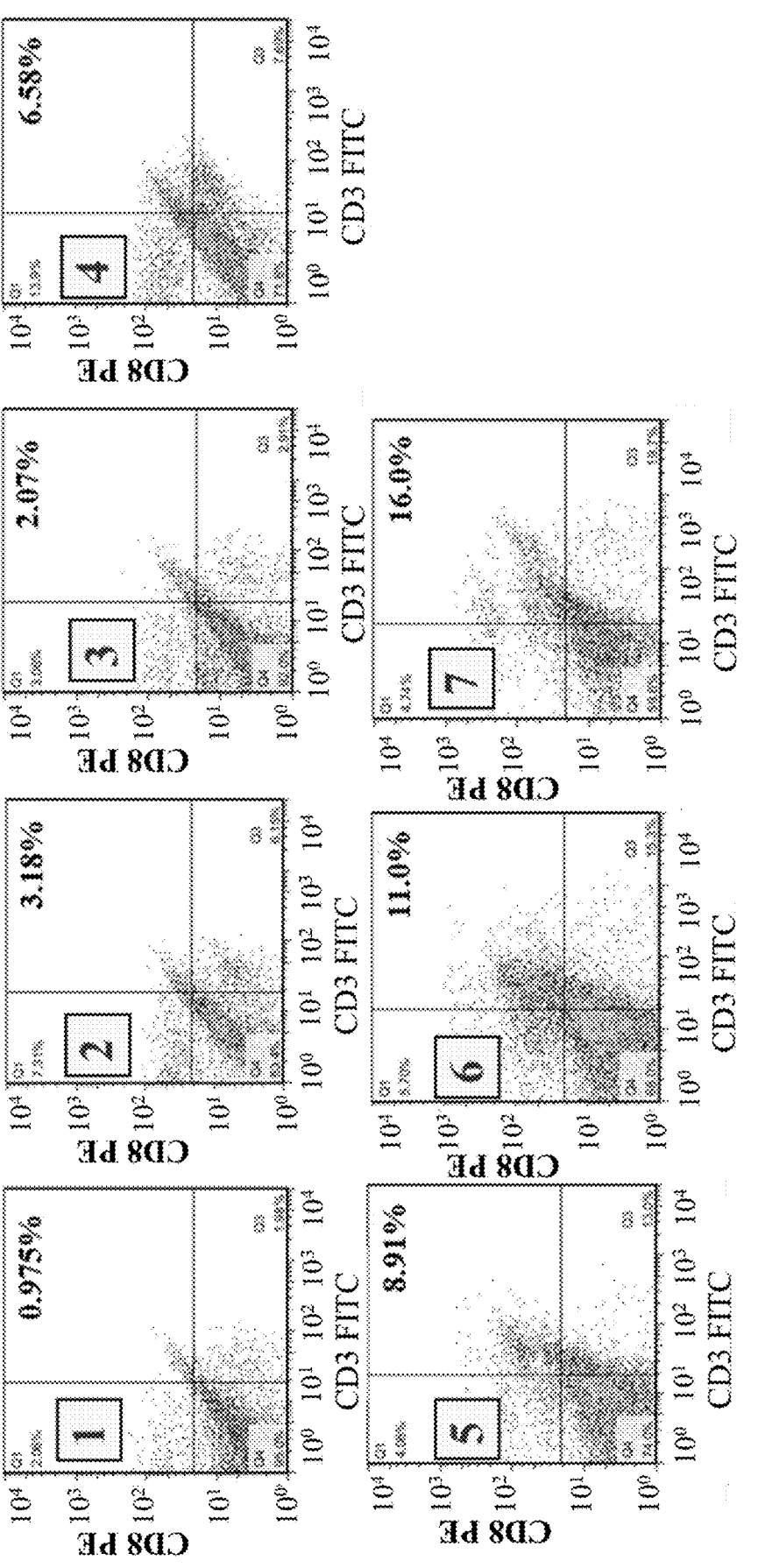
FIGS. 18C-18D show the result of the detection of the cell population distribution and relative percentages of CD8 T cell in tumor by flow cytometry. (Left) Representative images of immune cell population distribution from five repeated experiments and (right) quantification of the relative percentages of the indicated immune cells (n=5; statistical significance at *$p < 0.05$; $p < 0.01$; *$p < 0.001$; N.S.: $p > 0.05$)
Figure 18D:
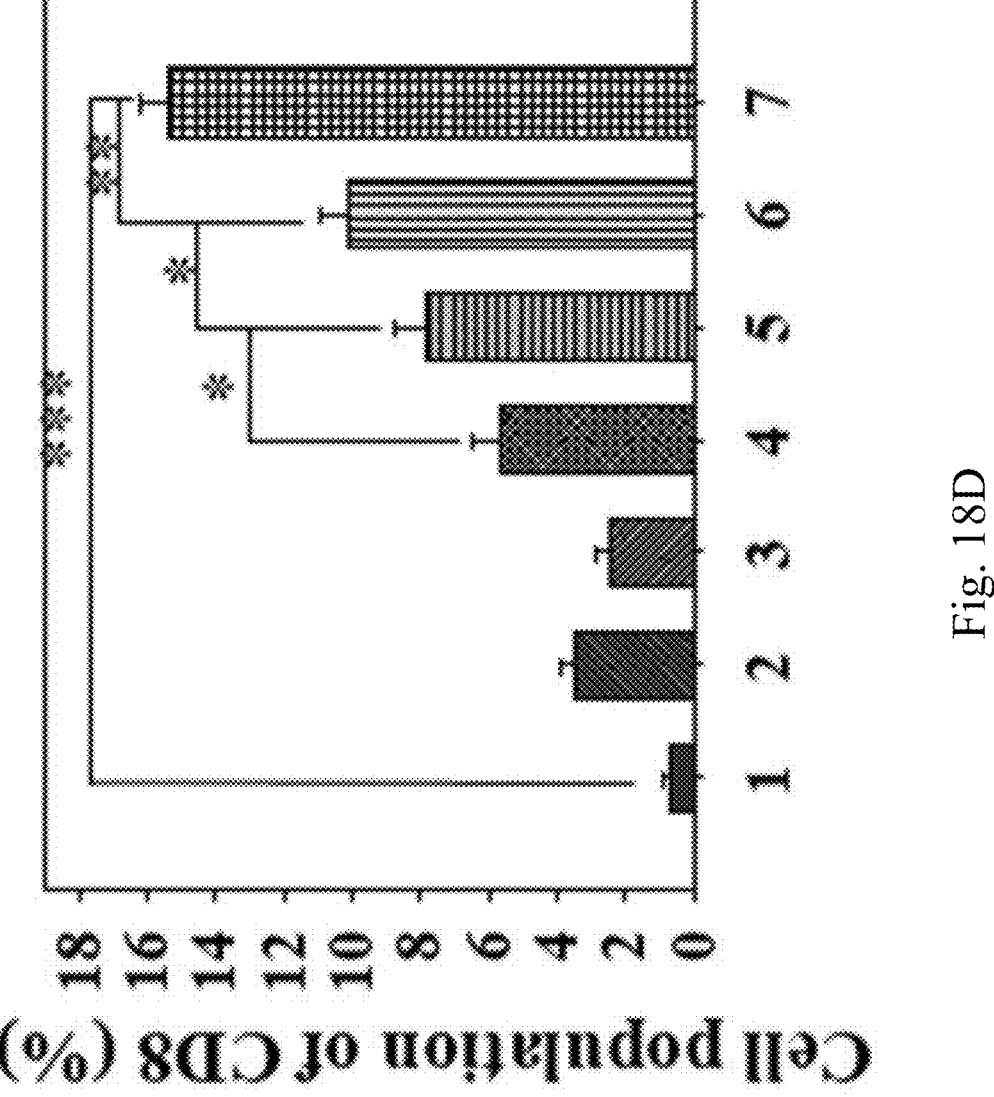
Figure 19A:
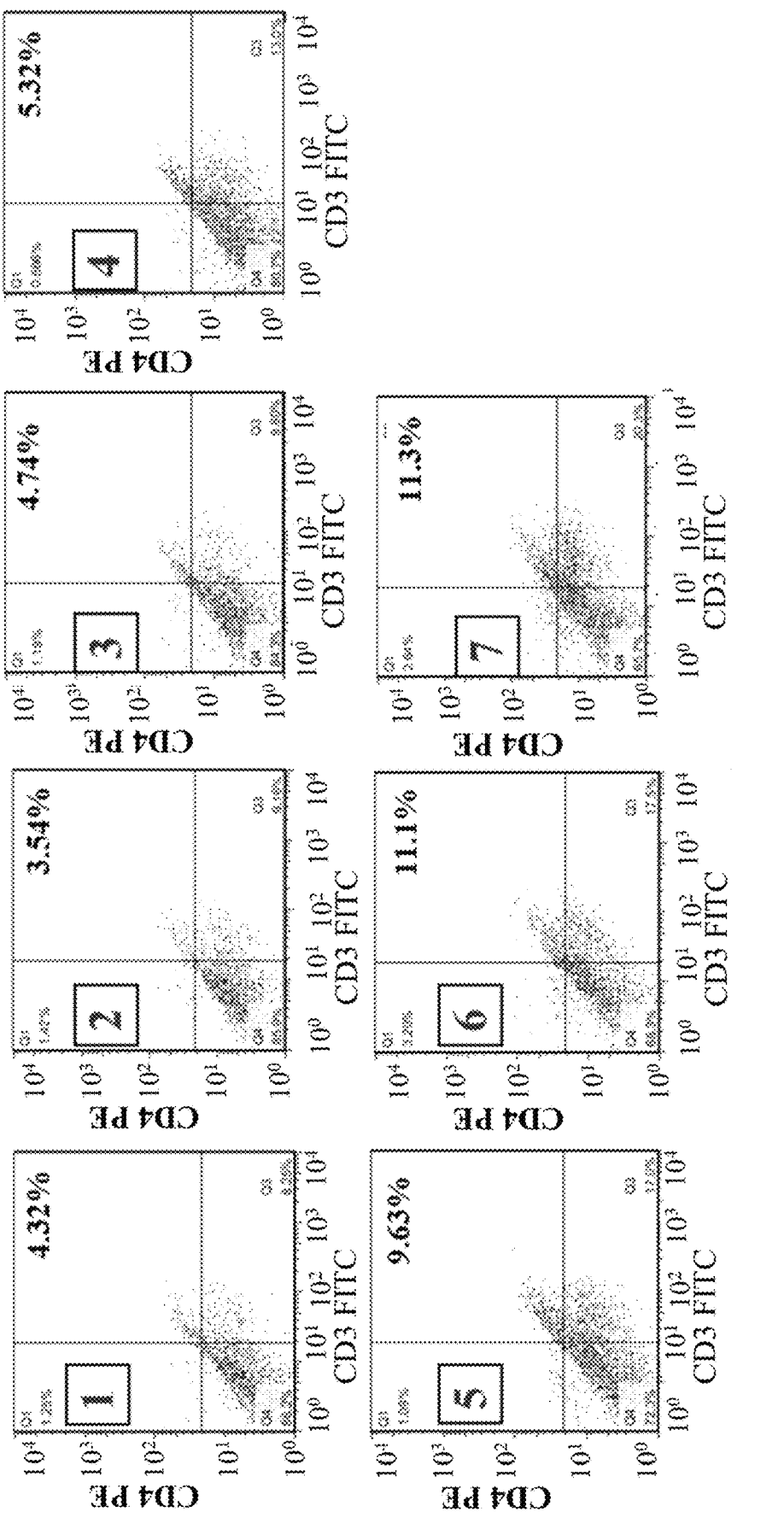
FIGS. 19A-19B show the result of the detection of the cell population distribution and relative percentages of CD4 T cell in tumor by flow cytometry. (Left) Representative images of immune cell population distribution from five repeated experiments and (right) quantification of the relative percentages of the indicated immune cells (n=5; statistical significance at *$p < 0.05$; $p < 0.01$; *$p < 0.001$; N.S.: $p > 0.05$)
Figure 19B:
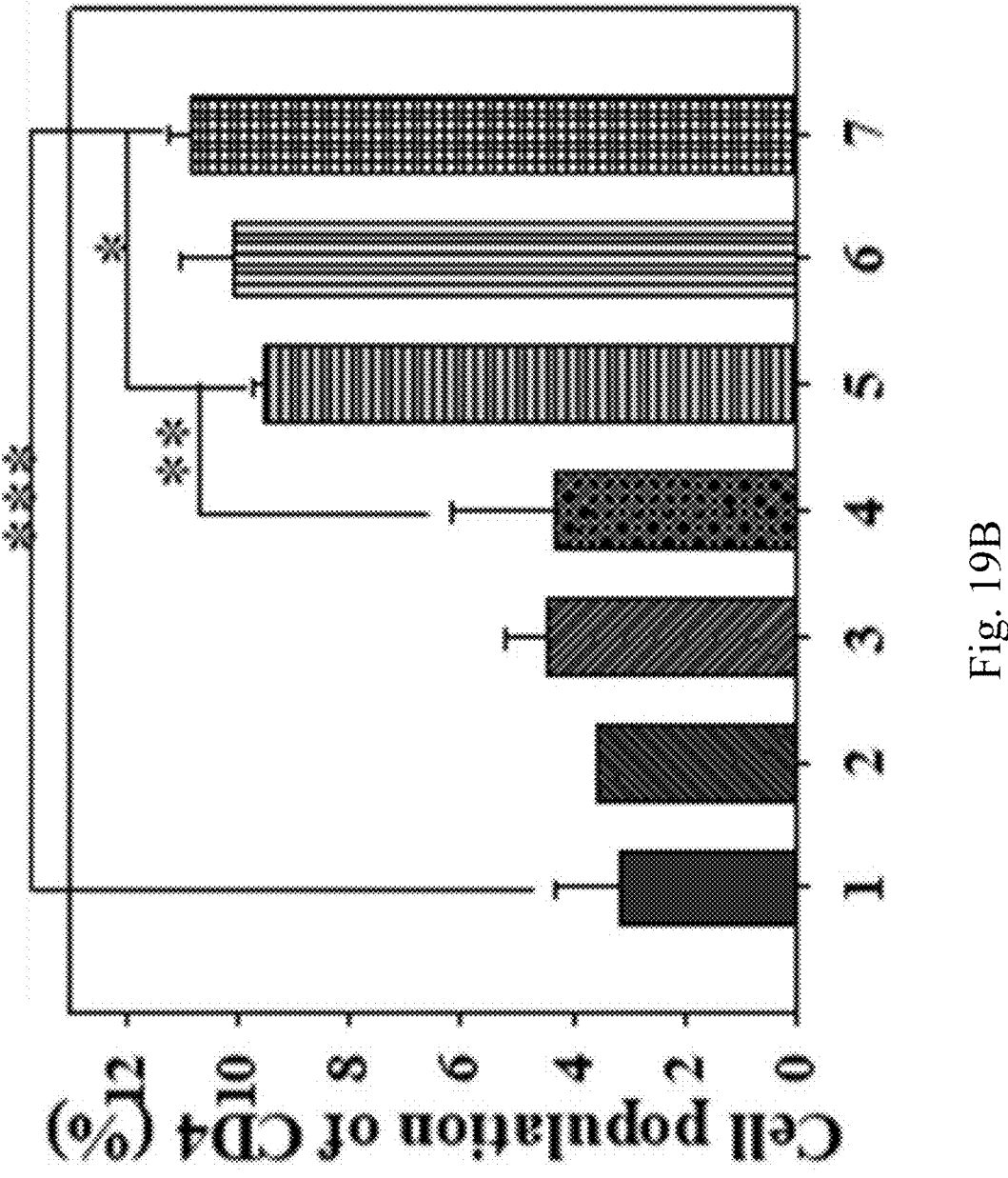
Figure 19C:
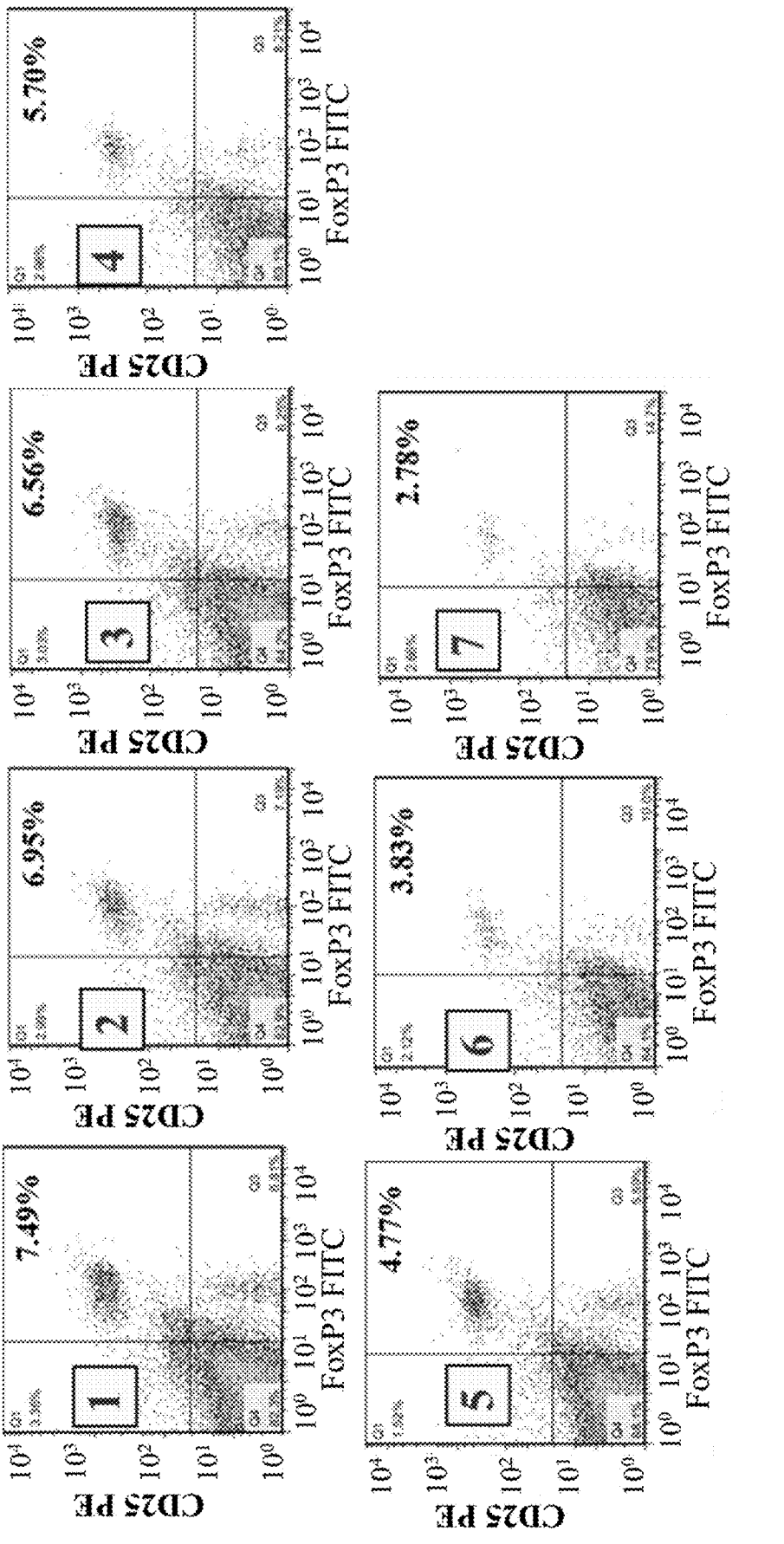
FIGS. 19C-19D show the result of the detection of the cell population distribution and relative percentages of Treg in tumor by flow cytometry. (Left) Representative images of immune cell population distribution from five repeated experiments and (right) quantification of the relative percentages of the indicated immune cells (n=5; statistical significance at *$p < 0.05$; $p < 0.01$; *$p < 0.001$; N.S.: $p > 0.05$)
Figure 19D:
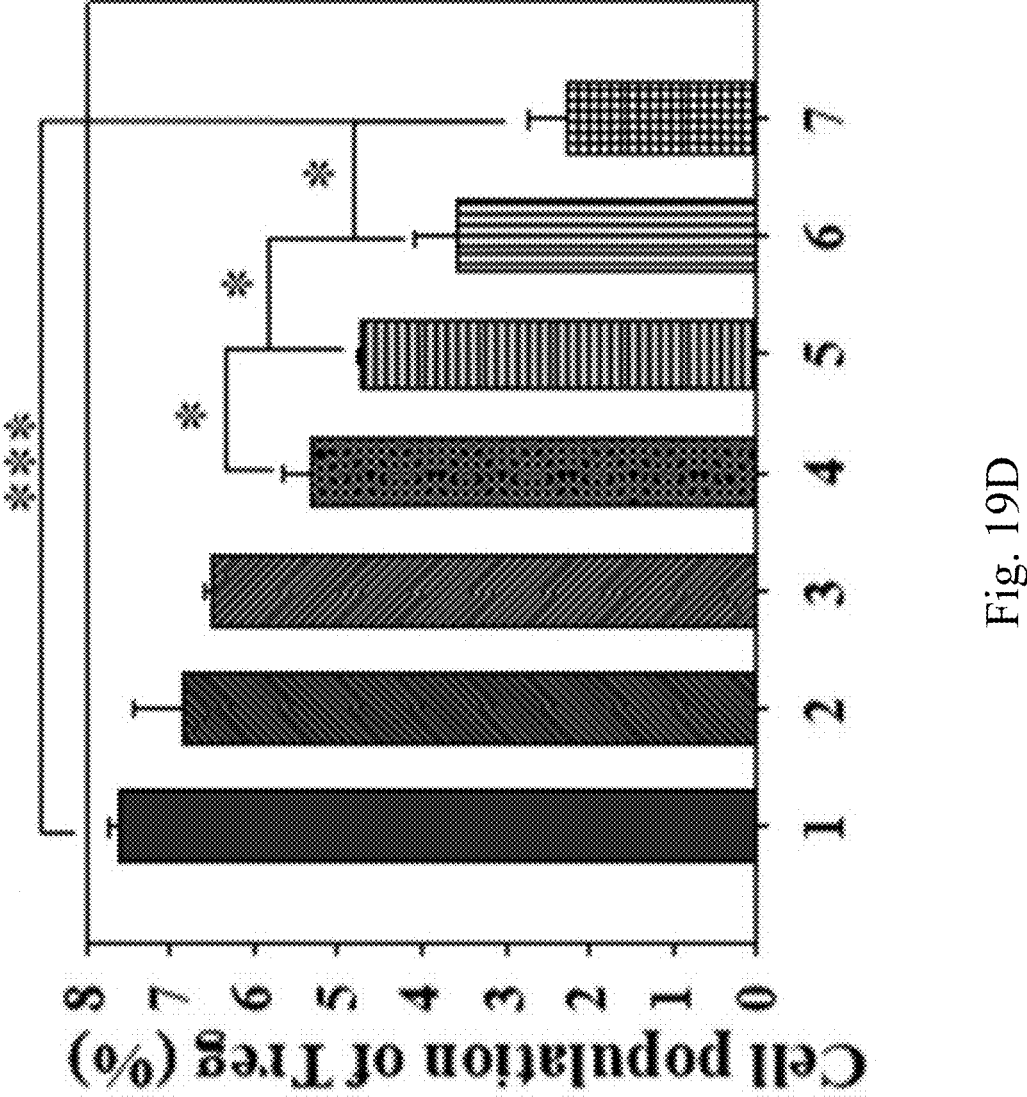
Figure 20A:
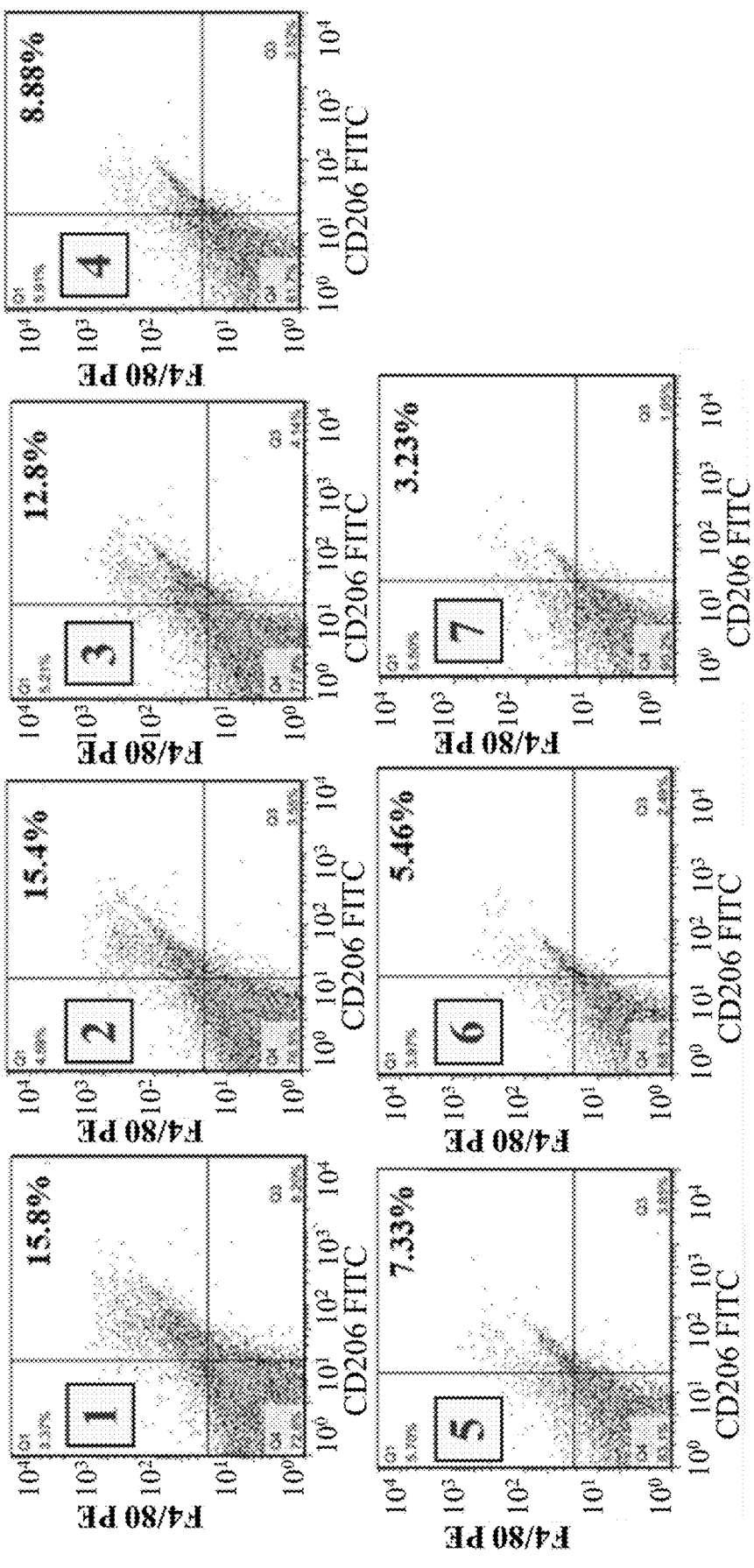
FIGS. 20A-20B show the result of the detection of the cell population distribution and relative percentages of M2 macrophages in tumor by flow cytometry. (Left) Representative images of immune cell population distribution from five repeated experiments and (right) quantification of the relative percentages of the indicated immune cells (n=5; statistical significance at *$p < 0.05$; $p < 0.01$; *$p < 0.001$; N.S.: $p > 0.05$)
Figure 20B:
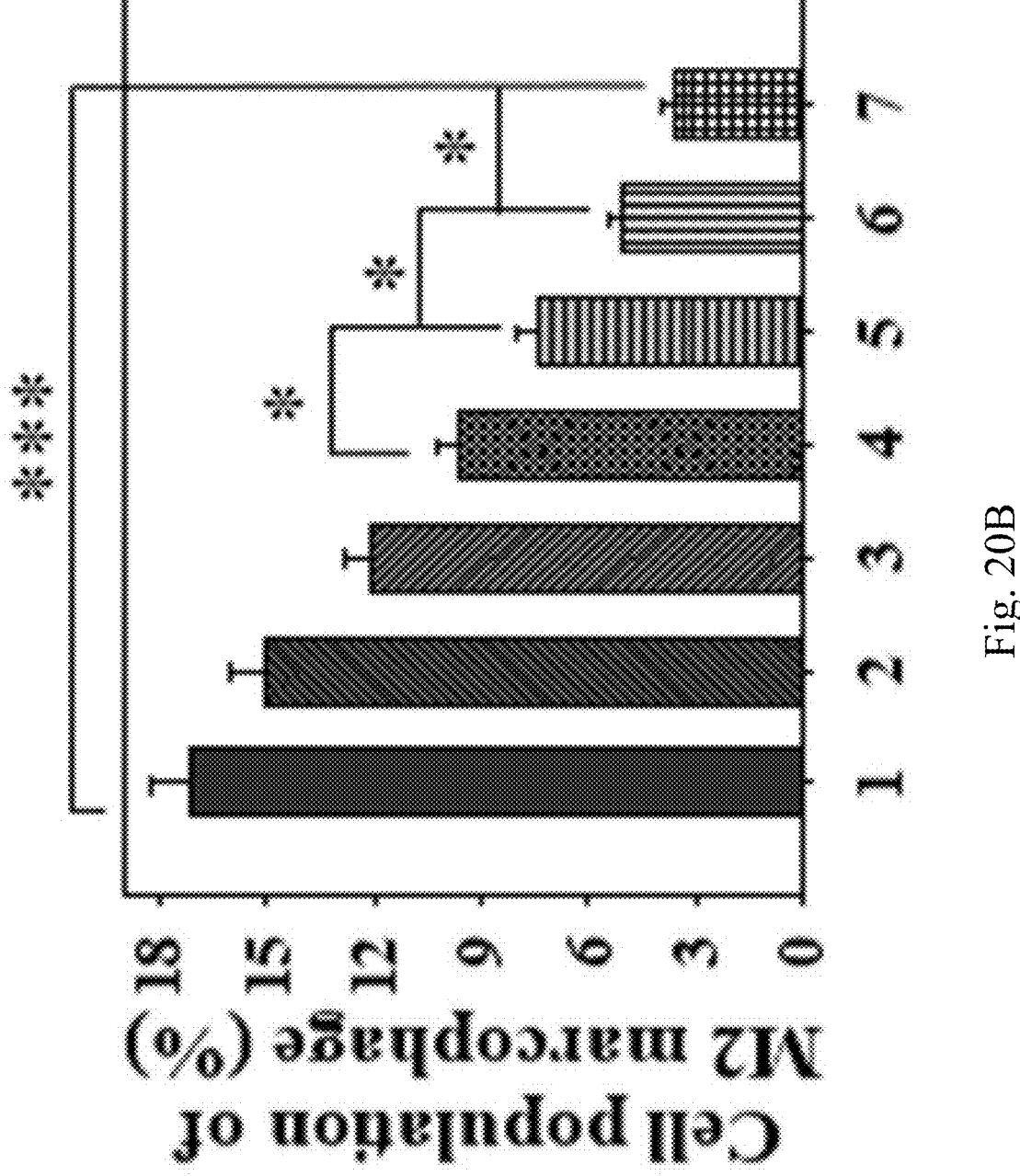
Figure 21A:
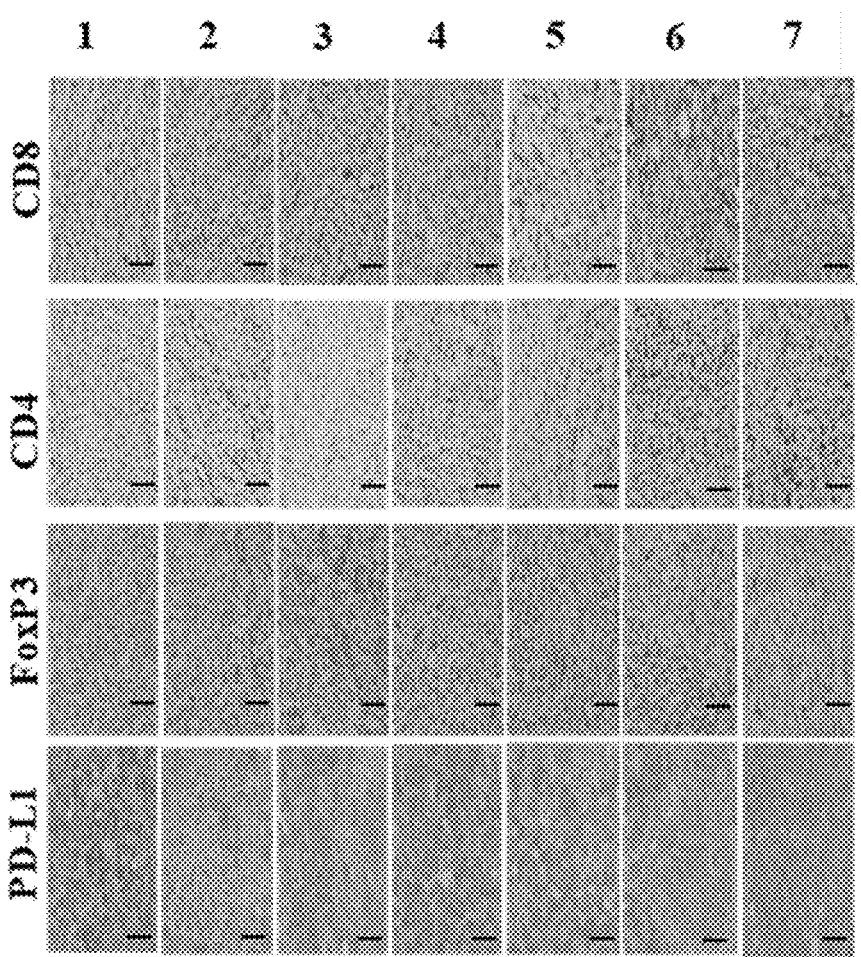
FIG. 21A shows representative images of the infiltration of CD8, CD4, Treg (FoxP3), and PD-L1 in tumor sections by immunohistochemical (IHC) staining.
Figure 21B:
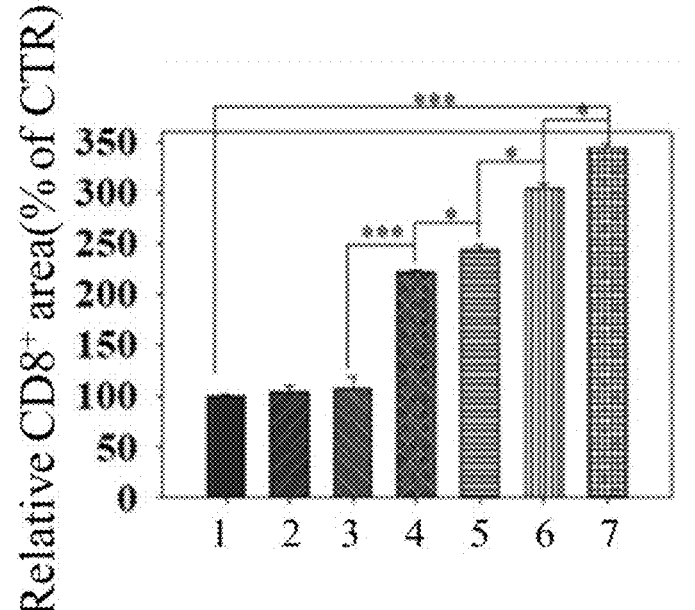
FIG. 21B-21E show the result of quantification of the relative percentages of positive area of CD8, CD4, Treg (FoxP3), and PD-L1, respectively (n=5; statistical significance at *$p < 0.05$; $p < 0.01$; *$p < 0.001$; N.S.: $p > 0.05$).
Figure 21C:
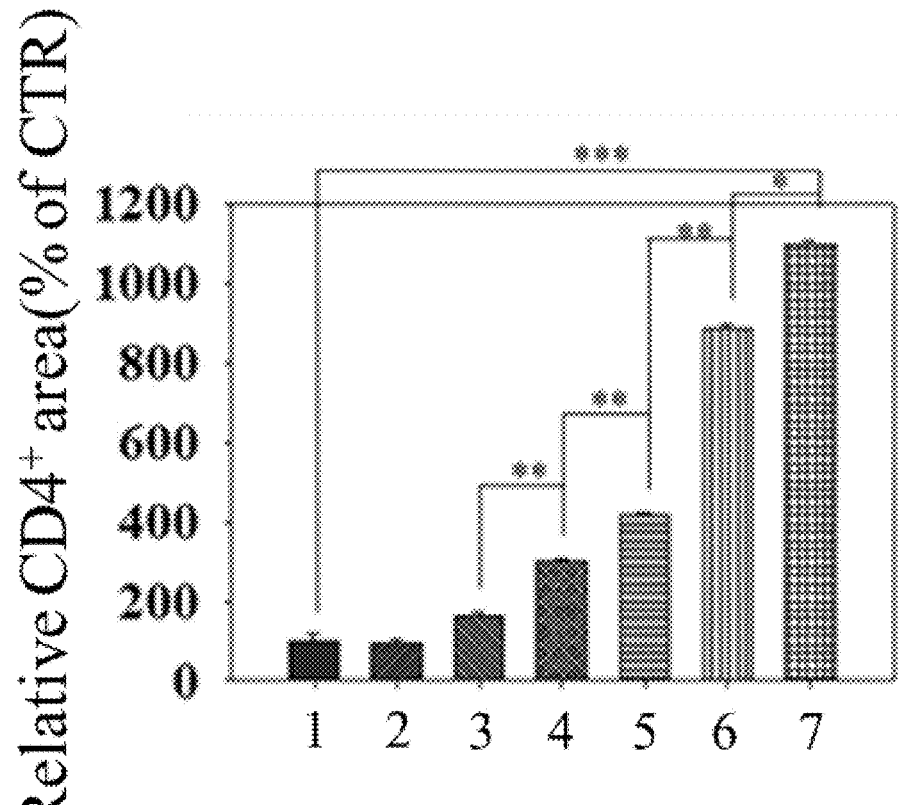
Figure 21D:
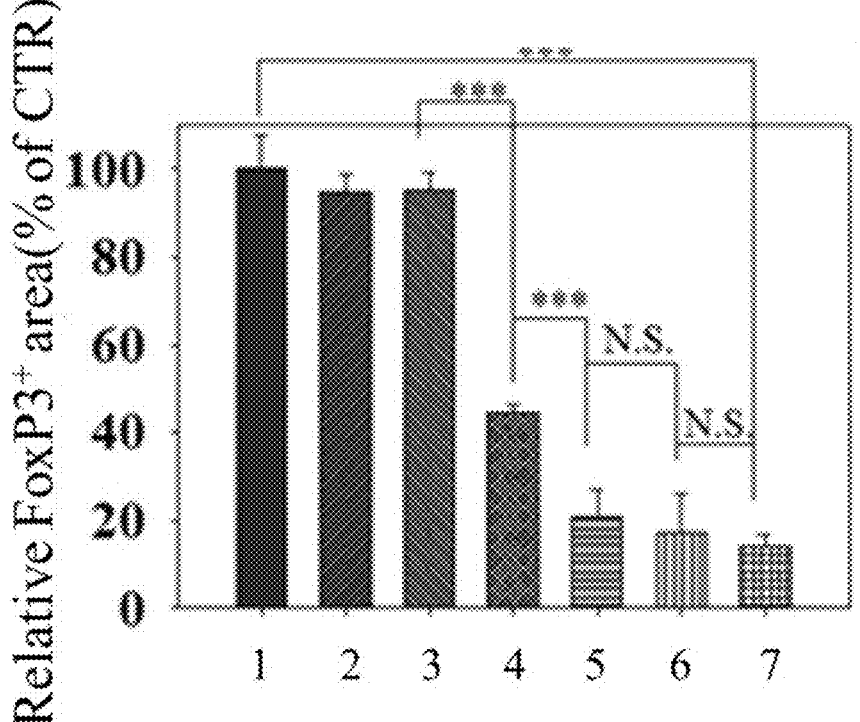
Figure 21E:
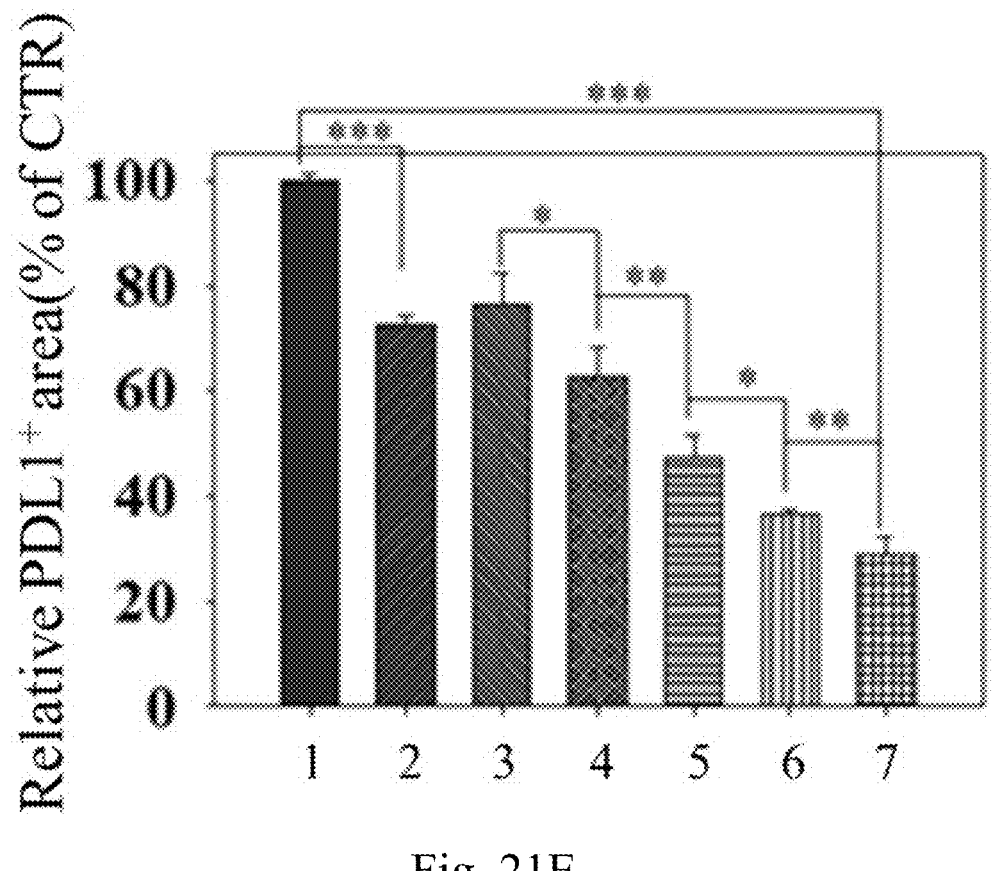

Panc-02 cells were seeded in 6-well plates and treated with different SLNs formulations. After treatment, the nucleus and endoplasmic reticulum were stained by a ER staining kit. Then, the cells were fixed in 4% paraformaldehyde. After blocking with fetal bovine serum. CRT were then tagged with primary antibody. Finally, the primary antibody was labeled with the Cy5 secondary antibody. Images were taken by a confocal laser scanning microscope. The result is shown in FIG. 16A.

Example 17. Detection of Cytokines and HMGB1 Release by ELISA Kits

To evaluate the release of cytokine and HMGB1, the ELISA kits were used. One day prior to running the ELISA, the capture antibody was first coated on the 96-well plate. Then, the plate was washed and blocked the non-specific binding background by using assay diluent buffer. The standards and samples were then added into plate and incubated at room temperature. After washing the plate, detection antibody was added and incubated at room temperature. Then, the plate was washed and the Avidin-HRP solution was added and incubated. The TMB Substrate Solution was added into the plate and incubated in the dark. Finally, to stop the reaction, the stop buffer was added. The plates were read at 450 nm using an ELISA reader. The result is shown in FIG. 16B.

14

Example 18. Detection of ATP

Panc-02 cells were seeded in 12-well plates and treated with different SLNs formulations. ATP Detection Assay Kit-Luminescence was used for detecting ATP. To detect the ATP released from cells, the condition medium was first collected after treatment, and then mixed with ATP detection assay buffer. D-luciferin and luciferase. The mixture solution was added into luminescence white plate, and the relative level of ATP was measured by ELISA reader. The result is shown in FIG. 16C.

Example 19. Co-Culture Model Establishment

For co-culture system. RAW 264.7 macrophages were seeded into 12-well plate, and Panc-02 cell were seeded onto cell inserts. After co-culture for 24 h. Panc-02 cell were treated with different formulations for 48 h. Next. RAW264.7 cells or Panc-02 cells and condition medium were collected for Western blotting and ELISA testing, respectively. The result is shown in FIGS. 17A-17F.

Example 20. Immune Cells Infiltrations Measurement In Vivo

To analyze the types of infiltrated immune cells, the tumors and spleens were isolated and chopped by using surgical scissors from Panc-02 tumor-bearing mice receiving different treatments. Tissues were digested with Collagenase Type VI. DNase I. and then passed through 70 μm cell strainer. After PBS washing, single-cell suspensions were isolated, stained by corresponding fluorescein-conjugated antibodies for 20 min in dark. The preliminary FSC/SSC gates of the initial cell population were determined depending on the lymphocyte sizes. Flow cytometry was performed on all samples and analyzed with the FlowJo software. The result is shown in FIGS. 18A-21E.

Example 21. Bio-Plex Pro Mouse Cytokine 23-Plex Immunoassay

Figure 22:
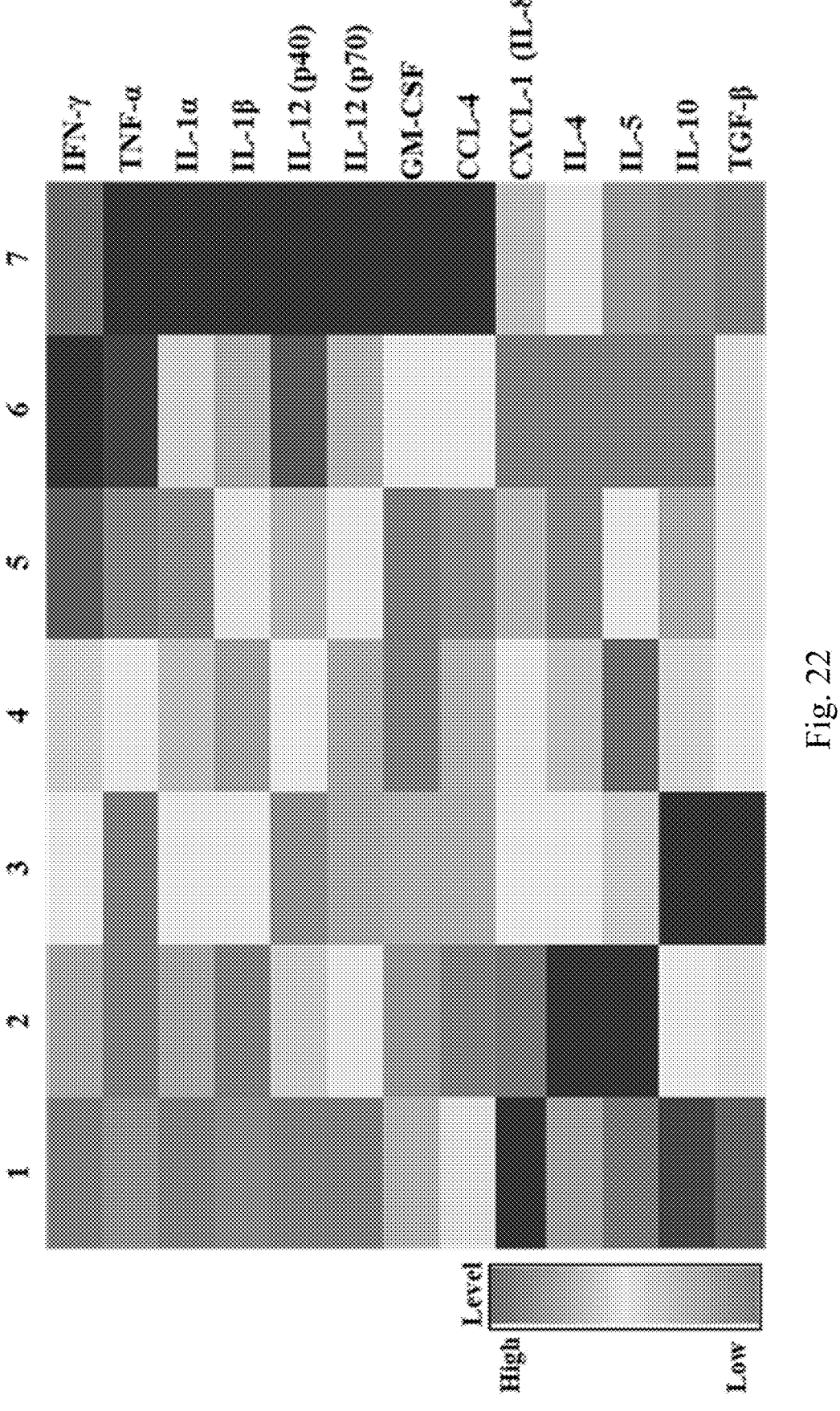
FIG. 22 shows the result of detection of the cytokine release in mouse serum by Bio-Plex Pro Mouse Cytokine Plex Immunoassay. 1: CTR; 2: miR/SLN-CSW; 3: CB; 4: CB/SLN-CSW; 5: CB+miR/SLN-CSW; 6: CB+miR+R/SLN-CSW; 7: CB+miR+R/PGA-SLN-CSW.

Blood samples were obtained from the mice eye orbit 48 hours after the final treatment and centrifuged at 1500 rpm for 20 minutes. Serum was separated and analyzed. To evaluate the in vivo cytokine release, the Bio-Plex Pro Mouse Cytokine 23-Plex Immunoassay was used. First. 50 μl beads were added into each well and washed two times. Second, the 50 μl standard, blank, samples were added and incubated at room temperature with shaking at 850 rpm for 30 min. then washed three times. Third, the 25 μl detection antibody were added and incubated at room temperature with shaking at 850 rpm for 25 min. then washed three times. Then. 50 μl streptavidin-PE were added and incubated at room temperature with shaking at 850 rpm, then washed three times. Finally, resuspend in 125 μl assay buffer and incubated at room temperature with shaking at 850 rpm for 30 sec. then analyzed by Bio-Plex system. The result is shown in FIG. 22.

Example 22. Tumor Model

Male C57BL/6 mice were purchased from National Laboratory Animal Center. Panc-02 cells were injected subcutaneously into the right flank of mice. All in vivo investigations were carried out in accordance with criteria authorized by National Yang-Ming University's Institutional Animal Care and Use Committee (IACUC).

Example 23. Antitumor Efficacy

Figure 23A:
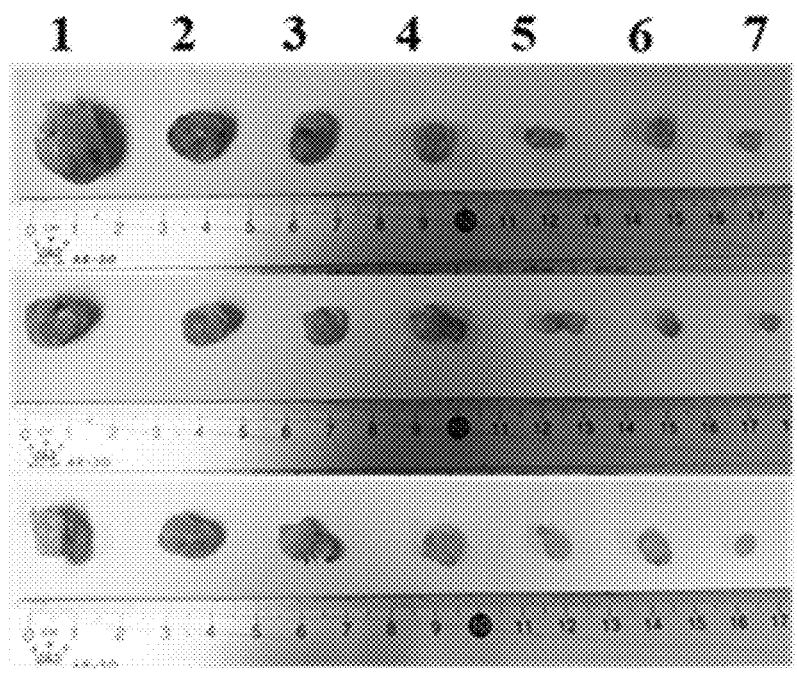
FIG. 23A shows tumor tissues isolated from Panc-02-bearing mice after completing 14-day therapy.
Figure 23B:
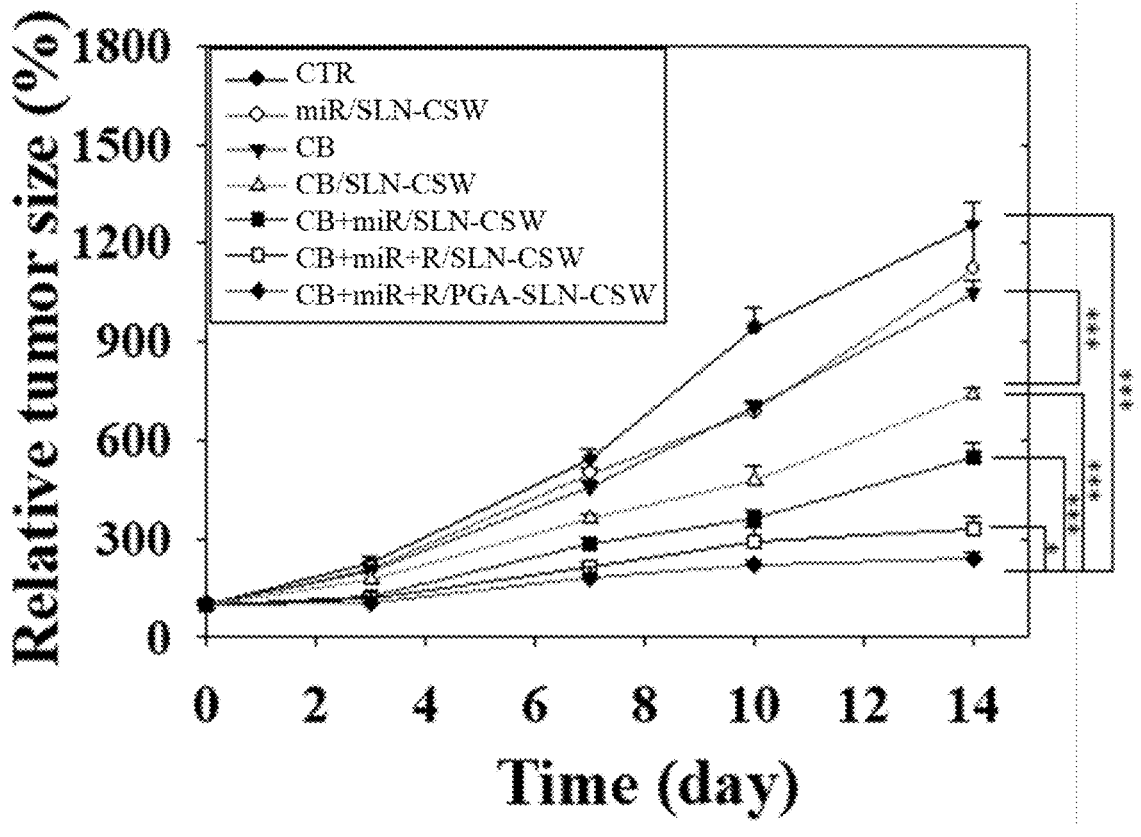
FIG. 23B shows Measurement of tumor size using a digital caliper twice per week for 2 weeks in mice treated with various formulations (n=5; statistical significance at *$p < 0.05$; ***$p < 0.001$).

When the tumors reached a volume of 60 mm³, the tumor-bearing mice were randomly separated into seven groups (n=3). Different formulations groups were used in the therapy. Mice were given tail vein injections containing CB and miR in various formulations twice a week. Tumor volumes and body weight were measured using a caliper and an electronic balance during the period of 14 days. The result is shown in FIGS. 23A-23B.

$$V = (L \times W^2)/2$$

Wherein, length (L, mm) is the longest diameter and width (W, mm) is the shortest diameter perpendicular to the length axis.

Example 24. TUNEL Assay and Hematoxylin and Eosin (H&E) Staining

Figure 24:
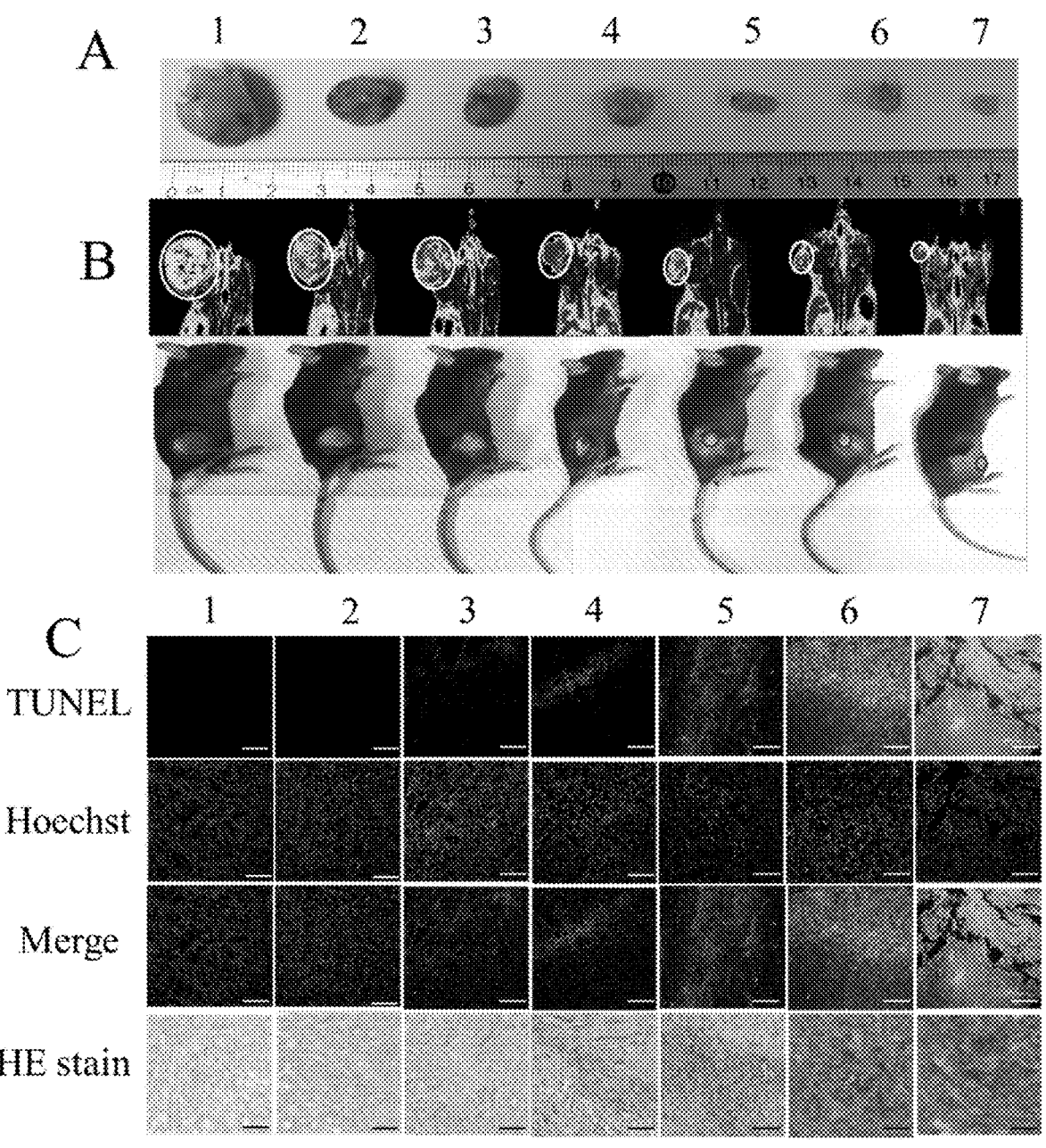
In FIG. 24, panel A shows PET/MRI images of Panc-02-bearing mice after 14-day therapy by injection of a radiant probe [$^{18}$F]-fluorodeoxyglucose ($^{18}$F-FDG: 0.282 mCi).
Figure 25A:
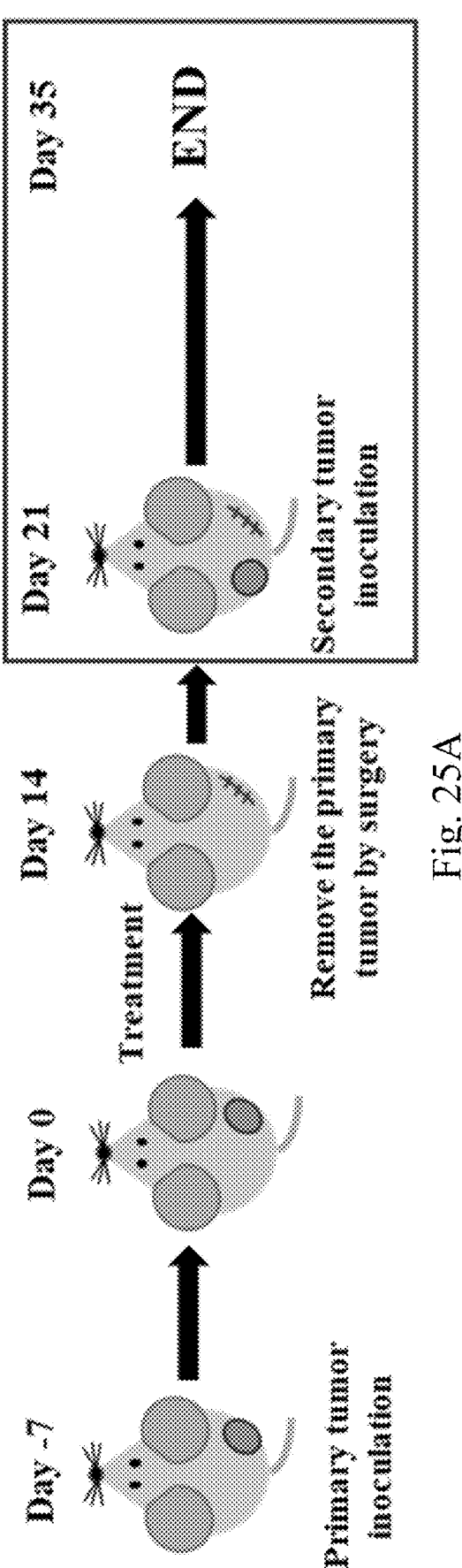
FIG. 25A shows the flow chart of re-challenge study.
Figure 25B:
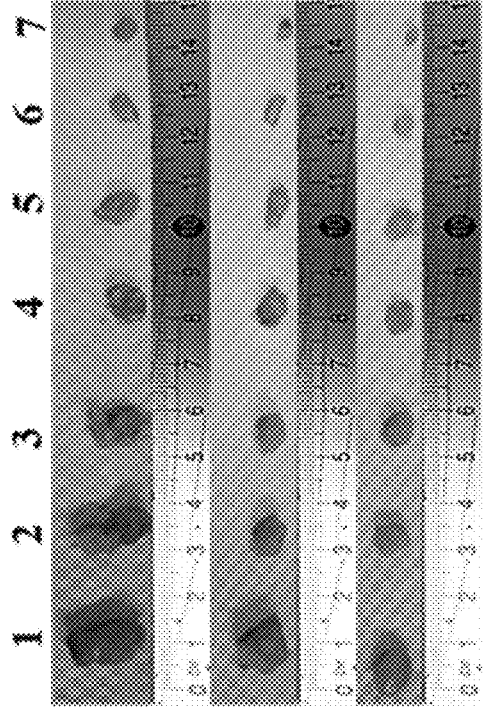
FIG. 25B shows representative images of the second tumors isolated from re-challenged Panc-02-bearing mice after completing the second 14-day treatment (n=5).
Figure 25C:
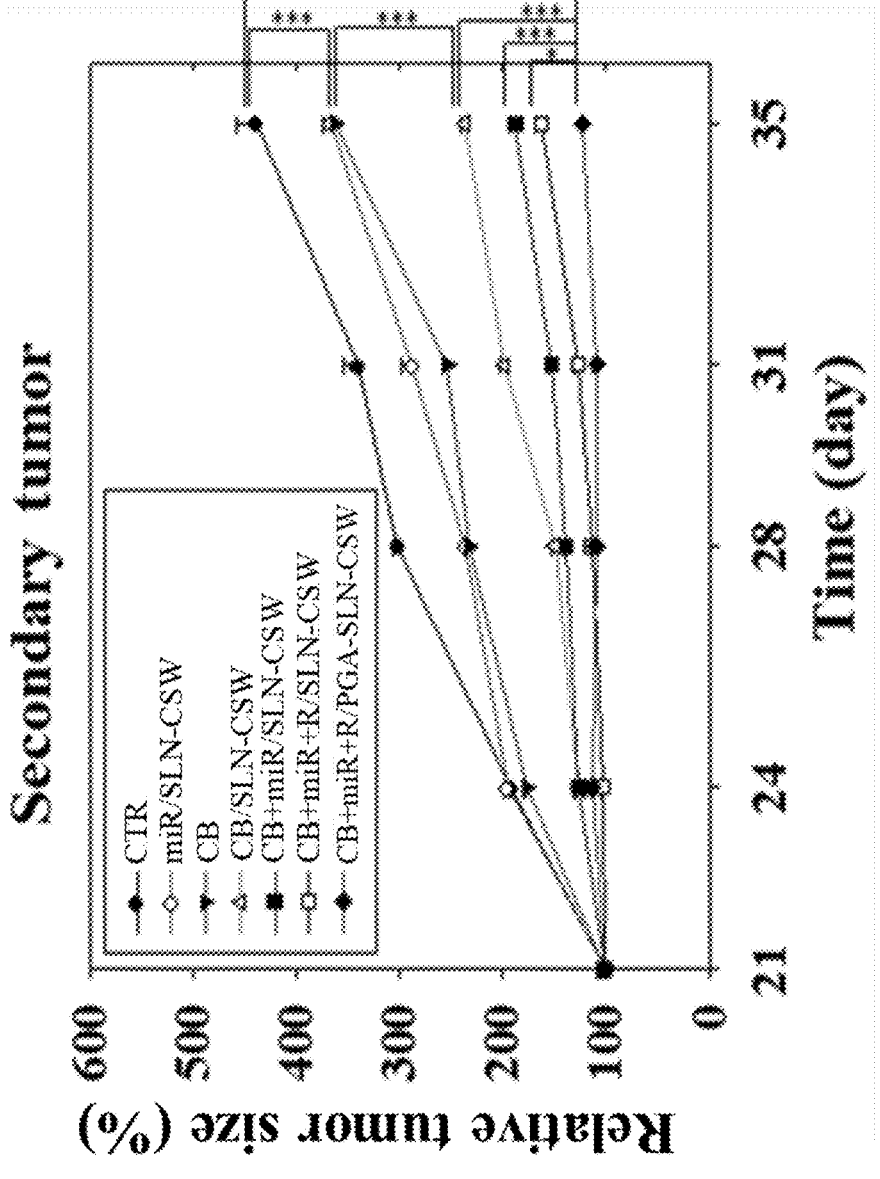
FIG. 25C shows the result of examination of the re-challenged tumor volume using a digital caliper twice a week for two weeks.
Figure 26A:
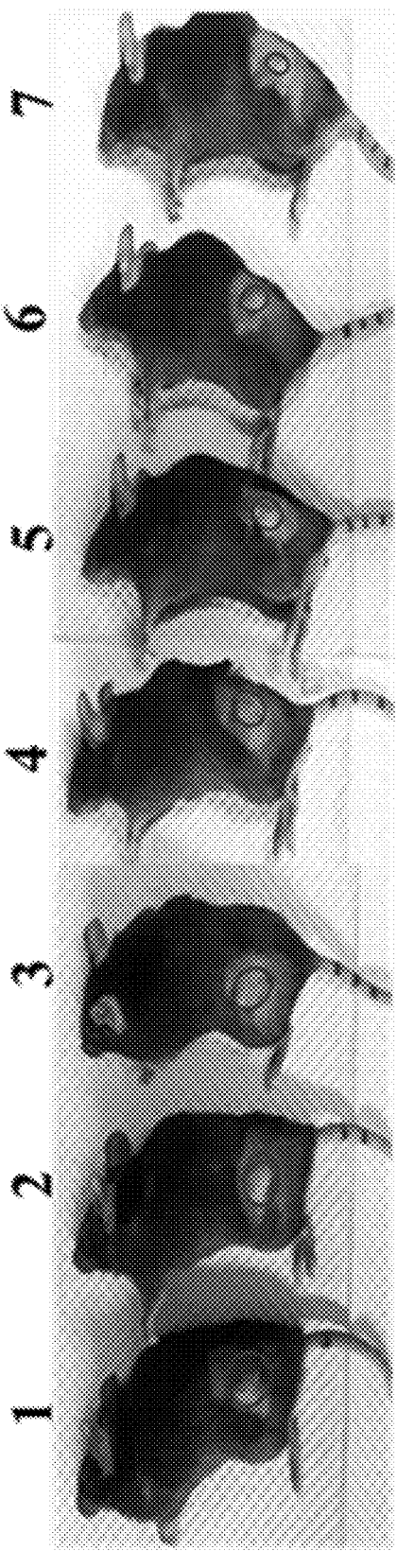
FIG. 26A shows representative images of Panc-02 re-challenge tumor bearing mice after 14 days.
Figure 26B:
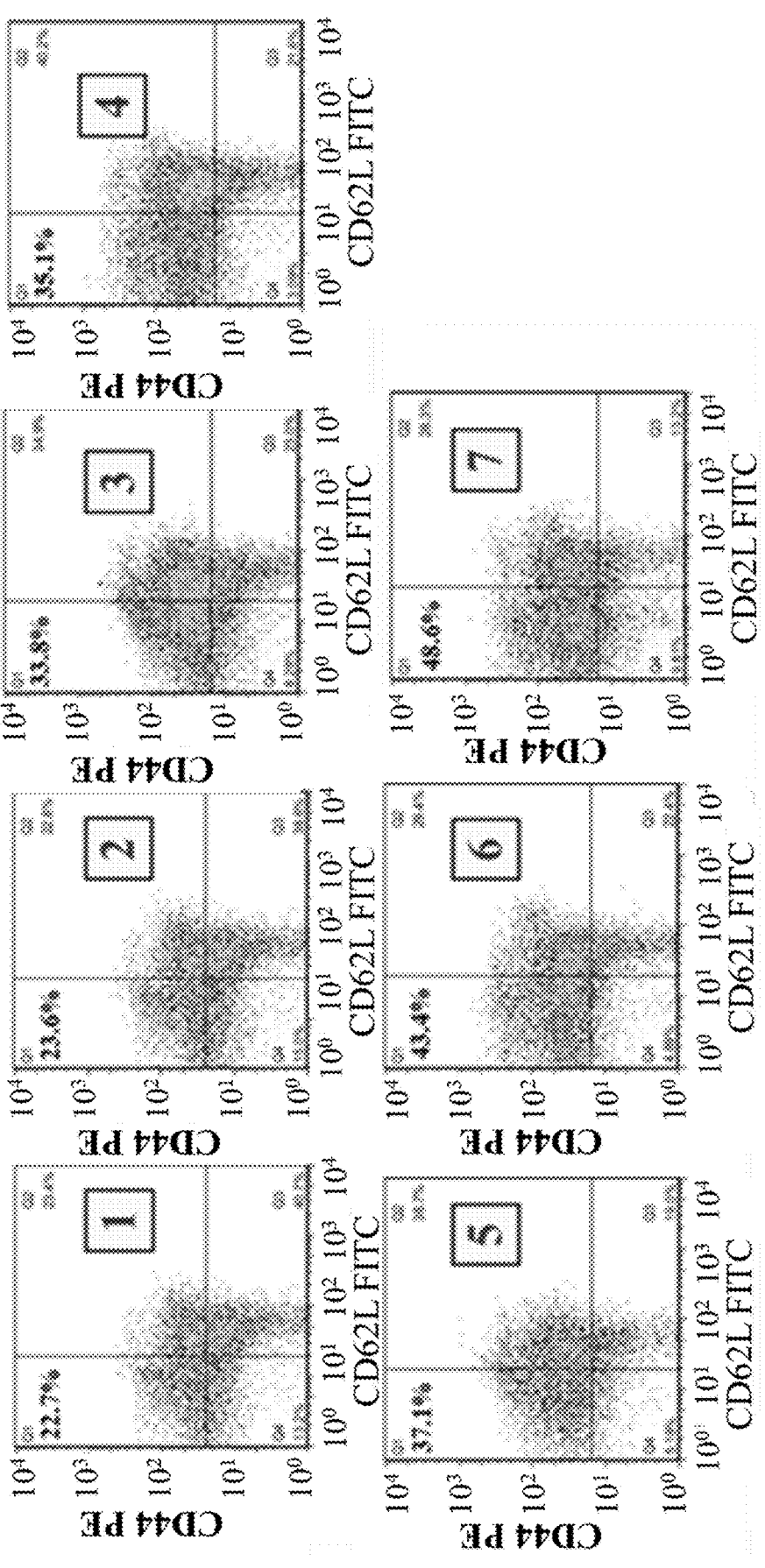
FIG. 26B shows the result of monitoring of the population distribution of effector memory T cells in the spleen collected from re-challenged Panc-02-bearing mice by flow cytometry.
Figure 26C:
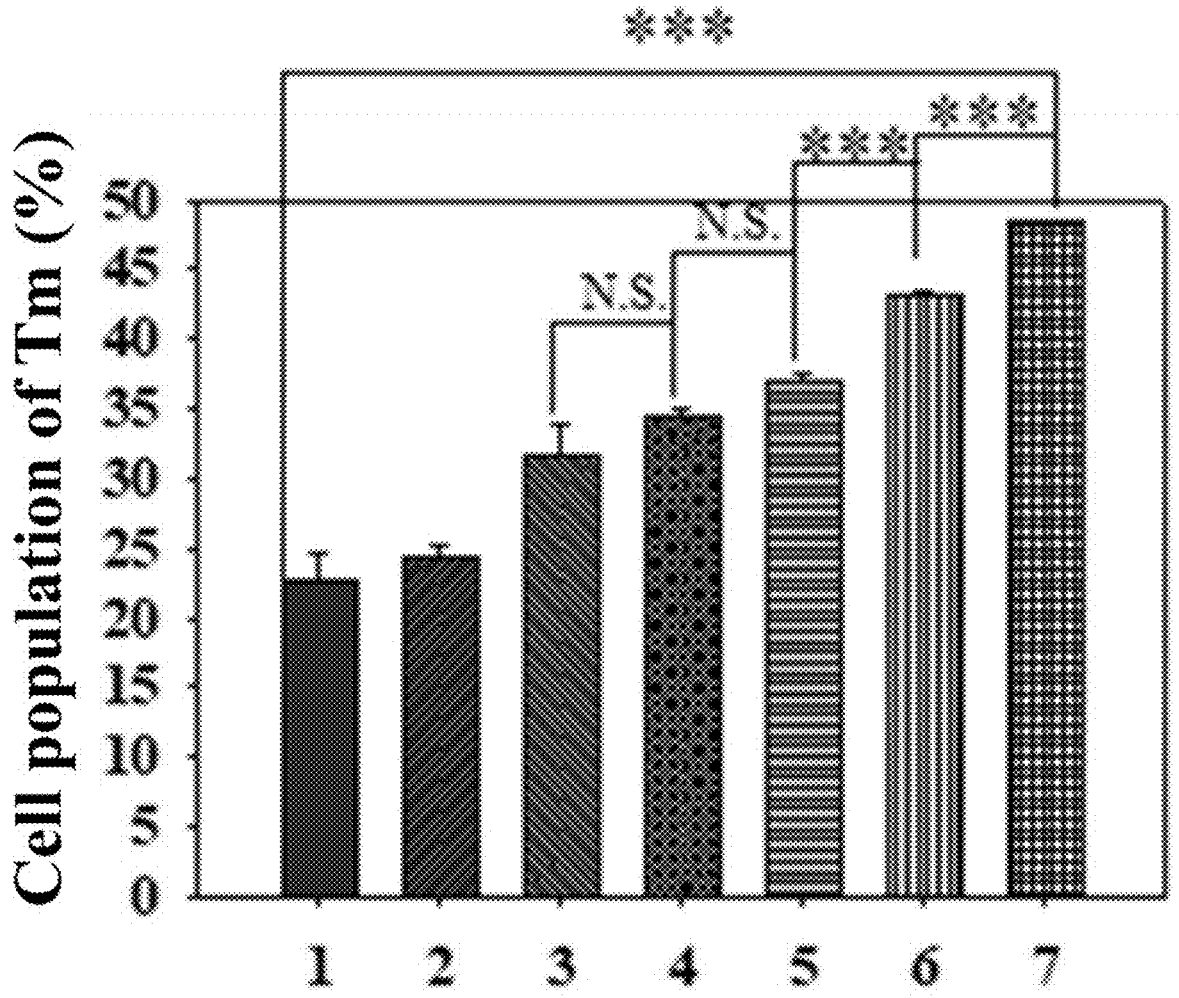
FIG. 26C shows quantification of the percentages of effector memory T cells (n=5; statistical significance at ***p<0.001; N.S.: p>0.05). 1: CTR; 2: miR/SLN-CSW; 3: CB; 4: CB/SLN-CSW; 5: CB+miR/SLN-CSW; 6: CB+miR+R/SLN-CSW; 7: CB+miR+R/PGA-SLN-CSW.

On the last day, the mice were sacrificed, and the following organs: tumors, hearts, livers, kidneys, spleens, and intestines were instantly taken and stored in 10% formalin. The tissues were paraffin embedded, sectioned, and stained with H&E. Following the manufacturer's instructions, tumor paraffin slices were deparaffinized and stained with fluorescent terminal deoxynucleotidyl transferase-mediated dUTP nick end labeling (TUNEL). The TUNEL assay images were acquired using a laser scanning microscope, while the H&E staining images were obtained using an Olympus microscope. The result is shown in FIG. 24C.

Example 25. Blood Cells Analysis

Figure 27A:
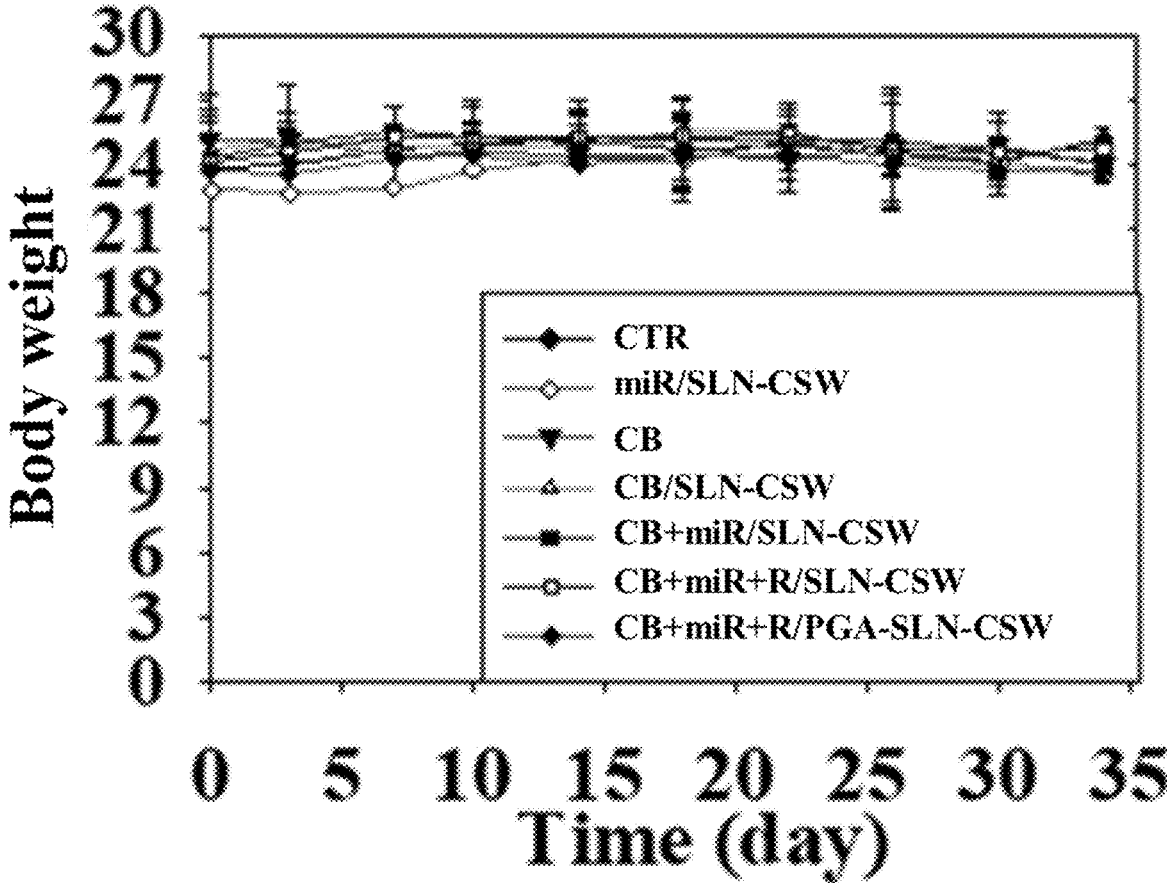
FIG. 27A shows body weight of Panc-02-bearing mice twice a week for 35 days.
Figure 27B:
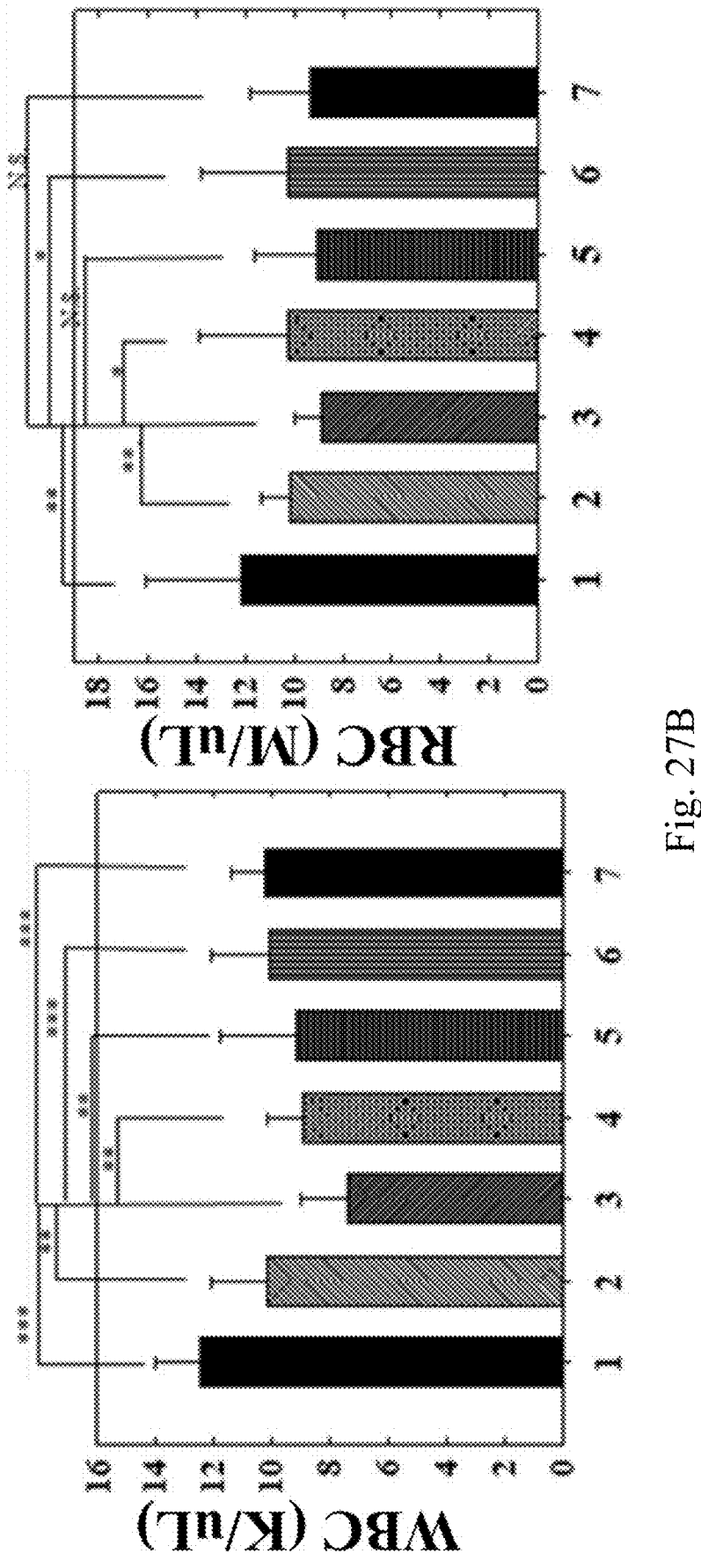
FIG. 27B shows hematological indices of white blood cells (WBC) and RBC of mice.
Figure 27C:
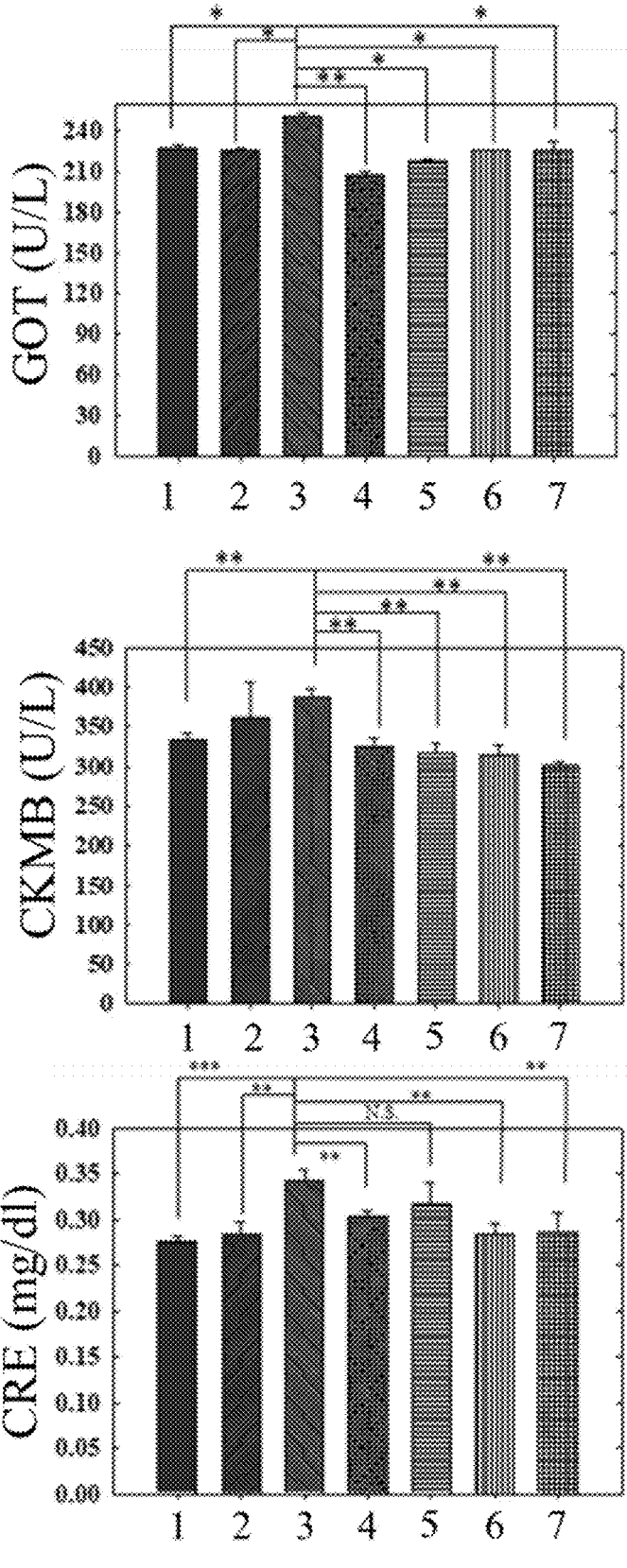
FIG. 27C shows biochemical indices of the liver by glutamic oxalocetic transaminase (GOT), kidneys by creatinine (CRE), and heart by creatine kinase-MB (CK-MB). Data are representative of five independent experiments and values are expressed in mean±SD. Statistical significance at *p<0.05; p<0.01; *p<0.001; N.S.: p>0.05).

Whole blood was taken by mice orbital sinus after the final treatment and transferred to an Eppendorf tube containing K₂EDTA. Hematology analyzers were used to count the numbers of white blood cells (WBC), red blood cells (RBC), and platelets (PLT). The result is shown in FIGS. 27A-27C.

Example 26. Biochemical Tests

Serum samples were analyzed to assess liver function (glutamic oxalocetic transaminase. GOT), kidney function (creatinine. CRE), and cardiac function (creatine kinase-MB. CK-MB) of mice using corresponding activity assay kits and a clinical dry chemistry analyzer. The result is shown in FIGS. 27A-27C.

Example 27. Biodistribution

Figure 28A:
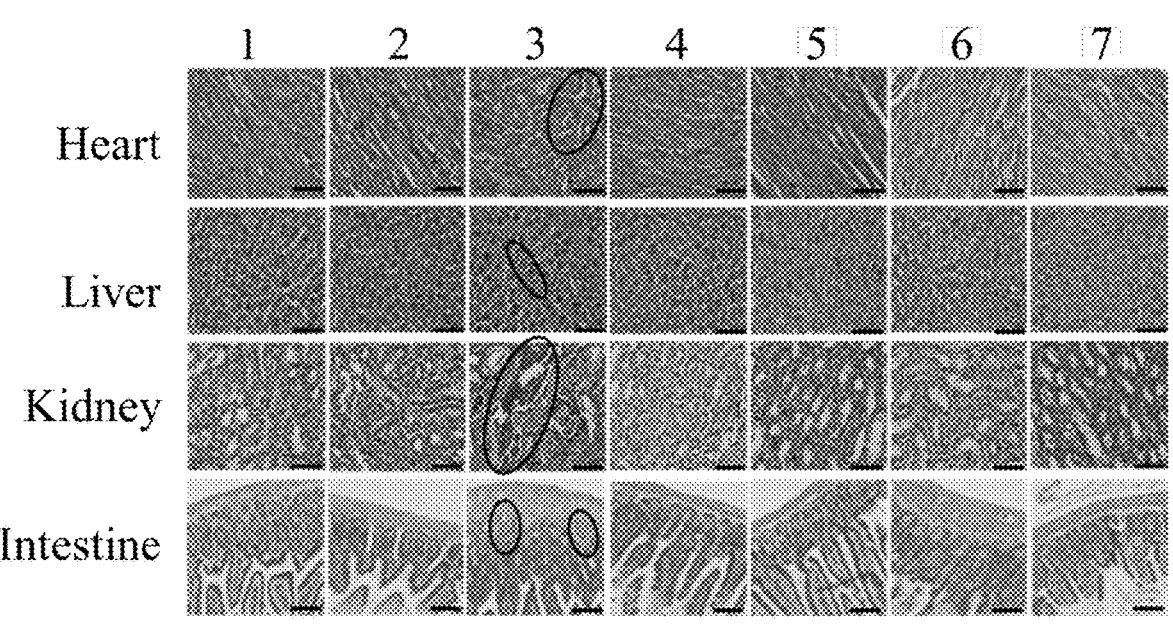
FIG. 28A shows histological photomicrographs of the heart, liver, kidneys, and intestines by H&E staining. Scale Bar: 200 μm.
Figure 28B:
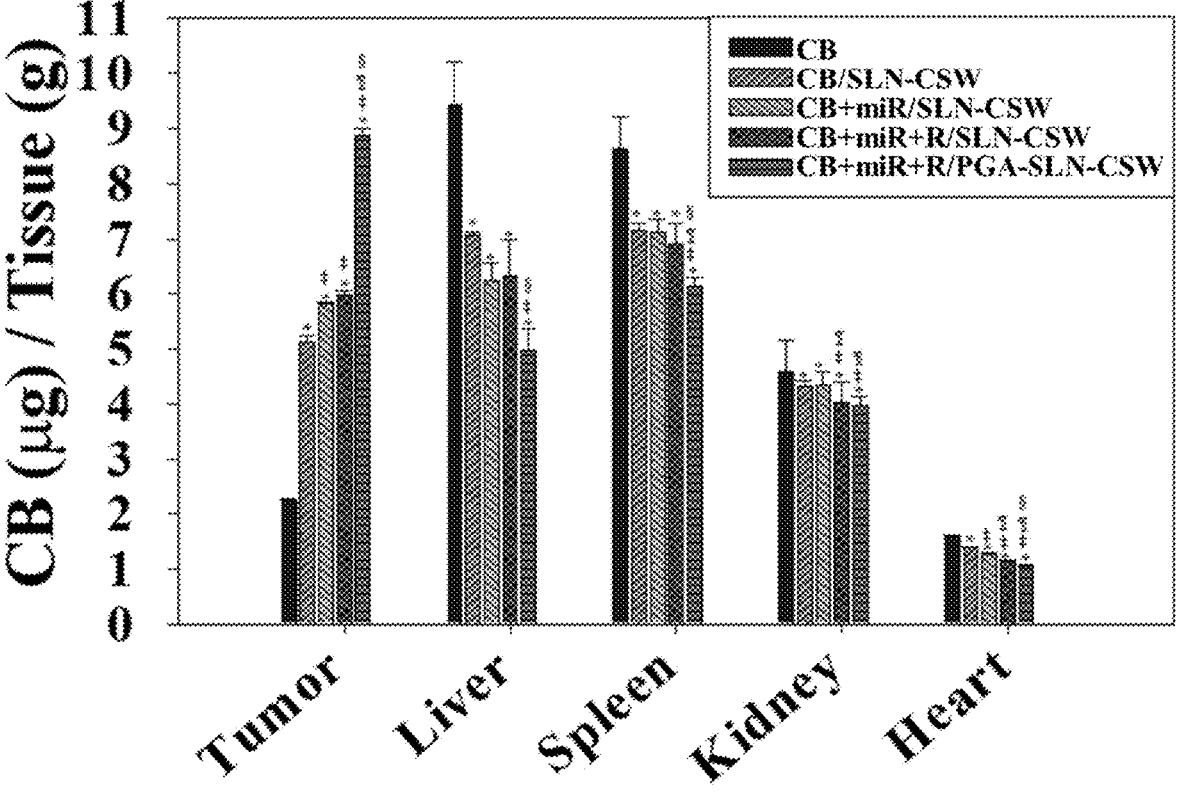
FIG. 28B shows biodistribution study of different formulations in Panc-02-bearing mice (n=5; *p<0.05 compared with CB, ‡p<0.05 compared with CB/SLN-CSW, ¶p<0.05 compared with CB+miR/SLN-CSW, and § p<0.05 compared with CB+miR+R/SLN-CSW via Student's t-test analysis). 1: CTR; 2: miR/SLN-CSW; 3: CB; 4: CB/SLN-CSW; 5: CB+miR/SLN-CSW; 6: CB+miR+R/SLN-CSW; 7: CB+miR+R/PGA-SLN-CSW.

After collection, the tissues were frozen in liquid nitrogen and preserved at −80° C. In order to extract CB, the frozen tissues were first cut into weights of 100-200 mg and mixed in a mortar and pestle with methanol and ddH₂O. Second, after collecting the samples in the tubes, the mortar was rinsed twice with 2 ml chloroform and once with 2 ml ddH₂O. After 15 minutes on ice, the samples were centrifuged at 3000 rpm for 15 minutes at 4° C. The solutions would then be divided into an upper methanol/water phase and a lower chloroform phase, with a protein and cellular debris layer in the center. The CB-containing down layer solutions were transferred to other tubes, and the concentration of CB was determined using UV/Vis. The result is shown in FIGS. 28A-28B.

Figure 29A:
FIG. 29A shows PET/MRI images of various formulations composed of P1 (1.25 mg/kg), Gemcitabine (GEM: 100 mg/kg), and/or AZD5069 (Z: 6 mg/kg) of Panc-02-bearing mice.
Figure 29B:
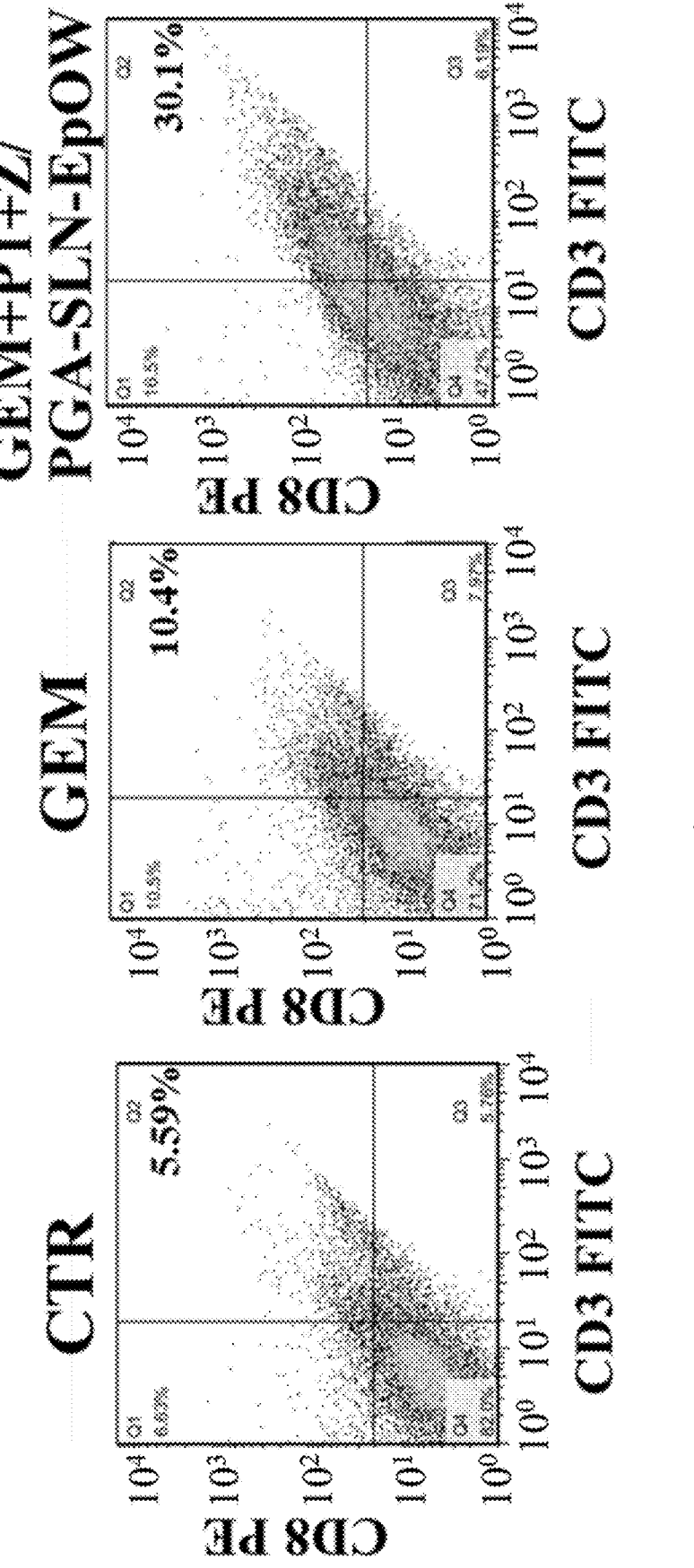
FIG. 29B shows the (A) PET/MRI images and (B) distribution of cytotoxic CD8 T cell clusters in mice carrying Panc-02 cells treated with different combinations of P1 (1.25 mg/kg), Gemcitabine (GEM: 100 mg/kg), and/or AZD5069 (Z: 6 mg/kg).

Example 28 Antitumor Immune Response, Efficacy, and Safety Profiles of GEM+P1+Z/PGA-SLN-EpOW. An ERS Inducer (GEM) and Immunotherapeutics (P1 Aptamer and AZD5069 (Z))-Loaded Nanoparticle Modified with Ep Aptamer and O, and W Peptides As shown in FIG. 29, by comparing different experimental groups, it was found that the nanoparticles (PGA-SLN-EpOW) containing GEM in combination with an immunotherapeutic (P1+AZD5069 (Z)) could reduce tumor size (FIG. 29A) and enhance antitumor immune response (FIG. 29B).

Figure 30:
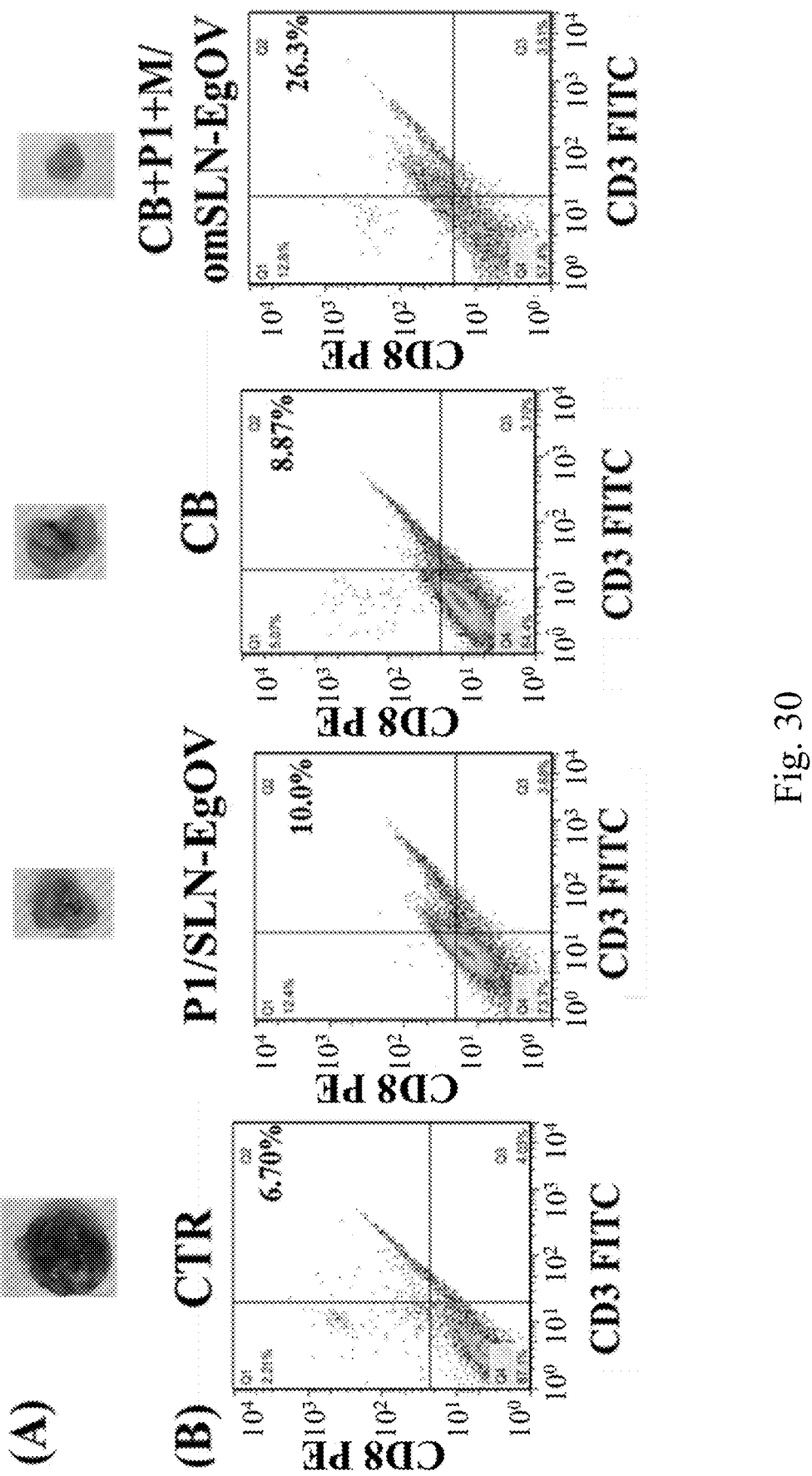
In FIG. 30, panels (A) and (B) show the antitumor immune response and distribution of cytotoxic CD8 T cell clusters in mice carrying CT-26 cells treated with different combinations of P1 (1.25 mg/kg), Gemcitabine (GEM: 100 mg/kg), and/or AZD5069 (Z: 6 mg/kg).

Example 29 Antitumor Immune Response, Efficacy, and Safety Profiles of CB+P1+M/omSLN-EgOV. An ERS Inducer (CB) and Immunotherapeutics (P1 Aptamer and Indoximod (M))-Loaded Nanoparticles Modified with Eg, V Aptamers and O Peptide As shown in FIG. 30, by comparing different experimental groups, it was found that the nanoparticles (omSLN-EgOV) containing CB in combination with an immunotherapeutic (P1+Indoximod (M)) could reduce tumor size (FIG. 30A) and enhance antitumor immune response (FIG. 30B).

Figure 31:
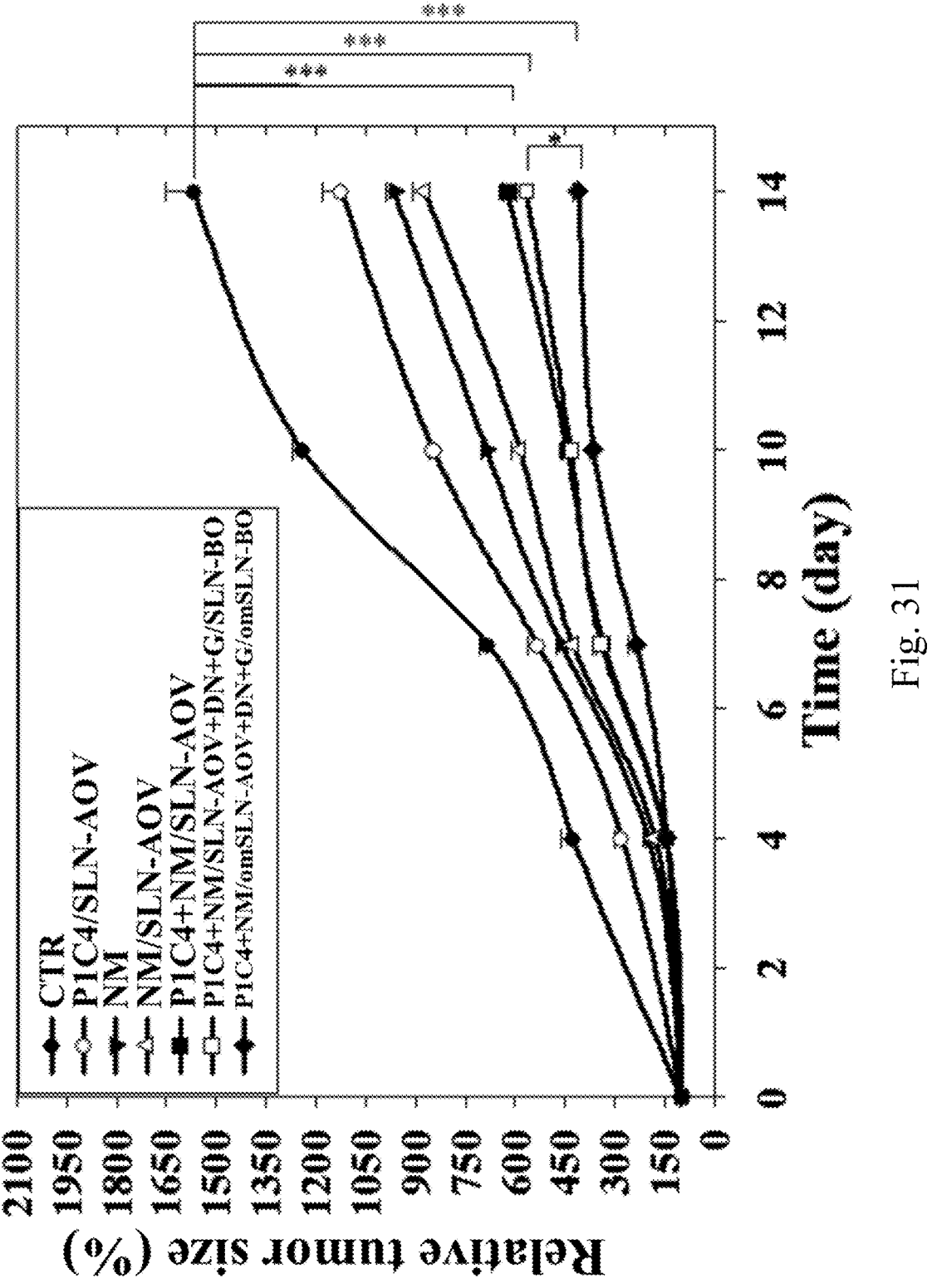
FIG. 31 shows the effect of reduction tumor size of NM+PIC4/omSLN-AOV in combination with DN+G/omSLN-BO.
Figure 32:
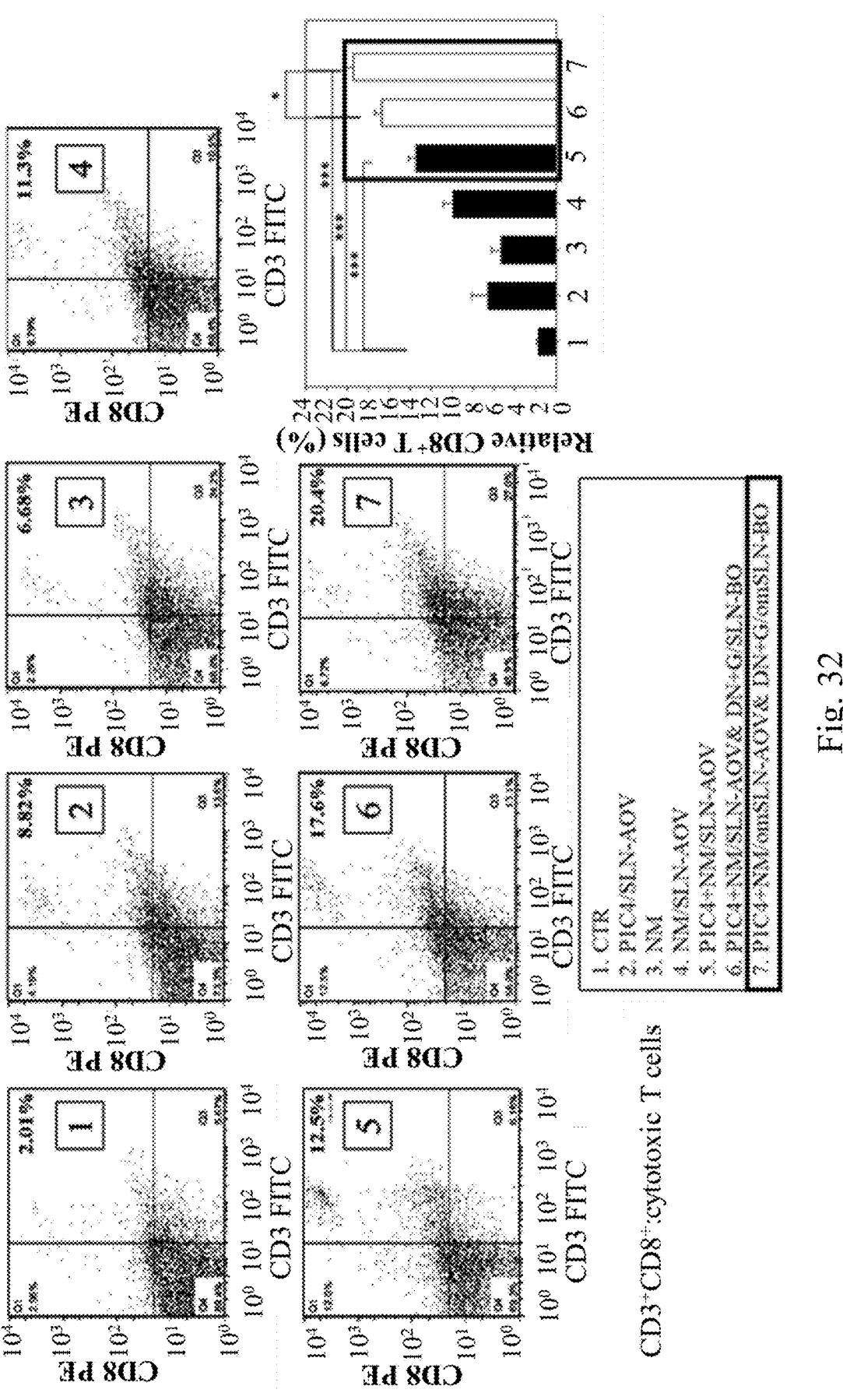
FIG. 32 shows the effect of enhance antitumor immune response of NM+PIC4/omSLN-AOV in combination with DN+G/omSLN-BO.

Example 31. Antitumor Immune Response, Efficacy, and Safety Profiles of NM+P1C4/omSLN-AOV and DN+G/omSLN-BO. An ERS Inducer (NM)+Immunotherapeutics (DN and G)-Loaded Nanoparticle Modified with a, B, O, and V Peptides in Mice Carrying Colon Cancer CT-26 Cells As shown in FIGS. 31-32, by comparing different experimental groups, it was found that NM+PIC4/omSLN-AOV in combination with DN+G/omSLN-BO could reduce tumor size (FIG. 31) and enhance antitumor immune response (FIG. 32).

CONCLUSIONS

Through the above experiments, this invention has developed a novel combination therapy strategy. The acid-detachable polymer shell of the negatively charged polyethylene glycol-polyglutamic acid (PEG-PGA) under physiological pH can create a space and charge barrier between the positive charged targeting peptide on the surface of solid lipid nanoparticle (SLN) through electrostatic interaction. Alternatively, the pH-responsive long-chain omPEG can form a steric barrier on the surface of SLN with the targeting molecule through omPEG-imine to protect peptide or aptamer from degradation by circulating peptidases. However, at the acidic pH of the tumor microenvironment, the acid-detachable PEG-PGA or omPEG imine can undergo hydrolysis, causing the de-coating effect to expose the cationic target peptide or the anionic target aptamer, thereby enhancing the targeting effect on cancer cells. The coating exhibits pH sensitivity under an acidic environment and does not cause hemolysis or cytotoxicity in normal mouse experiments.

After numerous attempts, we successfully identified a safe surfactant that can solubilize insoluble ERS inducer and immunoadjuvant. The ERS inducer and immunoadjuvant were then co-encapsulated in nanoparticles and delivered to tumors, ER, and immune cells with specificity. This strategy overcomes or reduces the high cytotoxicity and side effects, such as systemic inflammation and severe immune-related adverse events, of ERS inducer and immunoadjuvant on normal cells.

The experimental results show that the antitumor effect cannot only be attributed to the induction of cell apoptosis, but also to the inhibition of proliferation, tumor epithelial-mesenchymal transition, and cancer drug resistance-related pathways in cancer cells, including oncogenes, cell cycle regulatory factors, and immune-suppressive cytokines, as well as the enhancement of immune-promoting cytokines. Moreover, combining the tumor pH-responsive coating as a detachable outer shell of the nanoparticle can be applied to various types of tumors, such as colorectal cancer, head and neck cancer, pancreatic cancer, etc. This study demonstrates that the combination therapy of ERS inducer and immuno-therapeutic (microRNA or aptamer plus immunoadjuvants) can be a novel cancer-specific delivery strategy for targeting tumors, endoplasmic reticulum, and immune cells.

---

```
                        SEQUENCE LISTING

Sequence total quantity: 12
SEQ ID NO: 1            moltype = AA  length = 8
FEATURE                 Location/Qualifiers
source                  1..8
                        mol_type = protein
                        organism = synthetic construct
SEQUENCE: 1
TEEEQQLY                                                            8

SEQ ID NO: 2            moltype = AA  length = 8
FEATURE                 Location/Qualifiers
source                  1..8
                        mol_type = protein
                        organism = synthetic construct
SEQUENCE: 2
KLARLLTC                                                            8

SEQ ID NO: 3            moltype = DNA  length = 40
FEATURE                 Location/Qualifiers
source                  1..40
                        mol_type = other DNA
                        organism = synthetic construct
SEQUENCE: 3
ccaaggcctg caagggaacc aaggacacag tttttttttt               40

SEQ ID NO: 4            moltype = DNA  length = 51
FEATURE                 Location/Qualifiers
source                  1..51
                        mol_type = other DNA
                        organism = synthetic construct
SEQUENCE: 4
tgccgctata atgcacggat ttaatcgccg tagaaaagca tgtcaaagcc g          51

SEQ ID NO: 5            moltype = DNA  length = 48
FEATURE                 Location/Qualifiers
source                  1..48
                        mol_type = other DNA
                        organism = synthetic construct
SEQUENCE: 5
cactacagag gttgcgtctg tcccacgttg tcatgggggg ttggcctg              48

SEQ ID NO: 6            moltype = AA  length = 12
FEATURE                 Location/Qualifiers
source                  1..12
                        mol_type = protein
                        organism = synthetic construct
SEQUENCE: 6
WHRSYYTWNL NT                                                       12

SEQ ID NO: 7            moltype = AA  length = 6
FEATURE                 Location/Qualifiers
source                  1..6
                        mol_type = protein
                        organism = synthetic construct
SEQUENCE: 7
VRARTR                                                              6

SEQ ID NO: 8            moltype = DNA  length = 54
FEATURE                 Location/Qualifiers
source                  1..54
```

-continued

```
                     mol_type = other DNA
                     organism = synthetic construct
SEQUENCE: 8
acgggccaca tcaactcatt gatagacaat gcgtccactg cccgtttttt tttt         54

SEQ ID NO: 9         moltype = RNA   length = 45
FEATURE              Location/Qualifiers
source               1..45
                     mol_type = other RNA
                     organism = synthetic construct
SEQUENCE: 9
gcgtggtgtg atctagatgt attggctgat cctagtcagg tacgc                   45

SEQ ID NO: 10        moltype = AA   length = 8
FEATURE              Location/Qualifiers
source               1..8
                     mol_type = protein
                     organism = synthetic construct
SEQUENCE: 10
SLLMWITQ                                                             8

SEQ ID NO: 11        moltype = AA   length = 8
FEATURE              Location/Qualifiers
source               1..8
                     mol_type = protein
                     organism = synthetic construct
SEQUENCE: 11
SIINFEKL                                                             8

SEQ ID NO: 12        moltype = AA   length = 6
FEATURE              Location/Qualifiers
source               1..6
                     mol_type = protein
                     organism = synthetic construct
SEQUENCE: 12
CAEYLR                                                               6
```

The invention claimed is:

1. A target nanoparticle, comprising:

a nanoparticle core, wherein the surface of the nanoparticle core is modified with a target molecule;

a therapeutic agent inside the nanoparticle core; and an outer shell layer surrounding the outside surface of the nanoparticle core, the outer shell layer is coated with a tumor microenvironment acid-detachable polymer;

wherein the target molecule of the surface of the nanoparticle core and the tumor microenvironment acid-detachable polymer on the outer layer form a space and charge barrier via the electrostatic interaction;

wherein the target molecule comprises a cation target peptide and/or an anion target aptamer; wherein the cation target peptide comprises a tumor target peptide, an immune cell target peptide, an endoplasmic reticulum target peptide or a combination thereof;

wherein the anion target aptamer comprises a tumor target aptamer, an immune cell target aptamer or a combination thereof;

wherein the therapeutic agent comprises an ERS inducer and a nucleic acid immunomodulator;

wherein the tumor target peptide of the target molecule comprises C peptide (SEQ ID NO 2).

2. The target nanoparticle of claim 1, wherein the tumor microenvironment acid-detachable polymer is a PGA-PEG or an omPEG.

3. The target nanoparticle of claim 1, wherein the nanoparticle core is solid lipid nanoparticle (SLN), the nanoparticle core comprises L-α-phosphatidylcholine, glycerol monostearate, glycerol monopalmitate, glycerol monooleate, DSPE, DPPE, DOPE, DOTAP, DOTMA, SAINT 2, MC3 or KC2.

4. The target nanoparticle of claim 1, wherein the cation target peptide or the anion target aptamer can bind with receptor of over performance of EGFR, VEGFR, CXCR4, and CD44 on tumor.

5. The target nanoparticle of claim 1, wherein the cation target peptide or the anion target aptamer can bind with PD-1, PD-L1, neutrophil or other targets on immune cells such as macrophages, T cells or neutrophils.

6. The target nanoparticle of claim 1, wherein the tumor target aptamer comprises Ac aptamer (SEQ ID NO: 3), Eg aptamer (SEQ ID NO: 4) or Ep aptamer (SEQ ID NO: 5).

7. The target nanoparticle of claim 6, wherein the target nanoparticle is constructed by a conjugate of DSPE-PEG-C and the tumor target peptide, or constructed by a conjugate of DSPE-omPEG-Ac, DSPE-omPEG-Eg, or DSPE-omPEG-Ep and the tumor target aptamer.

8. The target nanoparticle of claim 1, wherein the immune cell target peptide comprises W peptide (SEQ ID NO: 6), V peptide (SEQ ID NO: 7), A peptide (SEQ ID NO: 12) or B peptide (SEQ ID NO: 13); wherein the immune cell aptamer comprises Al aptamer (SEQ ID NO: 8), or Ax aptamer (SEQ ID NO: 9).

9. The target nanoparticle of claim 8, wherein the target nanoparticle is constructed by a conjugate of DSPE-PEG-W, DSPE-PEG-V, DSPE-PEG-A or DSPE-PEG-B and the immune cell target peptide, or constructed by a conjugate of DSPE-omPEG-Al, or DSPE-omPEG-Ax and the immune cell target aptamer.

10. The target nanoparticle of claim 1, wherein the endoplasmic reticulum target peptide comprises S peptide (SEQ ID NO: 10) or O peptide (SEQ ID NO: 11).

11. The target nanoparticle of claim 10, wherein the target nanoparticle is constructed by a conjugate of DSPE-PEG-S or DSPE-PEG-O and the endoplasmic reticulum target peptide.

12. The target nanoparticle of claim 1, wherein the therapeutic agent further comprises an immunoadjuvant.

13. The target nanoparticle of claim 12, wherein the immunoadjuvant comprises resiquimod (R848, R), Imiquimod (R837), Vadimezan (dimethylxanthone acetic acid; DMXAA, ASA404), Indoximod (1-methyl-D-tryptophan, NLG-8189), DNase (DN), Lorlatinib, Galunisertib (LY-2157299, G), SB-431542, Lanraplenib, Reparixin (DF 1681Y) or T peptide (SEQ ID NO: 1).

14. The target nanoparticle of claim 1, wherein the nucleic acid immunomodulator is a nuclear aptamer or a miRNA.

15. The target nanoparticle of claim 14, wherein the nuclear aptamer is selected from the group consisting of Apt for anti-programmed cell death ligand-1; anti-PD-L1(p1), Apt for anti-programmed cell death protein-1; anti-PD-1 ($A_p$), anti-PD-L1/anti-cytotoxic T lymphocyte associated antigen-4; anti-CTLA-4(Apt(P1C4)), anti-lymphocyte activation gene 3 (LAG-3) Apt ($A_{lag}$), and anti-T cell immunoglobulin and mucin domain-3 (TIM-3) Apt ($A_t$).

16. The target nanoparticles of claim 14, wherein the miRNA is a has-miR-21 inhibitor or a miRNA mimic, wherein the miRNA mimic is selected from the group consisting of has-miR-122-5p, has-miR-125b-5p, has-miR-136-5p, has-miR-139-5p, has-miR-142-5p, has-miR-200c-3p, and has-miR-320.

17. The target nanoparticle of claim 1, wherein the ERS inducer comprises CB-5083, NMS-873, DBeQ, CB-5339 or Gemcitabine.

18. The target nanoparticle of claim 1, wherein the tumor microenvironment acid-detachable polymer can respond to acidic pH to become protonated and detached from the target nanoparticle in a pH 5-6.5 environment or tumor microenvironment.

19. The target nanoparticle of claim 1, wherein the target nanoparticle is de-coated of tumor microenvironment acid-detachable polymer on the outer shell layer at pH 6.0 environment to expose the cationic target peptide or the anionic target aptamer and bind with receptor or other targets of EGFR, VEGFR, CXCR4, CD44, PD-1, PD-L1 or neutrophil on tumors, macrophages, T cells or immune cells, to increase the uptake of the nanoparticle by cancer cells and reach the endoplasmic reticulum or cytoplasm.

20. A method for treating a cancer in a subject, comprising: administering an effective amount of target nanoparticles as claim 1, wherein the therapeutic agent comprises an ERS inducer and a nucleic acid immunomodulator wherein the cancer comprises pancreas, colon, or head and neck cancer.

21. The method of claim 20, wherein the therapeutic agent further comprises an immunoadjuvant.

\* \* \* \* \*